US007863313B2

(12) United States Patent
Morand et al.

(10) Patent No.: US 7,863,313 B2
(45) Date of Patent: Jan. 4, 2011

(54) METHODS FOR THE TREATMENT OF INFLAMMATORY DISEASES

(75) Inventors: Eric Francis Morand, Elwood (AU); Magdy Naguib Iskander, Sandringham (AU); Colin Edward Skene, Glen Waverley (AU)

(73) Assignee: Cortical PTY LTD, Victoria (AU)

( * ) Notice: Subject to any disclaimer, the term of this patent is extended or adjusted under 35 U.S.C. 154(b) by 24 days.

(21) Appl. No.: 10/552,595

(22) PCT Filed: Apr. 7, 2004

(86) PCT No.: PCT/AU2004/000453

§ 371 (c)(1),
(2), (4) Date: Jun. 20, 2006

(87) PCT Pub. No.: WO2004/089927

PCT Pub. Date: Oct. 21, 2004

(65) Prior Publication Data

US 2007/0010563 A1     Jan. 11, 2007

(30) Foreign Application Priority Data

Apr. 7, 2003   (AU)   ............... 2003901579
Dec. 8, 2003   (AU)   ............... 2003906773

(51) Int. Cl.
*A61K 31/415*   (2006.01)
*C07D 231/12*   (2006.01)
(52) U.S. Cl. .................................... 514/406; 548/377.1
(58) Field of Classification Search ................. 514/406; 548/377.1
See application file for complete search history.

(56) References Cited

U.S. PATENT DOCUMENTS 2,547,493 A     4/1951   Rowland ..................... 260/101
6,831,079 B1 *  12/2004  Yoon et al. .................. 514/220

FOREIGN PATENT DOCUMENTS

WO   WO03-013518     *  2/2003
WO   WO 03013518 A1  *  2/2003

OTHER PUBLICATIONS

Wu and Farrelly, Toxicology 236:1-6, 2007.*
Fukata et al., Yakugaku Zasshi (1974), 94(1), p. 36-43, in STN search report.*
Bacher, M., et al., "An essential regulatory role for macrophage migration inhibitory factor in T-cell activation," *Proc. Natl. Acad. Sci. USA*, 93(15):7849-7854 (Jul. 23, 1996).
Bozza, M., et al., "Targeted disruption of migration inhibitory factor gene reveals its critical role in sepsis," *J. Exp. Med.*, 189(2):341-346 (Jan. 18, 1999).

Bucala, R., "MIF rediscovered: cytokine, pituitary hormone, and glucocorticoid-induced regulator of the immune response," *FASEB J.*, 10(14):1607-1613 (Dec. 1996).
Calandra, T., et al., "MIF as a glucocorticoid-induced modulator of cytokine production," *Nature*, 377(6544):68-71 (Sep. 7, 1995).
David, J.R., "Delayed hypersensitivity in vitro: its mediation by cell-free substances formed by lymphoid cell-antigen interaction," *Proc. Natl. Acad. Sci. USA*, 56(1):72-77 (Jul. 1966).
Donnelly, S.C., et al., "Regulatory role for macrophage migration inhibitory factor in acute respiratory distress syndrome," *Nat. Med.*, 3(3):320-323 (Mar. 1997).
Jüttner, S., et al., "Migration inhibitory factor induces killing of Leishmania major by macrophages: dependence on reactive nitrogen intermediates and endogenous TNF-alpha," *J. Immunol.*, 161(5):2383-2390 (Sep. 1, 1998).
Karimi, B., et al., "Efficient and chemoselective conversion of carbonyl compounds to 1,3-dioxanes catalyzed with N-bromosuccinimide under almost neutral reaction conditions," *Org. Lett.*, 1(11):1737-1739 (1999).
Lacey, D., et al., "Control of fibroblast-like synoviocyte proliferation by macrophage migration inhibitory factor," *Arthritis Rheum.*, 48(1):103-109 (Jan. 2003).
Leech, M., et al., "Macrophage migration inhibitory factor in rheumatoid arthritis: evidence of pro-inflammatory function and regulation by glucocorticoids," *Arthritis & Rheumatism*, 42(8):1604-1608 (Aug. 1999).
Leech, M., et al., "Regulation of macrophage migration inhibitory factor by endogenous glucocorticoids in rat adjuvant arthritis," *Arthritis & Rhermatism*, 43(4):827-833 (Apr. 2000).
Leech, M., et al., "Regulation of p53 by macrophage migration inhibitory factor in inflammatory arthritis," *Arthritis Rheum.*, 48(7):1881-1889 (Jul. 2003).

(Continued)

*Primary Examiner*—Yong Chu
(74) *Attorney, Agent, or Firm*—King & Spalding LLP

(57) ABSTRACT

Methods of inhibiting the cytokine or biological activity of Macrophage Migration Inhibitory Factor (MIF) comprising contacting MIF with a compound of formula (I) are provided. The invention also relates to methods of treating diseases or conditions where MIF cytokine or biological activity is implicated comprising administration of compounds of formula (I), either alone or as a part of combination therapy. Novel compounds of formula (I) are also provided for.

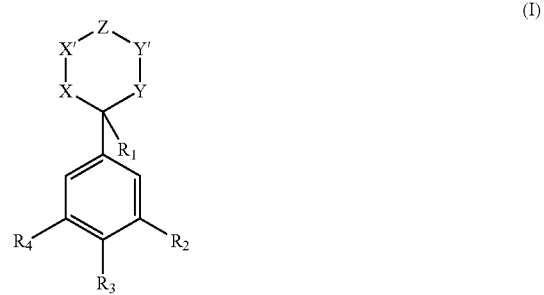

1 Claim, 10 Drawing Sheets

OTHER PUBLICATIONS

Liang, X., et al., "Solution-phase combinatorial synthesis using multicomponent Grignard reagents," *J. Chem. Soc., Perkin Trans. I*, 2002:503-508 (2002).

Mimura, T., et al., "Platelet anti-aggregant activity of 2,2-dimethylthiazolidine hydrochloride and 2-(4-hydroxy-3-methoxyphenyl)thiazolidine," *Chem. Pharm. Bull.*, 36(3):1110-1116 (1988).

Mitchell, R.A., et al., "Sustained mitogen-activated protein kinase (MAPK) and cytoplasmic phospholipase A2 activation by macrophage migration inhibitory factor (MIF). Regulatory role in cell proliferation and glucocorticoid action," *J. Biol. Chem.*, 274(25):18100-18106 (Jun. 18, 1999).

Morand, E.F., et al., "Macrophage migration inhibitory factor: an emerging therapeutic target in rheumatoid arthritis," *Arthritis & Rheumatism*, 48(2):291-299 (Feb. 2003).

Perrin, C.L., et al., "Stereoelectronic control in addition of nucleophiles to an amidinium ion," *J. Am. Chem. Soc.*, 123:4451-4458 (2001).

Quallich, G.J., et al., "Synthesis of 1,2,3,4-tetrahydroisoquinolines containing electron-withdrawing groups," *J. Org. Chem.*, 63(12):4116-4119 (1998).

Robbe, Y., et al., "Radioprotection chimique comparée de diverses structures hétéro-cycliques pentagonales á deux hétéroatomes," *Eur. J. Med. Chem.—Chim. Ther.*, 17(3):235-243 (1982).

Sabroe, I., et al., "Asthma and MIF: innately Th1 and Th2," *Clin. Exp. Allergy*, 30(9):1194-1196 (Sep. 2000).

Samajdar, S., et al., "A new molecular iodine-catalyzed thioketalization of carbonyl compounds: selectivity and scope," *Tetrahedron Lett.*, 42:4425-4427 (2001).

Sampey, A.V., et al., "Annexin I and dexamethasone effects on phospholipase and cyclooxygenase activity in human synoviocytes," *Mediators Inflamm.*, 9(3-4):125-132 (2000).

Sampey, A.V., et al., "Regulation of synoviocyte phospholipase A2 and cyclooxygenase 2 by macrophage migration inhibitory factor," *Arthritis Rheum*, 44(6):1273-1280 (Jun. 2001).

Santos, L., et al., "Role of macrophage migration inhibitory factor (MIF) in murine antigen-induced arthritis: interaction with glucocorticoids," *Clin. Exp. Immunol.*, 123(2):309-314 (Feb. 2001).

Santos, L.L., et al., "Suppression of adjuvant arthritis and synovial macrophage inducible nitric oxide by N-iminoethyl-L-ornithine, a nitric oxide synthase inhibitor," *Inflammation*, 21(3):299-311 (Jun. 1997).

Spychala, J., "4-(Cyclic amidino)phenols- preparation and use in a diamidine synthesis," *Synthetic Communications*, 30(6):1083-1094 (2000).

Srikrishna, A., et al., "A mild and simple procedure for the reductive cleavage of acetals and ketals," *Tetrahedron*, 31(11):3339-3344 (1995).

Sumiya, F., et al., "Conjugated-triene intermediates in the Sommelet-Hauser rearrangement of cyclic 1-methyl-2-phenylammonium 1-methylides," *Chem. Pharm. Bull.*, 39(1):36-40 (Jan. 1991).

Weiser, W.Y., et al., "Molecular cloning of a cDNA encoding a human macrophage migration inhibitory factor," *Proc. Natl. Acad. Sci. USA*, 86(19):7522-7526 (Oct. 1989).

Wenis, E., et al., "The synthesis of p-aminosalicyclic acid hydrochloride," *J. Am. Pharm. Assoc.*, 38:9-11 (1949) (Abstract only).

Wilk, I.J., et al., "The action of lithium aluminum hydride on 3-methyl-5-phenylhydantoin and 5-phenylhydantoin," *J. Org. Chem.*, 15:1020-1022 (1950).

Yus, M., et al., "A new and direct synthesis of 2-substituted pyrrolidines," *J. Org. Chem.*, 66(18):6207-6208 (2001).

Seeliger, STN File CA AN 64:36357 & DE 1206585 A, Dec. 9, 1965, CAS RN 10200-70-1.

Cashman et al., STN File CA AN 112:174715, "Oxygenation of dialkyl sulfides by modified sharpless reagent: a model system for the flavin-containing monooxygenase," J. Am. Chem. Soc. 1990, 112(8), 3191-5, CAS RN 127732-82-5.

Langer et al., STN File CA AN 85:5050, "Attempted conformational alterations on cyclic systems, part 4. Ring distortions and rotameric behaviour of the phenyl group in 2,2-disubstituted-1,3-dioxantes," Monatsh. Chem., 1976, 107(1), 1-17, CAS RN 59356-52-4.

Kalff et al., STN File CA AN 65:29021, "Conformation of non-aromatic ring compounds. XX. Dipole moments and N.M.R. spectra of some 2-substituted 1,3-dithianes," Rec. Trav. Chim. Pays-Bas, 1966, 85(5), 467-84, CAS RN 10359-12-3.

Alderweireldt et al., STN File CA AN 64:51391, "Nuclear magnetic resonance experiments on ketals. V. Conformation of 2-substituted 1,3-dioxolanes," Bull. Soc. Chim. Belges, 1965, 74(11-12), 488-505, CAS RN 6135-56-4.

Das et al., STN File CA AN 77:87199, "Substitute effects on molecular ion abundance," Ind. J. Chem., 1972, 10(3), 277-278, CAS RN 36881-02-4.

Suzuki et al., STN File CA AN 101:22812, "Photochemical reactions of 2-(4-substituted phenyl)-2-thiazolines: cycloelimination of benzonitriles and ethylene sulfide and dehydrogenation to thiazoles," Research Reports of the Faculty of Engineering, Mie university, 1983, 8, 43-53, CAS RN 90595-44-1.

Cook et al., STN File CA AN 44:49326, "Thiazolidines," Chemistry of Penicillin, Princeton University Press, 1949, 921-72, CAS RN 31404-08-7.

Hamon et al., STN File CA AN 124:175533, "Enantioselective syntheses of 2-arylpropanoic aci non-steroidal anti-inflammatory drugs and related compounds," Tetrahedron, 1995, 51(46), 12645-60, CAS RN 4360-68-3.

Wilkerson et al., STN File CA AN 118:101592, "Antiinflammatory phospholipase-A2 inhibitors. II. Design, synthesis and structure-activity relationship," Eur. J. Med. Chem., 1992, 27(6), 595-610, CAS RN 36714-65-5.

Wilkerson et al., STN File CA AN 116:194619, "Antiinflammatory phospholipase-A2 inhibitors. L," Eur. J. Med. Chem., 1991, 26(7), 667-76, CAS RN 138688-69-4.

Kano et al., STN File CA AN 97:162920, "A new and facile synthesis of 5-arylpyrimidines and 4-arylpyrazoles," Heterocycles, 1982, 19(6), 1079-82, CAS RN 37921-11-2, 82525-24-4, 82525-25-5, 82525-26-6, 82525-28-8, 82525-29-9, 82525-30-2, 82525-31-3.

Aeberli et al., STN File CA AN 70:47376, "Synthesis and anti-inflammatory activity of 2-aryl-2-$^N_A$-piperidyl-1,3-dioxanes," J. Med. Chem., 1969, 12(1), 51-54, CAS RN 13581-17-4, 13581-19-6, 13581-41-4, 13850-45-8, 14017-85-7, 21464-43-7, 21464-88-0.

Henkel et al., Derwent Abstract Accession No. 02172Y/02, Class D21 E13, DT 2526312 A, Dec. 1976.

PCT/AU2004/000453, International Search Report, Jun. 4, 2004, 1-7.

\* cited by examiner

METHODS FOR THE TREATMENT OF INFLAMMATORY DISEASES

CROSS REFERENCE TO RELATED APPLICATIONS

This application is a United States national phase filing under 35 U.S.C. §371 of International Application No. PCT/AU2004/000453 filed Apr. 7, 2004, which claims priority to Australia Patent Application No. 2003901579, filed Apr. 7, 2003, and Australia Patent Application No. 2003906773, filed Dec. 8, 2003.

FIELD OF THE INVENTION

The present invention relates generally to the treatment of diseases or conditions resulting from cellular activation, such as inflammatory or cancerous diseases or conditions. In particular, the invention relates to the use of phenyl substituted cyclic derivatives to inhibit the cytokine or biological activity of macrophage migration inhibitory factor (MIF), and diseases or conditions wherein MIF cytokine or biological activity is implicated.

BACKGROUND TO THE INVENTION

MIF is the first identified T-cell-derived soluble lymphokine. MIF was first described as a soluble factor with the ability to modify the migration of macrophages [1]. The molecule responsible for the biological actions ascribed to MIF was identified and cloned in 1989 [2]. Initially found to activate macrophages at inflammatory sites, it has been shown to possess pluripotential actions in the immune system. MIF has been shown to be expressed in human diseases which include inflammation, injury, ischaemia or malignancy. MIF also has a unique relationship with glucocorticoids by overriding their anti-inflammatory effects.

Recent studies have indicated that monoclonal antibody antagonism of MIF may be useful in the treatment of sepsis, certain types of cancers and delayed type hypersensitivity. Antibody antagonism of MIF has also been shown to have activity in adjuvant- or collagen-induced arthritis animal models and other models of inflammatory and immune diseases.

Although antibody antagonism of MIF is one potential way to provide therapeutic treatments, such biological molecules can be expensive to prepare on a commercial basis and further, can be limited in the way they are administered (generally by injection) and do not readily lend themselves to formulations for administration by other means eg oral administration.

Small molecule inhibitors may overcome one or more such difficulties connected with the use of biological therapeutic treatments. There exists a need, therefore, for small molecule inhibitors of the cytokine or biological activity of MIF. Small molecule inhibitors of the cytokine or biological activity of MIF would have therapeutic effects in a broad range of diseases, whether given alone or in combination with other therapies.

Further, glucocorticoids have been used to treat human diseases for over fifty years and are effective in a range of diseases which include inflammation, injury, ischaemia or malignancy. Although debate continues in relation to their impact on disease progression, their influence on symptoms and signs of inflammation, especially in the short term, can be dramatic.

Despite their benefits and efficacy, the use of glucocorticoids is limited by universal, predictable, dose-dependent toxicity. Mimicking Cushing's disease, a disease wherein the adrenal glands produce excess endogenous glucocorticoids, glucocorticoid treatment is associated with side effects including immunosuppression (resulting in increased susceptibility to infections), weight gain, change in body habitus, hypertension, oedema, diabetes mellitus, cataracts, osteoporosis, poor wound healing, thinning of the skin, vascular fragility, hirsutism and other features of masculinization (in females). In children, growth retardation is also noted. These side effects are known as Cushingoid side effects.

Since the side effects of glucocorticoids are dose dependent, attempts to reduce the dosage requirement have been investigated, including combination therapies in which glucocorticoids are administered with other therapeutic agents. These combination therapies are sometimes referred to as "steroid-sparing" therapies. However, currently available combination therapies are non-specific as the other therapeutic agents do not address biological events which inhibit the effectiveness of glucocorticoids. Such combination therapies are also typically associated with serious side effects.

Furthermore, glucocorticoids are incompletely effective in a number of disease settings, leading to the concept of "steroid-resistant" diseases. Agents which amplify or enhance the effects of glucocorticoids would not only allow the reduction of dose of these agents but may also potentially render "steroid-resistant" diseases steroid-sensitive.

There is a need for effective therapies which enable a reduction in the dosage level of glucocorticoids. There is also a need for effective treatment of "steroid-resistant" diseases. Preferably, such therapies or treatments would address factors which directly limit the effectiveness of glucocorticoids.

Therapeutic antagonism of MIF may provide "steroid-sparing" effects or be therapeutic in "steroid-resistant" diseases. Unlike other pro-inflammatory molecules, such as cytokines, the expression and/or release of MIF can be induced by glucocorticoids [3, 4]. Moreover, MIF is able to directly antagonize the effects of glucocorticoids. This has been shown to be the case for macrophage TNF, IL-1, IL-6 and IL-8 secretion [5, 6], and for T cell proliferation and IL-2 release [7]. In vivo, MIF exerts a powerful glucocorticoid-antagonist effect in models including endotoxic shock and experimental arthritis [5, 8]. In the context of an inflammatory or other disease treated with glucocorticoids, then, MIF is expressed but exerts an effect which prevents the glucocorticoid inhibition of inflammation. It can therefore be proposed that therapeutic antagonism of MIF would remove MIF's role in inhibiting the anti-inflammatory effect of glucocorticoids, thereby allowing glucocorticoids to prevail. This would be the first example of true "steroid-sparing" therapy. In support of this hypothesis is the observation that anti-MIF antibody therapy reverses the effect of adrenalectomy in rat adjuvant arthritis [9]. By neutralizing the natural glucocorticoid 'counter-regulator' effect of MIF, it is envisioned that with MIF antagonism, steroid dosages could be reduced or even eliminated in inflammatory disease, particularly in those diseases that are associated with the glucocorticoid resistance [10, 11]. There is a need, therefore, for therapeutic antagonists of the cytokine or biological activity of MIF.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

In a first aspect, the present invention provides a compound of formula (I), or a pharmaceutically acceptable salt or prodrug thereof

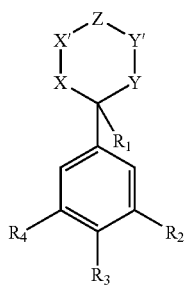

(I)

wherein X and X' are independently selected from —C($R_5$)$_2$—, —O—, —S—, —N($R_5$)—, or taken together form —C($R_5$)=C($R_5$)—, —C($R_5$)=N—, —N=C($R_5$)—, —N($R_5$)—N($R_5$)— or —N=N—;

Y and Y' are independently selected from —C($R_5$)$_2$—, —O—, —S—, —N($R_5$)—, or taken together form —C($R_5$)=C($R_5$)—, —C($R_5$)=N—, —N=C($R_5$)—, —N($R_5$)—N($R_5$)— or —N=N—;

Z is —C($R_5$)$_2$—, —O—, —S— or —N($R_5$)—, or forms a covalent single or double bond between X' and Y', or Z together with X' or Y' forms —C($R_5$)=C($R_5$)—, —C($R_5$)=N—, —N=C($R_5$)—, —N($R_5$)—N($R_5$)— or —N=N—, wherein when Z is —O—, —S— or —N($R_5$)—, X' and Y' are —C($R_5$)$_2$—;

when X is —O—, —S— or —N($R_5$)—, X' is —C($R_5$)$_2$—;

when Y is —O—, —S— or —N($R_5$)—, Y' is —C($R_5$)$_2$—; or

X or Y together with the carbon atom bearing the phenyl group form a double bond wherein which ever of X or Y forms part of the double bond is selected from —C($R_5$)— and —N—;

$R_1$ is selected from hydrogen, $C_{1-20}$alkyl, $C_{2-20}$alkenyl, $C_{2-20}$alkynyl, (A)$_n$C(O)$R_6$, (A)$_n$C(S)$R_6$, (A)$_n$S(O)$R_6$, (A)$_n$S(O)$_2R_6$, (A)$_n$O$R_7$, (A)$_n$S$R_7$, (A)$_n$N($R_8$)$_2$, (A)$_n$C(=N$R_9$)$R_{10}$ and (A)$_n R_{11}$, or when X or Y together with the carbon atom bearing the phenyl group form a double bond, $R_1$ is absent;

$R_2$ and $R_4$ are independently selected from hydrogen, $C_{1-3}$alkyl and (A)$_m R_{12}$;

$R_3$ is selected from $C_{1-3}$alkyl, (A)$_m R_{12}$, (A)$_m$aryl and (A)$_m$heterocyclyl;

$R_5$ is selected from hydrogen, $C_{1-20}$alkyl, $C_{2-20}$alkenyl, $C_{2-20}$alkynyl, (A)$_n$C(O)$R_6$, (A)$_n$C(S)$R_6$, (A)$_n$S(O)$R_6$, (A)$_n$S(O)$_2R_6$, (A)$_n$O$R_7$, (A)$_n$S$R_7$, (A)$_p$N($R_8$), (A)$_n$C(=N$R_9$)$R_{10}$ and (A)$_n R_{11}$;

$R_6$ is selected from hydrogen, $C_{1-20}$alkyl, $C_{2-20}$alkenyl, $C_{2-20}$alkynyl, OH, OC$_{1-10}$alkyl, OC$_{2-10}$alkenyl, OC$_{2-10}$alkynyl, O(A)$_q R_{11}$, SH, SC$_{1-10}$alkyl, SC$_{2-10}$alkenyl, SC$_{2-10}$alkynyl, S(A)$_q R_{11}$, N($R_{13}$)$_2$, [NH—CH($R_{14}$)C(O)]$_8$—OH, [NH—CH($R_{14}$)C(O)]$_s$—OC$_{1-3}$alkyl, [sugar]$_s$ and (A)$_q R_{11}$;

$R_7$ is selected from hydrogen, $C_{1-20}$alkyl, $C_{2-20}$alkenyl, $C_{2-20}$alkynyl, (A)$_q R_{11}$, C(O)H, C(O)C$_{1-10}$alkyl, C(O)C$_{2-10}$alkenyl, C(O)C$_{2-10}$alkynyl, C(O)-aryl, C(O)(A)$_q R_{11}$, C(O)$_2$H, C(O)$_2 C_{1-10}$alkyl, C(O)$_2 C_{2-10}$alkenyl, C(O)$_2 C_{2-10}$alkynyl, C(O)$_2$-aryl, C(O)$_2$(A)$_q R_{11}$, C(S)H, C(S)C$_{1-10}$alkyl, C(S)C$_{2-10}$alkenyl, C(S)C$_{2-10}$alkynyl, C(S)-aryl, C(S)(A)$_q R_{11}$, C(S)OH, C(S)OC$_{1-10}$alkyl, C(S)OC$_{2-10}$alkenyl, C(S)OC$_{2-10}$alkynyl, C(S)O-aryl, C(S)O(A)$_q R_{11}$, S(O)$_t$H, S(O)$_t C_{1-10}$alkyl, S(O)$_t C_{2-10}$alkenyl, S(O)$_t C_{2-10}$alkynyl, S(O)$_t$-aryl, S(O)$_t$(A)$_q R_{11}$, [C(O)CH($R_{14}$)NH]$_s$—H, [C(O)CH($R_{14}$)NH]$_s$—C$_{1-10}$alkyl, [C(O)CH($R_{14}$)NH]$_s$—C$_{2-10}$alkenyl, [C(O)CH($R_{14}$)NH]$_s$—C$_{2-10}$alkynyl, [C(O)CH($R_{14}$)NH]$_s$-aryl, [C(O)CH($R_{14}$)NH]$_s$-(A)$_q R_{11}$ and [sugar]$_s$;

Each $R_8$ is independently selected from $R_7$ and NHC(=N$R_{15}$)NH$_2$;

$R_9$ is selected from hydrogen and $C_{1-6}$alkyl;

$R_{10}$ is selected from $C_{1-6}$alkyl, NH$_2$, NH($C_{1-3}$alkyl), N($C_{1-3}$alkyl)$_2$, OH, OC$_{1-3}$alkyl, SH and SC$_{1-3}$alkyl;

$R_{11}$ is selected from OH, OC$_{1-6}$alkyl, OC$_{1-3}$alkyl-O—C$_{1-3}$alkyl, O-aryl, O-heterocyclyl, O[C(O)CH($R_{14}$)NH]$_s$H, [sugar]$_s$, SH, SC$_{1-6}$alkyl, SC$_{1-3}$alkyl-O—C$_{1-3}$alkyl, S-aryl, S-heterocyclyl, S[C(O)CH($R_{14}$)NH]$_s$H, halo, N($R_{15}$)$_2$, C(O)$R_{16}$, CN, C($R_{17}$)$_3$, aryl and heterocyclyl;

$R_{12}$ is selected from OH, SH, NH$_2$, halo, NO$_2$, C($R_{17}$)$_3$, OC($R_{17}$)$_3$ and CN;

Each $R_{13}$ is independently selected from hydrogen, $C_{1-6}$alkyl, $C_{2-6}$alkenyl, $C_{2-6}$alkynyl and (A)$_q R_{11}$;

$R_{14}$ is the characterising group of an amino acid;

Each $R_{15}$ is independently selected from hydrogen, $C_{1-6}$alkyl, $C_{1-3}$alkoxy$C_{1-3}$alkyl, aryl and heterocyclyl;

$R_{16}$ is selected from $C_{1-3}$alkyl, OH, $C_{1-3}$alkoxy, aryl, aryloxy, heterocyclyl and heterocyclyloxy;

Each $R_{17}$ is independently selected from hydrogen and halogen;

A is optionally substituted methylene wherein when n>1, any two adjacent A groups are optionally interrupted by —O—, —S— or —N($R_{15}$)—;

where n is 0 or an integer selected from 1 to 20;

m is 0 or an integer selected from 1 to 3;

p is an integer selected from 1 to 20;

q is an integer selected from 1 to 10 s is an integer selected from 1 to 5;

t is an integer selected from 1 or 2; and wherein each alkyl, alkenyl, alkynyl, aryl and heterocyclyl may be optionally substituted.

In a further aspect, the present invention provides a method of inhibiting cytokine or biological activity of MIF comprising contacting MIF with a cytokine or biological inhibiting amount of a compound of formula (I), or a pharmaceutically acceptable salt or prodrug thereof.

In another aspect, the invention provides a method of treating, preventing or diagnosing a disease or condition wherein MIF cytokine or biological activity is implicated comprising the administration of a treatment, prevention or diagnostic effective amount of a compound of formula (I) or a pharmaceutically acceptable salt or prodrug thereof to a subject in need thereof.

In a further aspect, there is provided the use of a compound of formula (I) or a pharmaceutically acceptable salt or prodrug thereof in the manufacture of a medicament for the treatment, prevention or diagnosis of a disease or condition wherein MIF cytokine or biological activity is implicated.

In particular, the invention provides a method of treating, diagnosing or preventing autoimmune diseases, tumours, or chronic or acute inflammatory diseases, including a disease or condition selected from the group comprising:

rheumatic diseases (including but not limited to rheumatoid arthritis, osteoarthritis, psoriatic arthritis) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, polymyalgia rheumatica;

connective tissue diseases (including but not limited to systemic lupus erythematosus, systemic sclerosis, polymyositis, dermatomyositis, Sjögren's syndrome);

vasculitides (including but not limited to polyarteritis nodosa, Wegener's granulomatosis, Churg-Strauss syndrome);

inflammatory conditions including consequences of trauma or ischaemia, sarcoidosis;

vascular diseases including atherosclerotic vascular disease, atherosclerosis, and vascular occlusive disease (including but not limited to atherosclerosis, ischaemic heart disease, myocardial infarction, stroke, peripheral vascular disease), and vascular stent restenosis;

ocular diseases including uveitis, corneal disease, iritis, iridocyclitis, cataracts; autoimmune diseases (including but not limited to diabetes mellitus, thyroiditis, myasthenia gravis, sclerosing cholangitis, primary biliary cirrhosis);

pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome);

cancers whether primary or metastatic (including but not limited to prostate cancer, colon cancer, lymphoma, lung cancer, melanoma, multiple myeloma, breast cancer, stomach cancer, leukaemia, cervical cancer and metastatic cancer);

renal diseases including glomerulonephritis, interstitial nephritis;

disorders of the hypothalamic-pituitary-adrenal axis;

nervous system disorders including multiple sclerosis, Alzheimer's disease;

diseases characterised by modified angiogenesis (eg diabetic retinopathy, rheumatoid arthritis, cancer), endometrial function (menstruation, implantation, endometriosis);

complications of infective disorders including endotoxic (septic) shock, exotoxic (septic) shock, infective (true septic) shock, malarial complications, other complications of infection, pelvic inflammatory disease;

transplant rejection, graft-versus-host disease;

allergic diseases including allergies, atopic diseases, allergic rhinitis;

bone diseases (eg osteoporosis, Paget's disease);

skin diseases including psoriasis, atopic dermatitis, UV(B)-induced dermal cell activation (eg sunburn, skin cancer);

complications of diabetes mellitus, pain, testicular dysfunctions and wound healing, gastrointestinal diseases including inflammatory bowel disease (including but not limited to ulcerative colitis, Crohn's disease), peptic ulceration, gastritis, oesophagitis, liver disease (including but not limited to cirrhosis, hepatitis);

comprising the administration of a treatment, diagnosis or prevention effective amount of a compound of Formula (I) or a pharmaceutically acceptable salt or prodrug thereof to a subject in need thereof.

Preferably, the disease or condition is selected from the group consisting of rheumatoid arthritis, systemic lupus erythematosus, ulcerative colitis, Crohn's disease, multiple sclerosis, psoriasis, uveitis, atherosclerotic vascular disease, asthma and chronic obstructive pulmonary disease.

A further aspect of the invention provides for the use of a compound of Formula (I) or a pharmaceutically acceptable salt or prodrug thereof in the manufacture of a medicament for the treatment of a disease or condition as above.

A further aspect of the invention provides a pharmaceutical composition comprising a compound of formula (I) and a pharmaceutically acceptable carrier, diluent or excipient.

In another aspect, the invention provides a method of treating or preventing a disease or condition wherein MIF cytokine or biological activity is implicated comprising:
administering to a mammal a compound of formula (I) and a second therapeutic agent.

In another aspect, the present invention provides a method of prophylaxis or treatment of a disease or condition for which treatment with a glucocorticoid is indicated, said method comprising:
administering to a mammal a glucocorticoid and a compound of formula (I).

In yet another aspect, the present invention provides a method of treating steroid-resistant diseases comprising:
administering to a mammal a glucocorticoid and a compound of formula (I).

In a further aspect, the present invention provides a method of enhancing the effect of a glucocorticoid in mammals comprising administering a compound of formula (I) simultaneously, separately or sequentially with said glucocorticoid.

In yet a further aspect, the present invention provides a pharmaceutical composition comprising a glucocorticoid and a compound of formula (I).

In a further aspect of the invention there is provided a use of a glucocorticoid in the manufacture of a medicament for administration with a compound of formula (I) for the treatment or prophylaxis of a disease or condition for which treatment with a glucocorticoid is indicated.

In yet a further aspect of the invention there is provided a use of a compound of formula (I) in the manufacture of a medicament for administration with a glucocorticoid for the treatment or prophylaxis of a disease or condition for which treatment of a glucocorticoid is indicated.

In yet a further aspect of the invention there is provided a use of a glucocorticoid and a compound of formula (I) in the manufacture of a medicament for the treatment or prophylaxis of a disease or condition for which treatment with a glucocorticoid is indicated.

In preferred embodiments, the compounds of Formula (I) or a pharmaceutically acceptable salt or prodrug thereof are used to treat or prevent a disease or condition, particularly in a human subject.

DETAILED DESCRIPTION OF THE INVENTION

Figure 1:
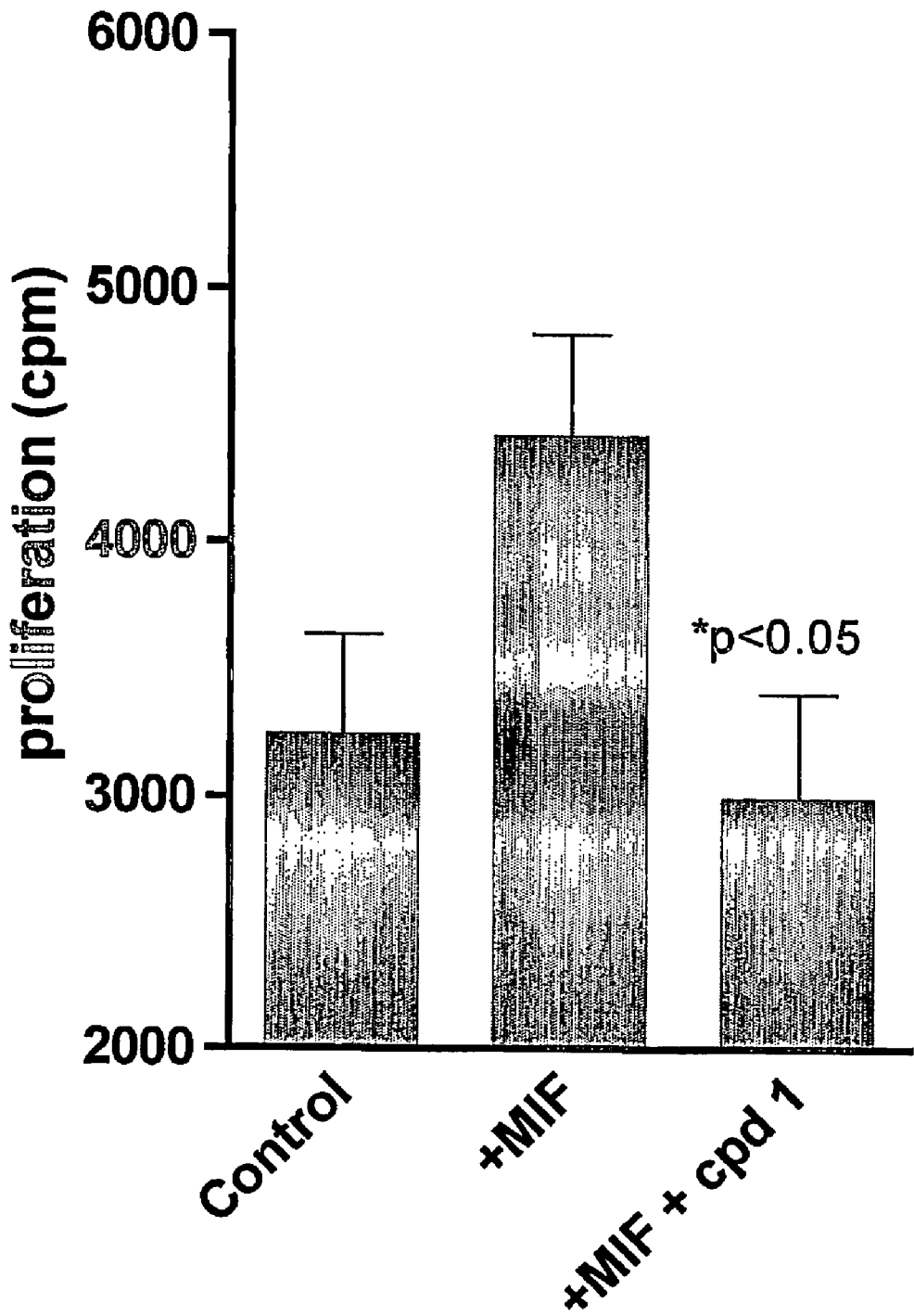
FIG. 1: graphically depicts inhibition of MIF-induced proliferation of S112 human fibroblasts by 2-(2-hydroxyethoxy)-2-(4-hydroxy-3-methylphenyl)-1,3-dioxolane (Compound 1).

As used herein, the term "alkyl" refers to monovalent straight, branched or, where appropriate, cyclic aliphatic radicals, having 1 to 3, 1 to 6, 1 to 10 or 1 to 20 carbon atoms, e.g. methyl, ethyl, n-propyl, iso-propyl, cyclopropyl, n-butyl, sec-butyl, t-butyl and cyclobutyl, n-pentyl, 1-methylbutyl, 2-methylbutyl, 3-methylbutyl, cyclopentyl, n-hexyl, 1- 2- 3- or 4-methylpentyl, 1- 2- or 3-ethylbutyl, 1 or 2-propylpropyl or cyclohexyl.

An alkyl group may be optionally substituted one or more times by halo (eg chloro, fluoro or bromo), CN, $NO_2$, $CO_2H$, $CO_2C_{1-6}$alkyl, $CO_2NH_2$, $CO_2NH(C_{1-6}$alkyl), $CO_2N(C_{1-6}$alkyl)$_2$, OH, alkoxy, acyl, acetyl, halomethyl, trifluoromethyl, benzyloxy, phenoxy, $NH_2$, $NH(C_{1-6}$alkyl) or N ($C_{1-6}$alkyl)$_2$. A preferred optional substituent is a polar substituent. Examples of alkoxy include methoxy, ethoxy, n-propoxy, iso-propoxy, cyclopropoxy, and butoxy (n-, sec- t- and cyclo) pentoxy and hexyloxy. The "alkyl" portion of an alkoxy group may be substituted as described above.

As used herein, the term "alkenyl" refers to straight, branched, or where appropriate, cyclic carbon containing radicals having one or more double bonds between carbon atoms. Examples of such radicals include vinyl, allyl, butenyl, or longer carbon chains such as those derived from palmitoleic, oleic, linoleic, linolenic or arachidonic acids. An alkenyl group may be optionally substituted one or more times by halo (eg chloro, fluoro or bromo), CN, $NO_2$, $CO_2H$, $CO_2C_{1-6}$alkyl, $CO_2NH_2$, $CO_2NH(C_{1-6}$alkyl), $CO_2N(C_{1-6}$alkyl)$_2$, OH, alkoxy, acyl, acetyl, halomethyl, trifluoromethyl, benzyloxy, phenoxy, $NH_2$, $NH(C_{1-6}$alkyl) or $N(C_{1-6}$alkyl)$_2$. A preferred optional substituent is a polar substituent.

As used herein, the term "alkynyl" refers to straight or branched carbon containing radicals having one or more triple bonds between carbon atoms. Examples of such radicals include propargyl, butynyl and hexynyl. An alkynyl group may be optionally substituted one or more times by halo (eg chloro, fluoro or bromo), CN, $NO_2$, $CO_2H$, $CO_2C_{1-6}$alkyl, $CO_2NH_2$, $CO_2NH(C_{1-6}$alkyl), $CO_2N(C_{1-6}$alkyl)$_2$, OH, alkoxy, acyl, acetyl, halomethyl, trifluoromethyl, benzyloxy, phenoxy, $NH_2$, $NH(C_{1-6}$alkyl) or $N(C_{1-6}$alkyl)$_2$. A preferred optional substituent is a polar substituent.

Examples of suitable NH(alkyl) and N(alkyl)$_2$ include methylamino, ethylamino, isopropylamino, dimethylamino, n-propylamino, diethylamino and di-isopropylamino.

The term "halogen" (or "halo") refers to fluorine (fluoro), chlorine (chloro), bromine (bromo) or iodine (iodo).

The term "sugar" refers to a pyranosyl or furanosyl moiety such as those derived from glucose, galactose, mannose, allose, altrose, glucose, idose, talose, ribose, arabinose or xylose. Derivatives of such sugars include deoxy or amino pyranosyl or furanosyl sugar derivatives. Each sugar moiety is incorporated into the compound of formula (I) through a hydroxy group of the sugar moiety.

As used herein, "the characterising group of an amino acid" refers to the substituent at $C_2$ of a natural or unnatural amino acid and which defines the amino acid. For example, methyl is the characterising group of alanine, phenylmethyl is the characterising group of phenylalanine, hydroxymethyl is the characterising group of serine, hydroxyethyl is the characterising group of homoserine and n-propyl is the characterising group of norvaline.

An aryl group, as used herein, refers to $C_6$-$C_{10}$ aryl groups such as phenyl or naphthalene. Aryl groups may be optionally substituted one or more times by halo (eg, chloro, fluoro or bromo), CN, $NO_2$, $CO_2H$, $CO_2C_{1-6}$alkyl, $CO_2NH_2$, $CO_2NH(C_{1-6}$alkyl), $CO_2N(C_{1-6}$alkyl)$_2$, OH, alkoxy, acyl, acetyl, halomethyl, trifluoromethyl, benzyloxy, phenoxy, $NH_2$, $NH(C_{1-6}$alkyl) or $N(C_{1-6}$alkyl)$_2$.

As used herein, the term "heterocyclyl" refers to a cyclic, aliphatic or aromatic radical containing at least one heteroatom independently selected from O, N or S. Examples of suitable heterocyclyl groups include furyl, dioxolanyl, dioxanyl, dithianyl, dithiolanyl, pyridinyl, pyrimidinyl, pyrazolyl, piperidinyl, pyrrolyl, thyaphenyl, oxazolyl, imidazolyl, thiazolyl, isoxazolyl, isothiazolyl, quinolyl, isoquinolyl, indolyl, benzofuranyl, benzothiophenyl, triazolyl, tetrazolyl, oxadiazolyl and purinyl. Heterocyclyl groups may be optionally substituted one or more times by halo (eg, chloro, fluoro or bromo), CN, $NO_2$, $CO_2H$, $CO_2C_{1-6}$alkyl, $CO_2NH_2$, $CO_2NH(C_{1-6}$alkyl), $CO_2N(C_{1-6}$alkyl)$_2$, OH, alkoxy, acyl, acetyl, halomethyl, trifluoromethyl, benzyloxy, phenoxy, $NH_2$, $NH(C_{1-6}$alkyl) or $N(C_{1-6}$alkyl)$_2$.

Each A is an unsubstituted methylene group (—$CH_2$—) or an optionally substituted methylene group where one or two of the hydrogen atoms of the methylene group may be replaced by a substituent, such as halo (eg. chloro, fluoro or bromo), CN, $NO_2$, $CO_2H$, $CO_2C_{1-6}$alkyl, $CO_2NH_2$, $CO_2NH(C_{1-6}$alkyl), $CO_2N(C_{1-6}$alkyl)$_2$, OH, alkoxy, acyl, acetyl, halomethyl, trifluoromethyl, benzyloxy, phenoxy, $NH_2$, $NH(C_{1-6}$alkyl) or $N(C_{1-6}$alkyl)$_2$. $(A)_n$ may therefore form an optionally substituted methylene group, when n is 1, or an optionally substituted alkylene group when n is greater than 1. Alternatively, when two or more A groups appear in adjacent positions, they are optionally interrupted by —O—, —S— or —N($R_{15}$)—. $(A)_n$ may therefore form, for example, an optionally substituted ether or polyether.

In a first aspect, the present invention provides a compound of formula (I), or a pharmaceutically acceptable salt or prodrug thereof

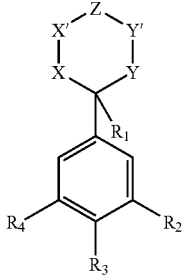

(I)

wherein X and X' are independently selected from —C(R$_5$)$_2$—, —O—, —S—, —N(R$_5$)—, or taken together form —C(R$_5$)=C(R$_5$)—, —C(R$_5$)=N—, —N=C(R$_5$)—, —N(R$_5$)—N(R$_5$)— or —N=N—;

Y and Y' are independently selected from —C(R$_5$)$_2$—, —O—, —S—, —N(R$_5$)—, or taken together form —C(R$_5$)=C(R$_5$)—, —C(R$_5$)=N—, —N=C(R$_5$)—, —N(R$_5$)—N(R$_5$)— or —N=N—;

Z is —C(R$_5$)$_2$—, —O—, —S— or —N(R$_5$)—, or forms a covalent single or double bond between X' and Y', or Z together with X' or Y' forms —C(R$_5$)=C(R$_5$)—, —C(R$_5$)=N—, —N=C(R$_5$)—, —N(R$_5$)—N(R$_5$)— or —N=N—;

wherein when Z is —O—, —S— or —N(R$_5$)—, X' and Y' are —C(R$_5$)$_2$—;

when X is —O—, —S— or —N(R$_5$)—, X' is —C(R$_5$)$_2$—;

when Y is —O—, —S— or —N(R$_5$)—, Y' is —C(R$_5$)$_2$—; or

X or Y together with the carbon atom bearing the phenyl group form a double bond wherein which ever of X or Y forms part of the double bond is selected from —C(R$_5$)— and —N—;

R$_1$ is selected from hydrogen, C$_{1-20}$alkyl, C$_{2-20}$alkenyl, C$_{2-20}$alkynyl, (A)$_n$C(O)R$_6$, (A)$_n$C(S)R$_6$, (A)$_n$S(O)R$_6$, (A)$_n$S(O)$_2$R$_6$, (A)$_n$OR$_7$, (A)$_n$SR$_7$, (A)$_n$N(R$_8$), (A)$_n$C(=NR$_9$)R$_{10}$ and (A)$_n$R$_{11}$, or when X or Y together with the carbon atom bearing the phenyl group form a double bond, R$_1$ is absent;

R$_2$ and R$_4$ are independently selected from hydrogen, C$_{1-3}$alkyl and (A)$_m$R$_{12}$;

R$_3$ is selected from C$_{1-3}$alkyl, (A)$_m$R$_{12}$, (A)$_m$aryl and (A)$_m$heterocyclyl;

R$_5$ is selected from hydrogen, C$_{1-20}$alkyl, C$_{2-20}$alkenyl, C$_{2-20}$alkynyl, (A)$_n$C(O)R$_6$, (A)$_n$C(S)R$_6$, (A)$_n$S(O)R$_6$, (A)$_n$S(O)$_2$R$_6$, (A)$_n$OR$_7$, (A)$_n$SR$_7$, (A)$_p$N(R$_8$), (A)$_n$C(=NR$_9$)R$_{10}$ and (A)$_n$R$_{11}$;

R$_6$ is selected from hydrogen, C$_{1-20}$alkyl, C$_{2-20}$alkenyl, C$_{2-20}$alkynyl, OH, OC$_{1-10}$alkyl, OC$_{2-10}$alkenyl, OC$_{2-10}$alkynyl, O(A)$_q$R$_{11}$, SH, SC$_{1-10}$alkyl, SC$_{2-10}$alkenyl, SC$_{2-10}$alkynyl, S(A)$_q$R$_{11}$, N(R$_{13}$)$_2$, [NH—CH(R$_{14}$)C(O)]$_s$—OH, [NH—CH(R$_{14}$)C(O)]$_s$—OC$_{1-3}$alkyl, [sugar]$_s$ and (A)$_q$R$_{11}$;

R$_7$ is selected from hydrogen, C$_{1-20}$alkyl, C$_{2-20}$alkenyl, C$_{2-20}$alkynyl, (A)$_q$R$_{11}$, C(O)H, C(O)C$_{1-10}$alkyl, C(O)C$_{2-10}$alkenyl, C(O)C$_{2-10}$alkynyl, C(O)-aryl, C(O)(A)$_q$R$_{11}$, C(O)$_2$H, C(O)$_2$C$_{1-10}$alkyl, C(O)$_2$C$_{2-10}$alkenyl, C(O)$_2$C$_{2-10}$alkynyl, C(O)$_2$-aryl, C(O)$_2$(A)$_q$R$_{11}$, C(S)H, C(S)C$_{1-10}$alkyl, C(S)C$_{2-10}$alkenyl, C(S)C$_{2-10}$alkynyl, C(S)-aryl, C(S)(A)$_q$R$_{11}$, C(S)OH, C(S)OC$_{1-10}$alkyl, C(S)OC$_{2-10}$alkenyl, C(S)OC$_{2-10}$alkynyl, C(S)O-aryl, C(S)O(A)$_q$R$_{11}$, S(O)$_t$H, S(O)$_t$C$_{1-10}$alkyl, S(O)$_t$C$_{2-10}$alkenyl, S(O)$_t$C$_{2-10}$alkynyl, S(O)$_t$-aryl, S(O)$_t$(A)$_q$R$_{11}$, [C(O)CH(R$_{14}$)NH]$_s$—H, [C(O)CH(R$_{14}$)NH]$_s$—C$_{1-10}$alkyl, [C(O)CH(R$_{14}$)NH]$_s$—C$_{2-10}$alkenyl, [C(O)CH(R$_{14}$)NH]$_s$—C$_{2-10}$alkynyl, [C(O)CH(R$_{14}$)NH]$_s$-aryl, [C(O)CH(R$_{14}$)NH]$_s$-(A)$_q$R$_{11}$ and [sugar]$_s$;

Each R$_8$ is independently selected from R$_7$ and NHC(=NR$_{15}$)NH$_2$;

R$_9$ is selected from hydrogen and C$_{1-6}$alkyl;

R$_{10}$ is selected from C$_{1-6}$alkyl, NH$_2$, NH(C$_{1-3}$alkyl), N(C$_{1-3}$alkyl)$_2$, OH, OC$_{1-3}$alkyl, SH and SC$_{1-3}$alkyl;

R$_{11}$ is selected from OH, OC$_{1-6}$alkyl, OC$_{1-3}$alkyl-O—C$_{1-3}$alkyl, O-aryl, O-heterocyclyl, O[C(O)CH(R$_{14}$)NH]$_s$H, [sugar]$_s$, SH, SC$_{1-6}$alkyl, SC$_{1-3}$alkyl-O—C$_{1-3}$alkyl, S-aryl, S-heterocyclyl, S[C(O)CH(R$_{14}$)NH]$_s$H, halo, N(R$_{15}$)$_2$, C(O)R$_{16}$, CN, C(R$_{17}$)$_3$, aryl and heterocyclyl;

R$_{12}$ is selected from OH, SH, NH$_2$, halo, NO$_2$, C(R$_{17}$)$_3$, OC(R$_{17}$)$_3$ and CN;

Each R$_{13}$ is independently selected from hydrogen, C$_{1-6}$alkyl, C$_{2-6}$alkenyl, C$_{2-6}$alkynyl and (A)$_q$R$_{11}$;

R$_{14}$ is the characterising group of an amino acid;

Each R$_{15}$ is independently selected from hydrogen, C$_{1-6}$alkyl, C$_{1-3}$alkoxyC$_{1-3}$alkyl, aryl and heterocyclyl;

R$_{16}$ is selected from C$_{1-3}$alkyl, OH, C$_{1-3}$alkoxy, aryl, aryloxy, heterocyclyl and heterocyclyloxy;

Each R$_{17}$ is independently selected from hydrogen and halogen;

A is optionally substituted methylene wherein when n>1, any two adjacent A groups are optionally interrupted by —O—, —S— or —N(R$_{15}$)—;

where n is 0 or an integer selected from 1 to 20;

m is 0 or an integer selected from 1 to 3;

p is an integer selected from 1 to 20;

q is an integer selected from 1 to 10;

s is an integer selected from 1 to 5;

t is an integer selected from 1 or 2; and wherein each alkyl, alkenyl, alkynyl, aryl and heterocyclyl may be optionally substituted.

In another aspect, the compound of the invention is a compound of formula (II), or a pharmaceutically acceptable salt or prodrug thereof

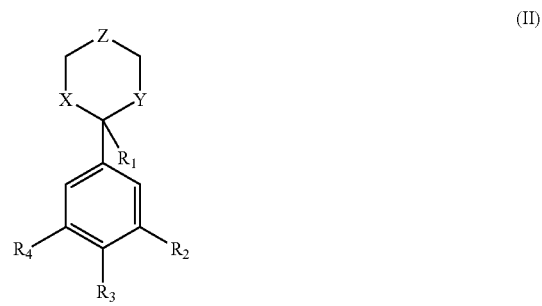

(II)

wherein X and Y are independently selected from —O—, —S—, —N(R$_5$)— and —C(R$_5$)$_2$—;

Z is —C(R$_5$)$_2$— or is a covalent bond between adjacent methylene groups;

$R_1$ is selected from hydrogen, $C_{1-20}$alkyl, $C_{2-20}$alkenyl, $C_{2-20}$alkynyl, $(A)_nC(O)R_6$, $(A)_nC(S)R_6$, $(A)_nS(O)R_6$, $(A)_nS(O)_2R_6$, $(A)_nOR_7$, $(A)_nSR_7$, $(A)_nN(R_8)$, $(A)_nC(=NR_9)R_{10}$ and $(A)_nR_{11}$;

$R_2$ and $R_4$ are independently selected from hydrogen, $C_{1-3}$alkyl and $(A)_mR_{12}$;

$R_3$ is selected from $C_{1-3}$alkyl, $(A)_mR_{12}$, $(A)_m$aryl and $(A)_m$heterocyclyl;

$R_5$ is selected from hydrogen, $C_{1-20}$alkyl, $C_{2-20}$alkenyl, $C_{2-20}$alkynyl, $(A)_nC(O)R_6$, $(A)_nC(S)R_6$, $(A)_nS(O)R_6$, $(A)_nS(O)_2R_6$, $(A)_nOR_7$, $(A)_nSR_7$, $(A)_pN(R_8)$, $(A)_nC(=NR_9)R_{10}$ and $(A)_nR_{11}$;

$R_6$ is selected from hydrogen, $C_{1-20}$alkyl, $C_{2-20}$alkenyl, $C_{2-20}$alkynyl, OH, $OC_{1-10}$alkyl, $OC_{2-10}$alkenyl, $OC_{2-10}$alkynyl, $O(A)_qR_{11}$, SH, $SC_{1-10}$alkyl, $SC_{2-10}$alkenyl, $SC_{2-10}$alkynyl, $S(A)_qR_{11}$, $N(R_{13})_2$, $[NH-CH(R_{14})C(O)]_s$—OH, $[NH-CH(R_{14})C(O)]_s$—$OC_{1-3}$alkyl, $[sugar]_s$ and $(A)_qR_{11}$;

$R_7$ is selected from hydrogen, $C_{1-20}$alkyl, $C_{2-20}$alkenyl, $C_{2-20}$alkynyl, $(A)_qR_{11}$, C(O)H, $C(O)C_{1-10}$alkyl, $C(O)C_{2-10}$alkenyl, $C(O)C_{2-10}$alkynyl, C(O)-aryl, $C(O)(A)_qR_{11}$, $C(O)_2H$, $C(O)_2C_{1-10}$alkyl, $C(O)_2C_{2-10}$alkenyl, $C(O)_2C_{2-10}$alkynyl, $C(O)_2$-aryl, $C(O)_2(A)_qR_{11}$, C(S)H, $C(S)C_{1-10}$alkyl, $C(S)C_{2-10}$alkenyl, $C(S)C_{2-10}$alkynyl, C(S)-aryl, $C(S)(A)_qR_{11}$, C(S)OH, $C(S)OC_{1-10}$alkyl, $C(S)OC_{2-10}$alkenyl, $C(S)OC_{2-10}$alkynyl, C(S)O-aryl, $C(S)O(A)_qR_{11}$, $S(O)_tH$, $S(O)_tC_{1-10}$alkyl, $S(O)_tC_{2-10}$alkenyl, $S(O)_tC_{2-10}$alkynyl, $S(O)_t$-aryl, $S(O)_t(A)_qR_{11}$, $[C(O)CH(R_{14})NH]_s$—H, $[C(O)CH(R_{14})NH]_s$—$C_{1-10}$alkyl, $[C(O)CH(R_{14})NH]_s$—$C_{2-10}$alkenyl, $[C(O)CH(R_{14})NH]_s$—$C_{2-10}$alkynyl, $[C(O)CH(R_{14})NH]_s$-aryl, $[C(O)CH(R_{14})NH]_s$-$(A)_qR_{11}$ and $[sugar]_s$;

Each $R_8$ is independently selected from $R_7$ and $NHC(=NR_{15})NH_2$;

$R_9$ is selected from hydrogen and $C_{1-6}$alkyl;

$R_{10}$ is selected from $C_{1-6}$alkyl, $NH_2$, $NH(C_{1-3}$alkyl), $N(C_{1-3}$alkyl$)_2$, OH, $OC_{1-3}$alkyl, SH and $SC_{1-3}$alkyl;

$R_{11}$ is selected from OH, $OC_{1-6}$alkyl, $OC_{1-3}$alkyl-O—$C_{1-3}$alkyl, O-aryl, O-heterocyclyl, $O[C(O)CH(R_{14})NH]_sH$, $[sugar]_s$, SH, $SC_{1-6}$alkyl, $SC_{1-3}$alkyl-O—$C_{1-3}$alkyl, S-aryl, S-heterocyclyl, $S[C(O)CH(R_{14})NH]_sH$, halo, $N(R_{15})_2$, $C(O)R_{16}$, CN, $C(R_{17})_3$, aryl and heterocyclyl;

$R_{12}$ is selected from OH, SH, $NH_2$, halo, $NO_2$, $C(R_{17})_3$, $OC(R_{17})_3$ and CN;

Each $R_{13}$ is independently selected from hydrogen, $C_{1-6}$alkyl, $C_{2-6}$alkenyl, $C_{2-6}$alkynyl and $(A)_qR_{11}$;

$R_{14}$ is the characterising group of an amino acid;

Each $R_{15}$ is independently selected from hydrogen, $C_{1-6}$alkyl, $C_{1-3}$alkoxy$C_{1-3}$alkyl, aryl and heterocyclyl;

$R_{16}$ is selected from $C_{1-3}$alkyl, OH, $C_{1-3}$alkoxy, aryl, aryloxy, heterocyclyl and heterocyclyloxy;

Each $R_{17}$ is independently selected from hydrogen and halogen;

A is optionally substituted methylene wherein when n>1, any two adjacent A groups are optionally interrupted by —O—, —S— or —N(R_{15})—;

where n is 0 or an integer selected from 1 to 20;

m is 0 or an integer selected from 1 to 3;

p is an integer selected from 1 to 20;

q is an integer selected from 1 to 10 s is an integer selected from 1 to 5;

t is an integer selected from 1 or 2; and wherein each alkyl, alkenyl, alkynyl, aryl and heterocyclyl may be optionally substituted.

In a preferred embodiment one or more of the following definitions apply:

X is —O—, —S—, —NH— or —CH_2—;

Y is —O—, —S— or —NR_5—;

Z forms a covalent bond between adjacent methylene groups;

$R_1$ is selected from $C_{1-20}$alkyl, $C_{1-20}$alkenyl, O-$(A)_q$O—$C_{1-6}$alkyl, O-$(A)_q$-heterocyclyl, O-$(A)_q$-sugar, O-$(A)_q$O$[C(O)CH(R_{14})NH]_s$—H, $(A)_n$OH, $(A)_n$O$C_{1-20}$alkyl, $(A)_n$O$C_{1-20}$alkenyl, $(A)_n$OC(O)$C_{1-20}$alkyl, $(A)_n$OC(O)$C_{1-20}$alkenyl, $(A)_n$OC(O)aryl, $(A)_n$O$[C(O)CH(R_{14})NH]_s$—H, $(A)_n$O$[sugar]_s$, $(A)_n$NH$C_{1-20}$alkyl, $(A)_n$N$(C_{1-20}$alkyl$)_2$, $(A)_n$NH$C_{1-20}$alkenyl, $(A)_n$N$(C_{1-20}$alkenyl$)_2$, $(A)_n$NHC(O)$C_{1-20}$alkyl, $(A)_n$NHC(O)$C_{1-20}$alkenyl, $(A)_n$NHC(O)aryl, $(A)_n$NH$[C(O)CH(R_{14})NH]_s$—H, $(A)_n$NH-$[sugar]_s$, $(A)_n$SO$_3$H, $(A)_n$SO$_3C_{1-20}$alkyl, $(A)_n$SO$_3C_{1-20}$alkenyl, $(A)_n$C(O)$C_{1-20}$alkyl, $(A)_n$C(O)$C_{1-20}$alkenyl, $(A)_n$CO$_2$H, $(A)_n$CO$_2C_{1-20}$alkyl, $(A)_n$CO$_2C_{1-20}$alkenyl, $(A)_n$C(O)NH$C_{1-20}$alkyl, $(A)_n$C(O)N$(C_{1-20}$alkyl$)_2$, $(A)_n$C(O)NH$C_{1-20}$alkenyl, $(A)_n$C(O)N$(C_{1-20}$alkenyl$)_2$, $(A)_n$C(O)$[NHCH(R_{14})C(O)]_s$—OH, $(A)_n$C(O)$[sugar]_s$; wherein A is methylene optionally substituted one or two times with a group that is independently selected from $C_{1-6}$alkyl, $C_{2-6}$alkenyl, $C_{2-6}$alkynyl, halogen, OH, $OC_{1-6}$ alkyl, $CO_2H$, $CO_2C_{1-3}$alkyl, $NH_2$, $NHC_{1-3}$alkyl, —N$(C_{1-3}$ alkyl$)_2$, CN, $NO_2$, aryl or heterocyclyl; $R_{14}$ is the characterising group of an amino acid, n is 0 or an integer from 1 to 20 and s is an integer from 1 to 5;

$R_2$ is hydrogen, $C_{1-3}$alkyl, OH, SH, $NH_2$, —$NO_2$, $CF_3$, halo or —CN;

$R_3$ is hydrogen, $C_1$-$C_3$alkyl, —$(CH_2)_mNH_2$, —$(CH_2)_m$—OH, —$(CH_2)_m$—$CF_3$, —$(CH_2)_m$—SH or a 5 or 6 membered heterocyclic group, wherein m is 0 or an integer from 1 to 3;

$R_4$ is hydrogen, $C_{1-3}$alkyl, OH, SH, $NH_2$, $NO_2$, $CF_3$, halo or CN;

A is unsubstituted methylene or mono-substituted methylene.

In certain preferred forms of the invention, the compounds of Formula (II) include:

(II)

wherein

X is —O—, —S—, —NH—;

Y is —O—, —S— or —N(R_5)—,

Z forms a covalent bond between adjacent methylene groups;

$R_1$ is $C_1$-$C_{20}$alkyl, $C_2$-$C_{20}$alkenyl, $C_2$-$C_{20}$alkynyl, $(A)_nC(O)R_6$, $-(A)_nC(S)R_6$, $-(A)_nS(O)R_6$, $-(A)_nS(O)_2R_6$, $-(A)_nOR_7$, $-(A)_nSR_7$, $-(A)_nN(R_8)_2$, $(A)_nC(=NR_9)R_{10}$ or $(A)_nR_{11}$ where n, $R_6$, $R_7$, $R_8$, $R_9$, $R_{10}$ and $R_{11}$ are defined above;

$R_2$ is hydrogen, methyl, OH, $OCH_3$, SH, $NH_2$, $NO_2$, $CF_3$, halo or CN;

$R_3$ is $C_{1-3}$alkyl, $-(CH_2)_mNH_2$, $-(CH_2)_m-OH$, $-(CH_2)_mSH$ or heterocyclyl where m is defined above;

$R_4$ is hydrogen, methyl, OH, $OCH_3$, SH, $NH_2$, $NO_2$, $CF_3$, $CF_3$, halo or CN.

More preferably the compounds of formula (II) comprise

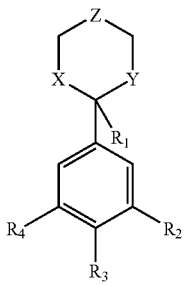

(II)

wherein

X is —O— or NH;

Y is —O— or —N($R_{18}$)— where $R_{18}$ is selected from hydrogen, $C_{1-20}$alkyl, $C_{1-20}$alkenyl, $C_{1-20}$alkenyl, $C_{1-20}$alkynyl and $(CH_2)_nR_{11}$ where $R_{11}$ and n are defined above;

Z forms a covalent bond between adjacent methylene groups;

$R_1$ is as defined for $R_1$ above;

$R_2$ is hydrogen, halomethyl, OH, $OCH_3$, SH, $NH_2$, $NO_2$ or CN;

$R_3$ is hydrogen, $C_{1-3}$alkyl, $(CH_2)_mNH_2$, $(CH_2)_mOH$ or $(CH_2)_mCF_3$ or heterocyclyl where m is defined above;

$R_4$ is hydrogen, methyl, OH, $OCH_3$, SH, $NH_2$, $NO_2$ or CN.

More preferably, the compounds of Formula (I) are heterocyclic compounds having the formula (III)

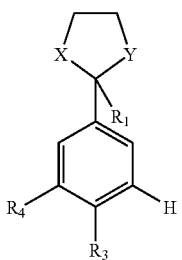

(III)

wherein

X is —O— or —NH—;

Y is —O— or —N($R_{18}$)— where $R_{18}$ is defined above;

$R_1$ is as defined for $R_1$ above;

$R_3$ is hydrogen, $NH_2$, OH;

$R_4$ is hydrogen, methyl, $OCH_3$, or OH.

In a preferred embodiment R1 is selected from $(A)_nOR_7$ where n is 0 and A and $R_7$ are defined above.

Further preferred embodiments include:

A compound of formula (I) wherein X is —S; Y is —N($R_5$)—; X' is —C($R_5$)$_2$—; Y' is —C($R_5$)$_2$—; Z forms a covalent bond between X' and Y'. Preferably, Y is —NH—; X' is —CH$_2$—; Y' is —CH$_2$—; $R_1$ is H.

A compound of formula (I) wherein X and Y are each —O—; X' and Y' are each —C($R_5$)$_2$—; Z forms a covalent bond between X' and Y'. Preferably, X' and Y' are each —CH$_2$—; $R_1$ is H.

A compound of formula (I) wherein X and X' taken together form —C($R_5$)=N—; Y is —C($R_5$)— and taken together with the carbon atom bearing the phenyl group forms a double bond; Y' is —N($R_5$)—; Z forms a covalent bond between X' and Y'. Preferably, Y is —CH—; X is —CH—.

A compound of formula (I) wherein X and X' taken together form —C($R_5$)=N—; Z together with Y' forms —C($R_5$)=C($R_5$)—; Y is —C($R_5$)— and together with the carbon atom bearing the phenyl group forms a double bond. Preferably, X is —C(OCH$_3$); Z together with Y' forms —C(OCH$_3$)=CH—; Y is —CH—.

A compound of formula (I) wherein X' is —C($R_5$)$_2$—; Y' is —C($R_5$)$_2$—; Z is —C($R_5$)$_2$—; X and Y are each —O—. Preferably, X', Y' and Z are each —CH$_2$—; $R_1$ is H.

A compound of formula (I) wherein X and Y are each —S—; X' and Y' are each —C($R_5$)$_2$—; Z forms a covalent bond between X' and Y'. Preferably, X' and Y' are each —CH$_2$—; $R_1$ is H.

A compound of formula (I) wherein X is —S—; Y is —O—; X' and Y' are each —C($R_5$)$_2$—; Z forms a covalent bond between X' and Y'. Preferably, X' and Y' are each —CH$_2$—.

A compound of formula (I) wherein X and X' taken together form —C($R_5$)=C($R_5$)—; Z together with Y' forms —C($R_5$)=C($R_5$)—; Y is —C($R_5$)— and together with the carbon atom bearing the phenyl group forms a double bond. Preferably, X and X' taken together form —CH=CH—; Z together with Y forms —H=CH—; Y is —CH—.

A compound of formula (I) wherein Y is —N— and taken together with the carbon atom bearing the phenyl group forms a double bond; X is —O—; X' and Y' are each —C($R_5$)$_2$—; Z forms a covalent bond between X' and Y'. Preferably, X' and Y' are each —CH$_2$—.

A compound of formula (I) wherein X and Y are each —C($R_5$)$_2$—; X' and Y' are each —N($R_5$)—; Z is C($R_5$)$_2$.

A compound of formula (I) wherein X is —O—; Y' is —N($R_5$)—; X' and Y are each —C($R_5$)$_2$—.

A compound of formula (I) wherein X and X' are each —C($R_5$)$_2$—; Y is —N($R_5$)—, Y' is —C($R_5$)$_2$—; Z forms a covalent bond between X' and Y'.

A compound of formula (I) wherein X is —N($R_5$)—; X' is —C($R_5$)$_2$—; Y is —C($R_5$)$_2$—; Y' is —N($R_5$)—; Z forms a covalent bond between X' and Y'.

A compound of formula (I) wherein X and X' are each —C($R_5$)$_2$— Y is —C($R_5$)$_2$—; Y' is —N($R_5$)—; Z is —C($R_5$)$_2$—.

Preferred compounds of formula (I) include 2-(2-hydroxyethoxy)-2-(4-hydroxy-3-methylphenyl)-1,3-dioxolane; 2-(2-hydroxyethoxy)-2-(4-hydroxyphenyl)-1,3-dioxolane; 2-(2-hydroxyethoxy)-2-(3-bromo-4-hydroxy-5-methylphenyl)-1,3-dioxolane; 2-(4-Bromophenyl)-1,3-thiazolane; 2-(4-Methoxyphenyl)-1,3-thiazolane; 4-(1,3-Thiazolidin-2-yl)benzonitrile; 2-(4-Hydroxy-3-methoxyphenyl)-1,3- thiazolane; 2-(3,4-Dimethoxyphenyl)-1,3-thiazolane; Methyl 4-[2-(4-fluorophenyl)-1,3-dioxolan-2-yl]butanoate; 4-[2-(4-Fluorophenyl)-1,3-dioxolan-2-yl]butan-1-ol; 2-(4'-Bromophenyl)-2-butyl-1,3-dioxolane; 4-(4-Methoxyphenyl)-1-(3-methylbutyl)-1H-pyrazole; 1-(3-Methylbutyl)-4-(4-methylphenyl)-1H-pyrazole; 2,6-Dimethoxy-3-[4-(trifluoromethoxy)phenyl]pyridine); 2-[4-(2-Thienyl)phenyl]-1,3-thiazolane; 2-Ethyl-2-(4-methoxyphenyl)-1,3-dioxolane; 2-Hexyl-2-(4-methylphenyl)-1,3-dithiolane; 2-Methyl-2-(4-methylphenyl)-1,3-dithiolane; 2-Hexyl-2-(4-methylphenyl)-1,3-dioxolane; 2-(4-Chlorophenyl)-2-methyl-1,3-dioxane; 2-(4-Chlorophenyl)-2-methyl-1,3-dioxolane; 2-Methyl-2-(4-methylphenyl)-1,3-dioxane; 2-Methyl-2-(4-methylphenyl)-1,3-dioxolane; 2-(4-Chlorophenyl)-2-methyl-1,3-dithiolane; 2-(4-Nitrophenyl)-2-methyl-1,3-dioxolane; 2-(4-Nitrophenyl)-2-methyl-1,3-dioxane; 2-(4-Methoxyphenyl)-1,3-oxathiolane; 2-(3,4,5-Trimethoxyphenyl)-1,3-oxathiolane; 2-Methoxy-4-(1,3-oxathiolan-2-yl)phenol; 4-(1,3-Oxathiolan-2-yl)benzonitrile; 2-(4-Bromophenyl)-2-ethyl-1,3-oxathiolane; 4-(5-Methyl-1,3-oxathiolan-2-yl)benzonitrile; 2-(4-Thien-2-ylphenyl)-1,3-oxathiolane; 4-(5-Methyl-2-octyl-1,3-oxathiolan-2-yl)phenol; 2-Fluoro-5-(5-methyl-1,3-oxathiolan-2-yl)benzenecarbonitrile; 4-Methoxy-4'-(trifluoromethoxy)-1,1'-biphenyl; 2,6-Dimethoxy-3-[4-(trifluoromethyl)phenyl]pyridine; 2-(4-bromophenyl)-2-butyl-4-propyl-1,3-oxathiane; 4-(1,3-Dioxolan-2-yl)benzenecarbonitrile; 2-(3,5-Dimethoxyphenyl)-2-hexyl-1,3-dioxolane; 2-(4-Chlorophenyl)-2-ethyl-4-methyl-1,3-dioxolane; 5-(5,5-Diethyl-1,3-dioxan-2-yl-2-fluorobenzenecarbonitrile; 2-(4-Chlorophenyl)-4,5-dihydro-1,3-oxazole; 2-(4-Methylphenyl)-4,5-dihydro-1,3-oxazole.

More preferably the compounds are selected from the group consisting of: 2-(2-hydroxyethoxy)-2-(4-hydroxy-3-methylphenyl)-1,3-dioxolane; 2-(2-hydroxyethoxy)-2-(4-hydroxyphenyl)-1,3-dioxolane; 2-(2-hydroxyethoxy)-2-(3-bromo-4-hydroxy-5-methylphenyl)-1,3-dioxolane; Methyl 4-[2-(4-fluorophenyl)-1,3-dioxolan-2-yl]butanoate; 4-[2-(4-Fluorophenyl)-1,3-dioxolan-2-yl]butan-1-ol; 2-(4'-Bromophenyl)-2-butyl-1,3-dioxolane; 4-(4-Methoxyphenyl)-1-(3-methylbutyl)-1H-pyrazole; 1-(3-Methylbutyl)-4-(4-methylphenyl)-1H-pyrazole; 2,6-Dimethoxy-3-[4-(trifluoromethoxy)phenyl]pyridine); 2-[4-(2-Thienyl)phenyl]-1,3-thiazolane; 2-Ethyl-2-(4-methoxyphenyl)-1,3-dioxolane; 2-Hexyl-2-(4-methylphenyl)-1,3-dithiolane; 2-Hexyl-2-(4-methylphenyl)-1,3-dioxolane; 2-(4-Bromophenyl)-2-ethyl-1,3-oxathiolane; 4-(5-Methyl-1,3-oxathiolan-2-yl)benzonitrile; 2-(4-Thien-2-ylphenyl)-1,3-oxathiolane; 4-(5-Methyl-2-octyl-1,3-oxathiolan-2-yl)phenol; 2-Fluoro-5-(5-methyl-1,3-oxathiolan-2-yl)benzenecarbonitrile; 4-Methoxy-4'-(trifluoromethoxy)-1,1'-biphenyl; 2,6-Dimethoxy-3-[4-(trifluoromethyl)phenyl]pyridine; 2-(4-bromophenyl)-2-butyl-4-propyl-1,3-oxathiane; 4-(1,3-Dioxolan-2-yl)benzenecarbonitrile; 2-(4-Chorophenyl)-2-ethyl-4-methyl-1,3-dioxolane; 5-(5,5-Diethyl-1,3-dioxan-2-yl)-2-fluorobenzenecarbonitrile.

In a yet further preferred embodiment, the compound of formula (I) is selected from the group consisting of: 2-(2-hydroxyethoxy)-2-(4-hydroxy-3-methylphenyl)-1,3-dioxolane; 4-(4-Methoxyphenyl)-1-(3-methylbutyl)-1H-pyrazole; 1-(3-Methylbutyl)-4-(4-methylphenyl)-1H-pyrazole; 2-Hexyl-2-(4-methylphenyl)-1,3-dithiolane; 2-Hexyl-2-(4-methylphenyl)-1,3-dithiolane; 2-(4-Thien-2-ylphenyl)-1,3-oxathiolane; 4-Methoxy-4'-(trifluoromethoxy)-1,1'-biphenyl; 2,6-Dimethoxy-3-[4-(trifluoromethyl)phenyl]pyridine.

Examples of suitable compounds may include:

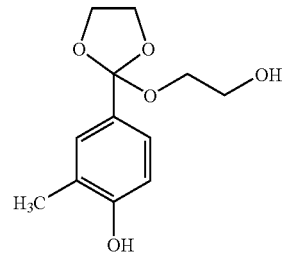

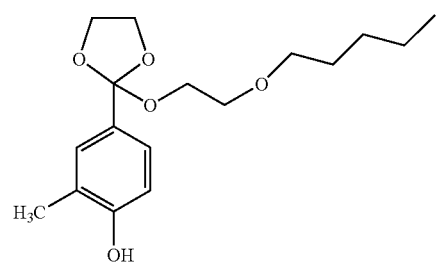

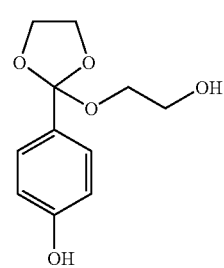

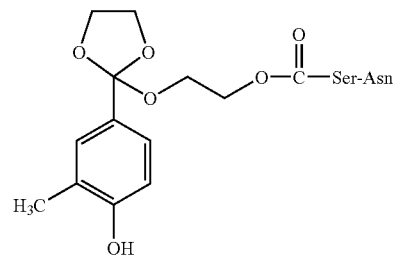

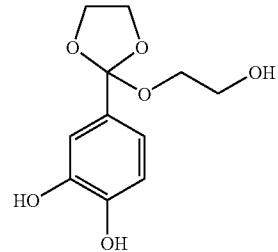

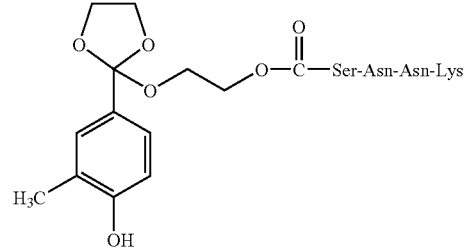

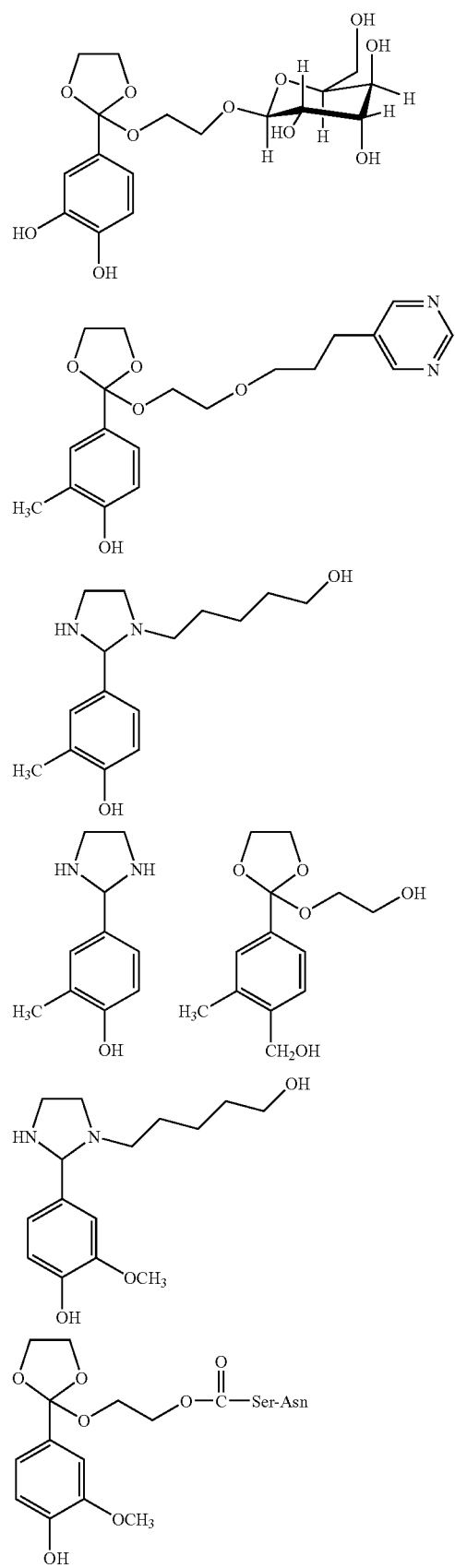
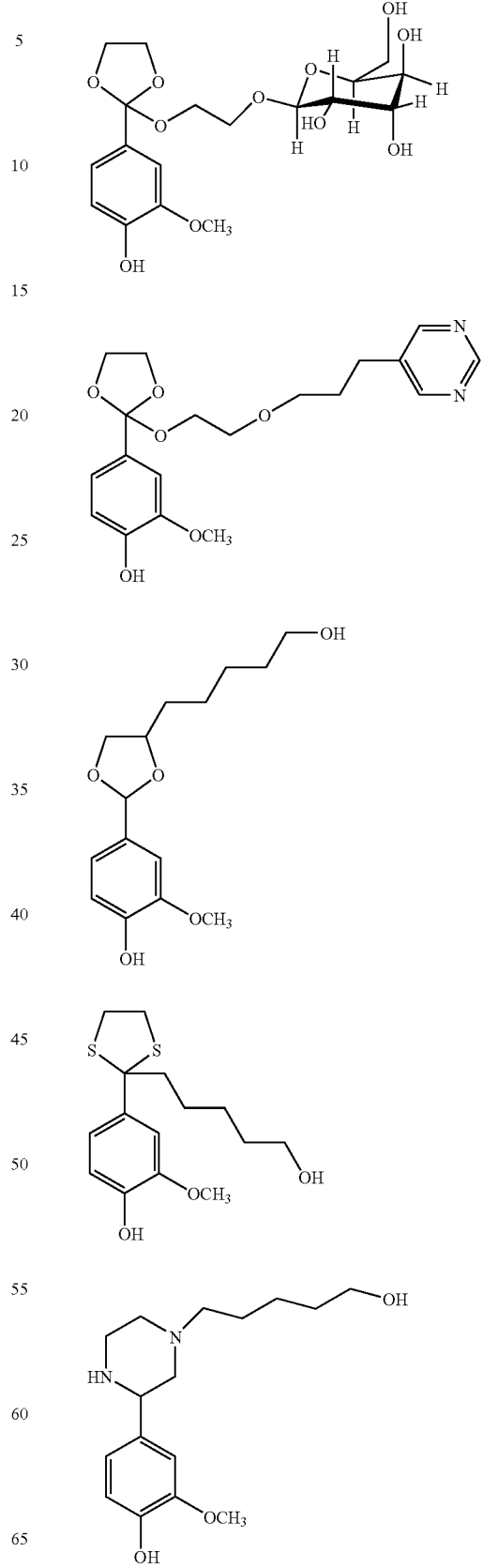

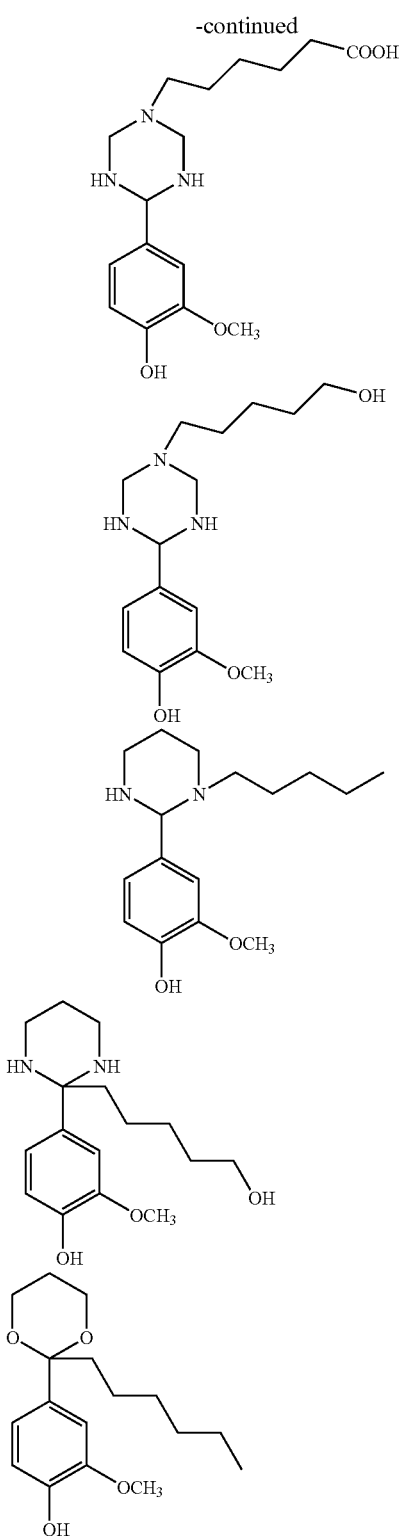

Compounds of Formula (I) may be prepared using the methods depicted or described herein or known in the art. It will be understood that minor modifications to methods described herein or known in the art may be required to synthesize particular compounds of Formula (I). General synthetic procedures applicable to the synthesis of compounds may be found in standard references such as Comprehensive Organic Transformations, R. C. Larock, 1989, VCH Publishers and Advanced Organic Chemistry, J. March, 4th Edition (1992), Wiley InterScience, and references therein. It will also be recognised that certain reactive groups may require protection and deprotection during the synthetic process. Suitable protecting and deprotecting methods for reactive functional groups are known in the art for example in Protective Groups in Organic Synthesis, T. W. Green & P. Wutz, John Wiley & Son, 3rd Edition, 1999.

Thus for certain embodiments of the invention, compounds of formula (I), where X and Y are —O—, X' and Y' are —CH$_2$—, Z is —CH$_2$— or forms a bond between X' and Y' and R$_1$ is alkyl, alkenyl, alkynyl or an optionally substituted alkylene with terminal functionality, eg (A)$_n$OMe where n is between 1 and 20, may be prepared by the general method shown in Scheme 1.

Scheme 1

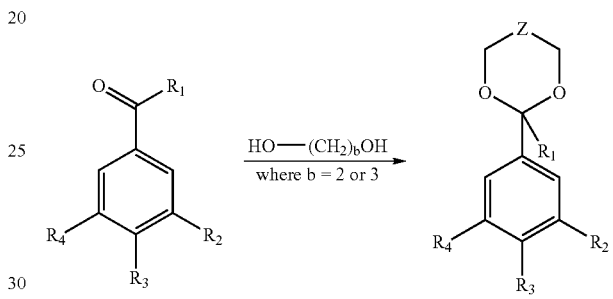

Suitable starting materials may be commercially available or made by methods known in the art. Suitable conditions for this reaction include refluxing the starting material and the dihydroxy compound in benzene in the presence of add, eg. tosylate. Other conditions for performing this reaction to provide selectivity in the presence of other carbonyl groups or to provide conditions suitable for use in the presence of other functional groups are provided in Protective Groups in Organic Synthesis, T. W. Green & P. Wutz, John Wiley & Son; 3rd Edition, 1999, pages 312-329. Functionality may be introduced into the dioxolane group by using a substituted dihydroxy compound.

1,3-dithiane or 1,3-dithiolane derivatives, where X and Y are —S—, X' and Y' are —CH$_2$—, Z is —CH$_2$— or forms a covalent bond between X' and Y' and R$_1$ is alkyl, alkenyl, alkynyl or an optionally substituted alkylene with terminal functionality, eg.: (A)$_n$OMe where n is 1 to 20, may be prepared in a similar manner as the 1,3-dioxolane derivatives in Scheme 1. Suitable conditions for this reaction include mixing the starting material and HS—(CH$_2$)$_b$—SH, where b is 2 or 3, in the presence of BF$_3$-Et$_2$O in dichloromethane at room temperature. Other conditions for performing this reaction are provided in Protective Groups in Organic Synthesis, T. W. Green & P. Wutz, John Wiley & Son; 3rd Edition, 1999, pages 333-336.

1,3-oxathiolanes, where one of X and Y is —O— and the other is —S—, X' and Y' are —CH$_2$—, Z is —CH$_2$— or forms a covalent bond between X' and Y' and R$_1$ is alkyl, alkenyl, alkynyl or an optionally substituted alkylene with terminal functionality, eg.: (A)$_n$OMe where n is 1 to 20, may be prepared in a similar manner as the 1,3-dioxolane derivatives in Scheme 1. Suitable conditions include mixing the starting material with HS—(CH$_2$)$_b$—OH where b is 2 or 3, in dioxane, in the presence of ZnCl$_2$ and AcONa at room temperature. Conditions for performing this reaction are given in Protective Groups in Organic Synthesis, T. W. Green & P. Wutz, John Wiley & Son; 3rd Edition, 1999, at page 346.

Compounds where X and Y are —N(R$_5$)—, X' and Y' are —CH$_2$—, Z is —CH$_2$— or forms a covalent bond between X' and Y' and R$_1$ is alkyl, alkenyl, alkynyl or an optionally substituted alkylene with terminal functionality, eg.: (A)$_n$OMe where n is 1 to 20, may be prepared as shown in Scheme 2 (12):

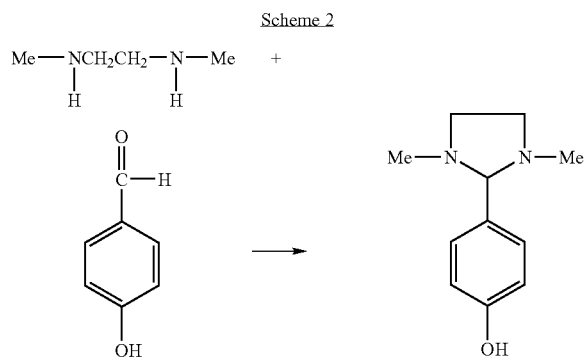

Compounds where X is —N(R$_5$)—, X' and Y' are —CH$_2$—, Z is —CH$_2$— or forms a covalent bond between X' and Y', Y together with the carbon atom to which the phenyl group is attached is a double bond and R$_1$ is absent may be prepared as shown in Scheme 3 (13).

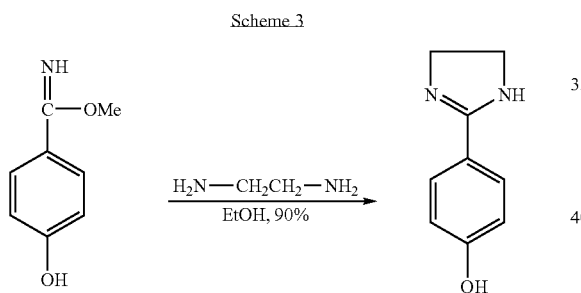

When R$_1$ includes a —CO$_2$H or —C(S)OH group, the compounds may be further derivatised to provide ketones, thioketones, esters, thioesters, amides and thioamides by standard alkylating, esterifying or amide forming methodology. When R$_1$ includes a hydroxy, thiol or amino group, these groups may be further derivatised to provide esters, thioesters, amides, ethers, thioethers and N-alkyl groups using standard acylating or alkylating methodology. Conversion of an amide to C=NH(NH$_2$) can be achieved by aminolysis eg NH$_3$/dry methanol.

In other embodiments, compounds of Formula (I), where R$_1$, R$_2$, R$_3$ or R$_4$ is a substituted methyl group, can be prepared by conversion of the methyl substituent into a halomethyl substituent (eg by treatment with a N-halosuccinimide such as NBS) followed by nucleophilic substitution by an appropriate nucleophile and/or insertion of additional methylene groups by, for example, Wittig reaction (see Scheme 4 where R* can be, for example, (CH$_2$)$_x$OH, (CH$_2$)$_x$SH, (CH$_2$)$_x$NH$_2$, (CH$_2$)$_x$heterocyclyl, (CH$_2$)$_x$aryl, (CH$_2$)$_x$NO$_2$ where x is 0, 1 or 2. Similar reactions could be performed if R$_1$ is CH$_2$Br to provide substituents such as (CH$_2$)$_n$C(O)C$_{1-20}$alkyl, (CH$_2$)$_n$OC(O)C$_{1-10}$alkyl, (CH$_2$)$_n$OC$_{1-20}$alkyl, (CH$_2$)$_n$Ophenyl, (CH$_2$)$_n$Obenzyl, (CH$_2$)$_n$NHC$_{1-20}$alkyl, (CH$_2$)$_n$N(C$_{1-20}$alkyl)$_2$, (CH$_2$)$_n$NHphenyl, (CH$_2$)$_n$NHbenzyl, (CH$_2$)$_n$SC$_{1-20}$alkyl, (CH$_2$)$_n$SC(O)C$_{1-10}$alkyl, (CH$_2$)$_n$Sphenyl, (CH$_2$)$_n$Sbenzyl, (CH$_2$)$_n$NHsugar, (CH$_2$)$_n$Ssugar, (CH$_2$)$_n$Osugar, (CH$_2$)$_n$NHC(O)C$_{1-10}$alkyl, (CH$_2$)$_n$NHC(O)phenyl, (CH$_2$)$_n$NHC(O)benzyl, (CH$_2$)$_n$NHCO$_2$C$_{1-6}$alkyl, (CH$_2$)$_n$NHCO$_2$phenyl, or (CH$_2$)$_n$NHCO$_2$benzyl, where n is 0 or 1 to 20).

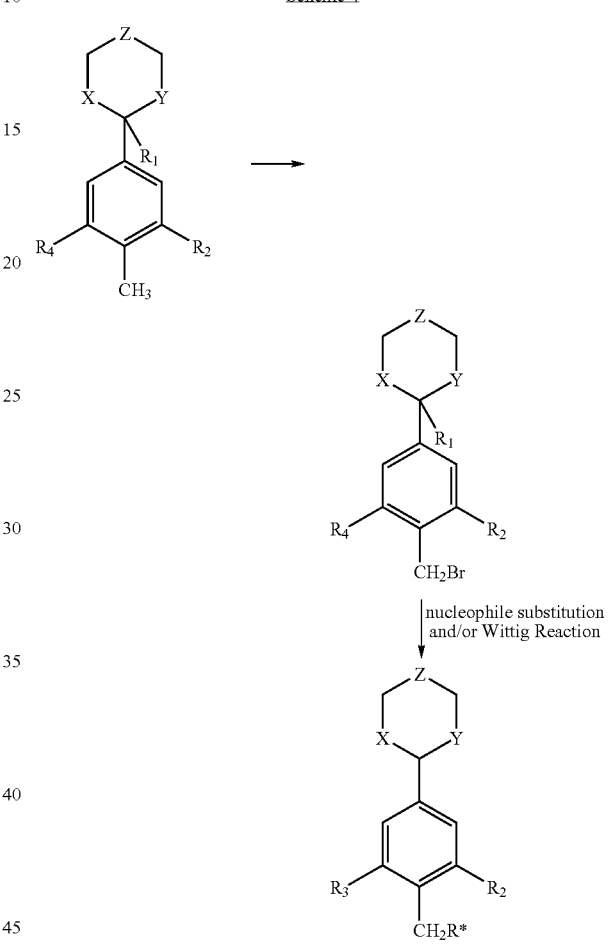

In other embodiments, compounds where R$_1$, R$_2$, R$_3$ or R$_4$ are CH$_2$halo can be prepared by reaction of a suitable carboxylic acid derivative with a reducing agent such as LiAlH$_4$, followed by halogenation, eg treatment with thionyl chloride (Scheme 5).

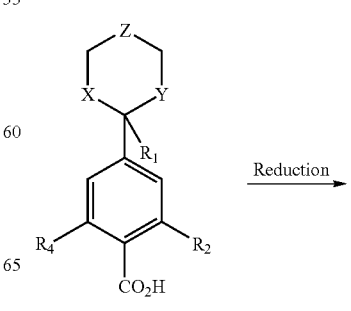

Compounds where $R_3$ is —OH, —NR or —$CH_2CN$ can be prepared from the compound where $R_3$ is $C_1$ as shown in Scheme 6

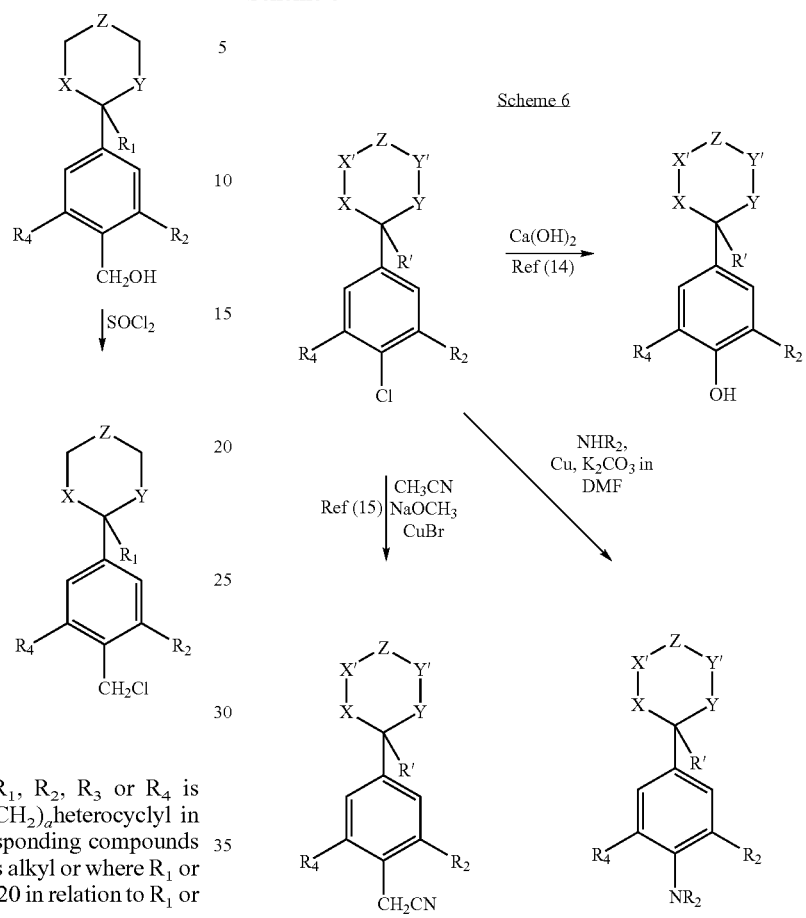

Coupling of compounds wherein $R_1$, $R_2$, $R_3$ or $R_4$ is $CH_2$halo with an alkylhalide or halo$(CH_2)_a$heterocyclyl in the presence of CuLi affords the corresponding compounds where the $R_1$, $R_2$, $R_3$ or $R_4$ substituent is alkyl or where $R_1$ or $R_3$ are $(CH_2)_a$heterocyclyl where a is 1-20 in relation to $R_1$ or 1 to 3 in relation to $R_3$.

Reaction of $CH_2$halo with $NH_2$—NH—C(=NH)—$NH_2$ in the presence of base affords access to compounds wherein $R_1$ is $CH_2$—NH—NH—C(=NH)—$NH_2$. Alternatively, reaction of the $CH_2$halo group with halo$(CH_2)_p$NH—NH—C(=NH)—$NH_2$ (where p is 1 or 2), affords the group $(CH_2)_p$NH—NH—C(=NH)—$NH_2$ where p is 2 or 3.

Compounds according to formula (I) in which X' and Y' are each —N($R_5$)— and Z is —$CH_2$— can be prepared as is shown in Scheme 7. (Reference: Journal of American Chemical Society, 123(19), 4451-4458, 2001

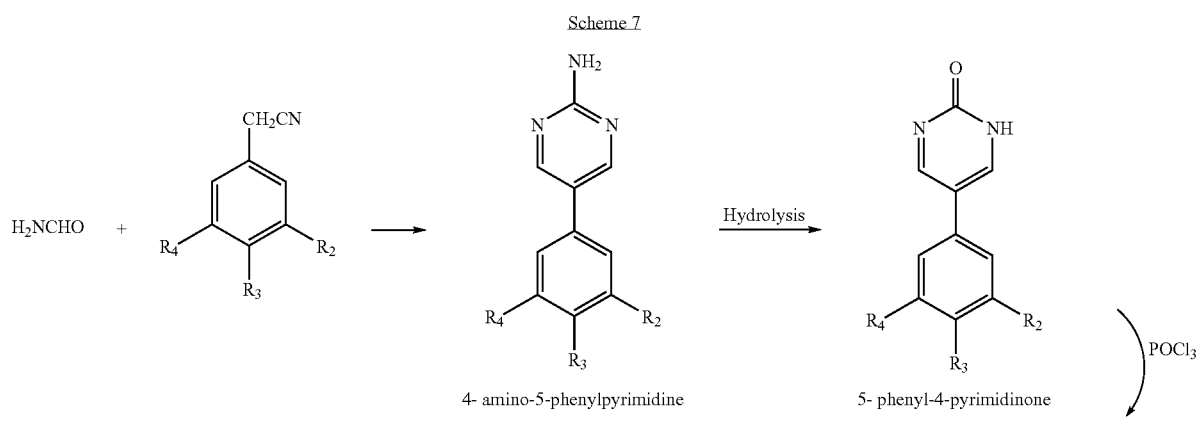

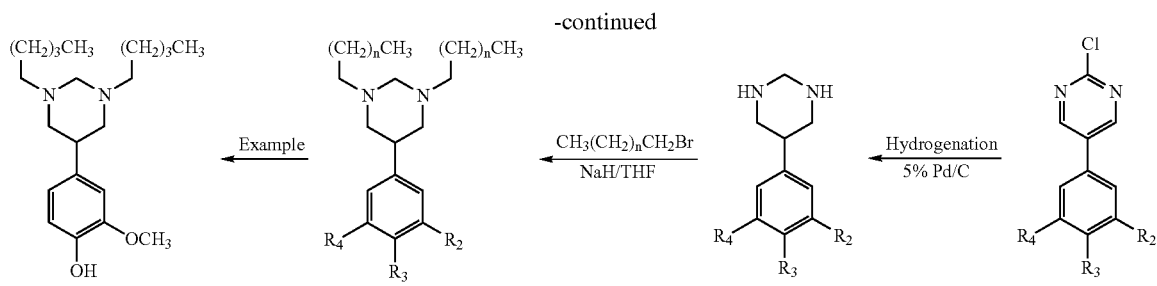
Several compounds can be made by varing $R_2$, $R_3$, $R_4$, and n
$R_2 = OCH_3$
$R_3 = OH$
$R_4 = H$
n = 3
Compounds in which X is O, Y' is —N($R_5$)— and Z is —$CH_2$— can be prepared as is shown in Scheme 8.
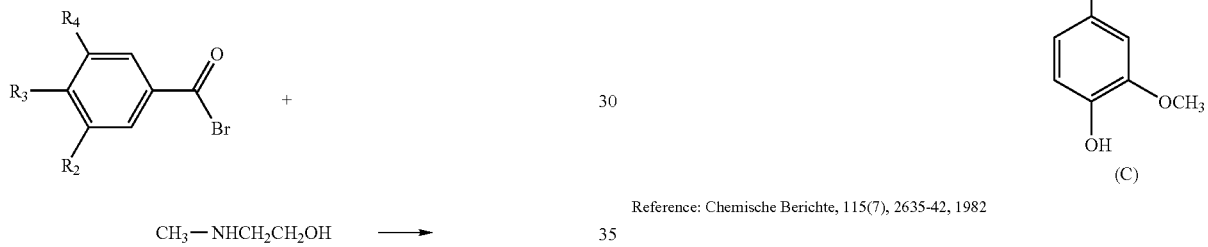
Reference: Chemische Berichte, 115(7), 2635-42, 1982
Compounds in which X and X' are each —C($R_5$)$_2$—, Z is a bond and Y is —N($R_5$)— can be prepared according to scheme 9.
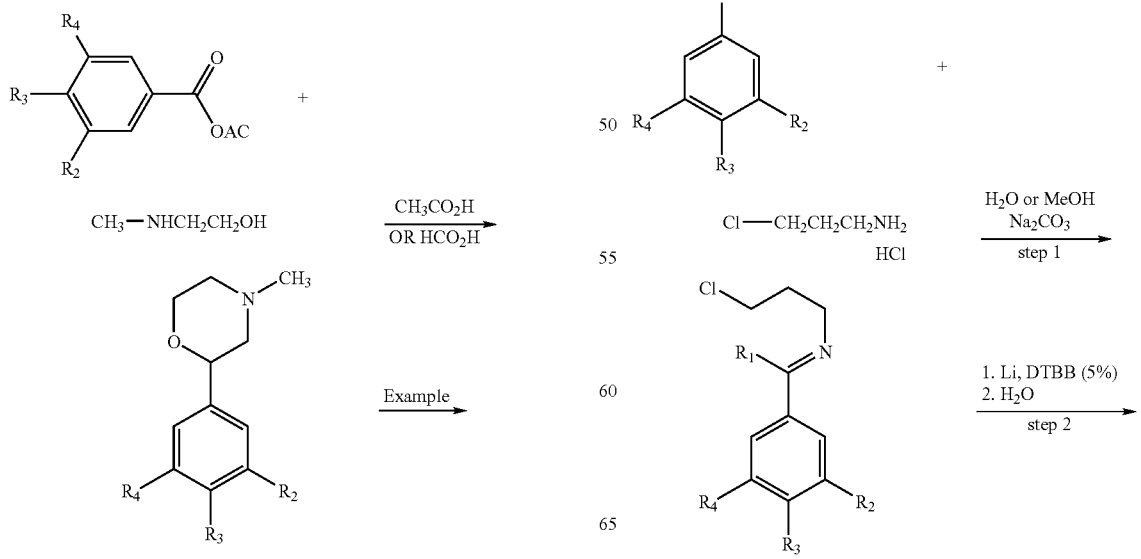

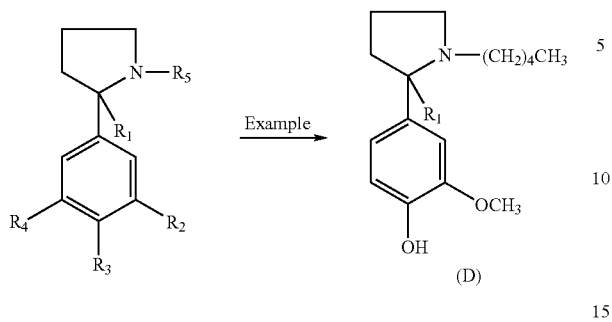
(D)
Reference: *J. Org. Chem.* 66, 6207-6208, 2001
Compounds in which X is —N(R5)-, Y is —N(R5)- and Z is a bond can be prepared according to scheme 10.
Scheme 10
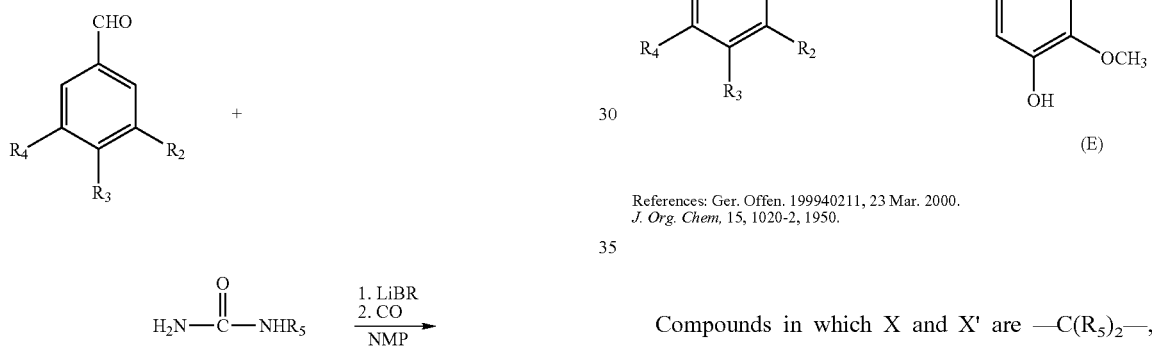
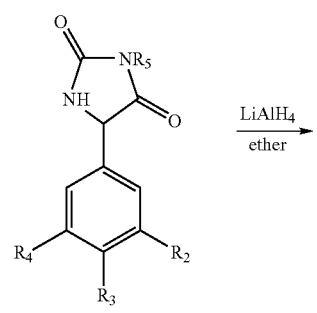
(E)
References: Ger. Offen. 199940211, 23 Mar. 2000.
*J. Org. Chem*, 15, 1020-2, 1950.
Compounds in which X and X' are —C(R$_5$)$_2$—, Z is —CH$_2$— and Y' is —N(R$_5$)— can be prepared according to Scheme 11.
Scheme 11
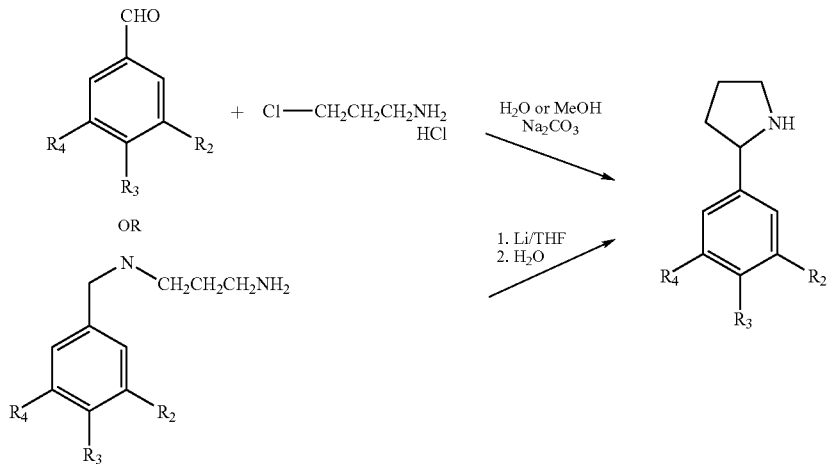
Reference: *J. Org. Chem.* 66, 6207-6208, 2001

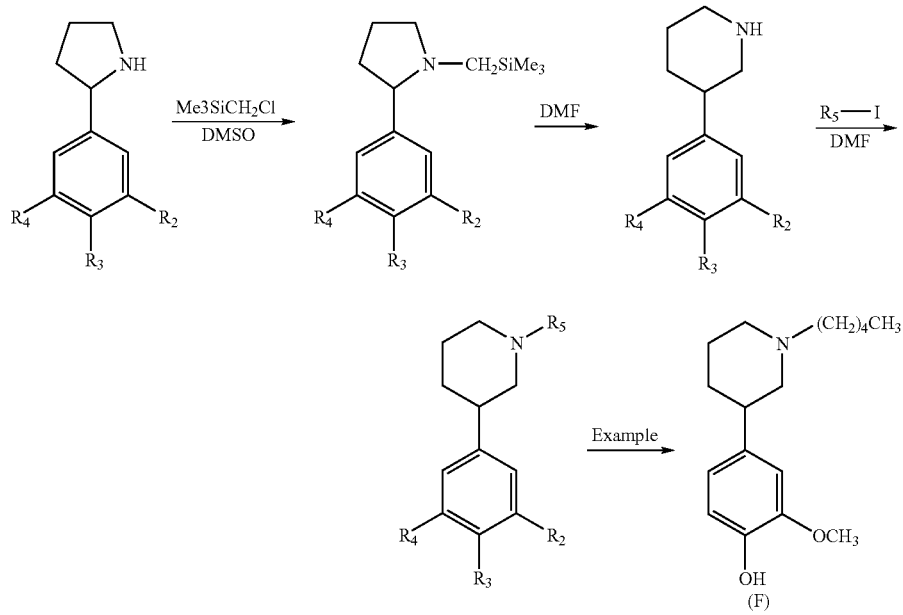

Reference: *Chemical & Pharmaceutical Bulletin*, 39(1), 36-40, 1991

2-Ethyl-2-(4-methoxyphenyl)-1,3-dioxolane, Compound 16, the synthesis of which is reported below, is prepared by the following the reaction scheme 12 and it would be understood by a person skilled in the art that a similar methodology can be used to prepare other appropriately substituted 1,3-dioxolanes.

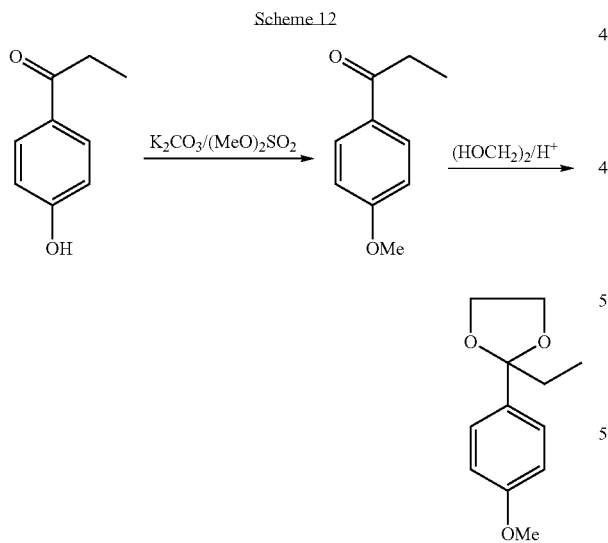

2-Hexyl-2-(4-methylphenyl)-1,3-dithiolane, Compound 17, the synthesis of which is reported below, is prepared by following the reaction scheme 13 and it would be understood by a person skilled in the art that a similar methodology can be used to prepare other appropriately substituted 1,3-dithiolanes.

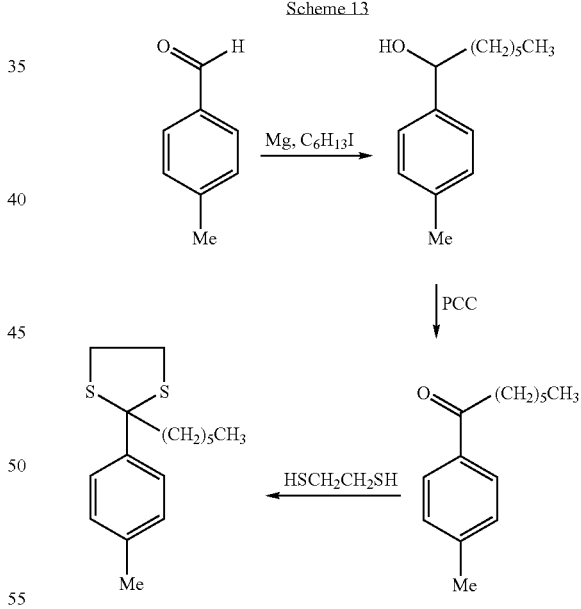

The term "salt, or prodrug" includes any pharmaceutically acceptable salt, ester, solvate, hydrate or any other compound which, upon administration to the recipient is capable of providing (directly or indirectly) a compound of Formula (I) as described herein. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate, or where a free amino group is converted into an amide. Procedures for acylating hydroxy or amino groups of the compounds of the invention are well known in the art and may include treatment of the compound with an appropriate carboxylic acid, anhydride or acylchloride in the presence of a suitable catalyst or base.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will also be recognised that some compounds of formula (I) may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In a further aspect, the present invention provides a method of inhibiting cytokine or biological activity of MIF comprising contacting MIF with a cytokine or biological activity inhibiting effective amount of a compound of formula (I), or a pharmaceutically acceptable salt or prodrug thereof.

In another aspect, the invention provides a method of treating, preventing or diagnosing a disease or condition wherein MIF cytokine or biological activity is implicated comprising the administration of a treatment, prevention or diagnostic effective amount of a compound of formula (I) or a pharmaceutically acceptable salt or prodrug thereof to a subject in need thereof.

In a further aspect, there is provided the use of a compound of formula (I) or a pharmaceutically acceptable salt or prodrug thereof in the manufacture of a medicament for the treatment, prevention or diagnosis of a disease or condition wherein MIF cytokine or biological activity is implicated.

As used herein, MIF includes human or other animal MIF and derivatives and naturally occurring variants thereof which at least partially retain MIF cytokine or biological activity. Thus, the subject to be treated may be human or other animal such as a mammal. Non-human subjects include, but are not limited to primates, livestock animals (eg sheep, cows, horses, pigs, goats), domestic animals (eg dogs, cats), birds and laboratory test animals (eg mice rats, guinea pigs, rabbits). MIF is also expressed in plants (thus "MIF" may also refer to plant MIF) and where appropriate, compounds of Formula (I) may be used in botanical/agricultural applications such as crop control.

Reference herein to "cytokine or biological activity" of MIF includes the cytokine or biological effect on cellular function via autocrine, endocrine, paracrine, cytokine, hormone or growth factor activity or via intracellular effects.

In a further aspect of the invention there is provided a method of treating, diagnosing, or preventing autoimmune diseases, tumours or chronic or acute inflammatory diseases comprising administration of a treatment, diagnosis or prevention effective amount of a compound of formula (I), or a pharmaceutically acceptable salt or prodrug thereof. Such diseases include:

rheumatic diseases (including but not limited to rheumatoid arthritis, osteoarthritis, psoriatic arthritis) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, polymyalgia rheumatica;

connective tissue diseases (including but not limited to systemic lupus erythematosus, systemic sclerosis, polymyositis, dermatomyositis, Sjögren's syndrome);

vasculitides (including but not limited to polyarteritis nodosa, Wegener's granulomatosis, Churg-Strauss syndrome);

inflammatory conditions including consequences of trauma or ischaemia, sarcoidosis;

vascular diseases including atherosclerotic vascular disease, atherosclerosis, and vascular occlusive disease (including but not limited to atherosclerosis, ischaemic heart disease, myocardial infarction, stroke, peripheral vascular disease), and vascular stent restenosis;

ocular diseases including uveitis, corneal disease, iritis, iridocyclitis, cataracts; autoimmune diseases (including but not limited to diabetes mellitus, thyroiditis, myasthenia gravis, sclerosing cholangitis, primary biliary cirrhosis);

pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome);

cancers whether primary or metastatic (including but not limited to prostate cancer, colon cancer, lymphoma, lung cancer, melanoma, multiple myeloma, breast cancer, stomach cancer, leukaemia, cervical cancer and metastatic cancer);

renal diseases including glomerulonephritis, interstitial nephritis;

disorders of the hypothalamic-pituitary-adrenal axis;

nervous system disorders including multiple sclerosis, Alzheimer's disease;

diseases characterised by modified angiogenesis (eg diabetic retinopathy, rheumatoid arthritis, cancer), endometrial function (menstruation, implantation, endometriosis);

complications of infective disorders including endotoxic (septic) shock, exotoxic (septic) shock, infective (true septic) shock, malarial complications, other complications of infection, pelvic inflammatory disease;

transplant rejection, graft-versus-host disease;

allergic diseases including allergies, atopic diseases, allergic rhinitis;

bone diseases (eg osteoporosis, Paget's disease);

skin diseases including psoriasis, atopic dermatitis, UV(B)-induced dermal cell activation (eg sunburn, skin cancer);

complications of diabetes mellitus, pain, testicular dysfunctions and wound healing, gastrointestinal diseases including inflammatory bowel disease (including but not limited to ulcerative colitis, Crohn's disease), peptic ulceration, gastritis, oesophagitis, liver disease (including but not limited to cirrhosis, hepatitis).

Particularly preferred diseases or conditions include: rheumatoid arthritis, systemic lupus erythematosus, ulcerative colitis, Crohn's disease, multiple sclerosis, psoriasis, uveitis, atherosclerotic vascular disease, asthma and chronic obstructive pulmonary disease.

A further aspect of the invention provides for the use of a compound of Formula (I) or a pharmaceutically acceptable salt or prodrug thereof in the manufacture of a medicament for the treatment of a disease or condition as above.

As used herein, the term "effective amount" relates to an amount of compound which, when administered according to a desired dosing regimen, provides the desired MIF cytokine inhibiting or treatment or therapeutic activity, or disease/condition prevention. Dosing may occur at intervals of minutes, hours, days, weeks, months or years or continuously over any one of these periods. A cytokine or biological activity inhibiting amount is an amount which will at least partially inhibit the cytokine or biological activity of MIF. A therapeutic, or treatment, effective amount is an amount of the compound which, when administered according to a desired dosing regimen, is sufficient to at least partially attain the desired therapeutic effect, or delay the onset of, or inhibit the progression of or halt or partially or fully reverse the onset or progression of a particular disease condition being treated. A prevention effective amount is an amount of compound which when administered according to the desired dosing regimen is sufficient to at least partially prevent or delay the onset of a particular disease or condition. A diagnostic effective amount of compound is an amount sufficient to bind to MIF to enable detection of the MIF-compound complex such that diagnosis of a disease or condition is possible.

Suitable dosages may lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

Suitable dosage amounts and dosing regimens can be determined by the attending physician or veterinarian and may depend on the desired level of inhibiting activity, the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition.

In a further aspect of the invention, there is provided a pharmaceutical composition comprising a compound of formula (I) together with a pharmaceutically acceptable carrier, diluent or excipient.

The formulation of such compositions is well known to those skilled in the art. The composition may contain pharmaceutically acceptable additives such as carriers, diluents or excipients. These include, where appropriate, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, inhalational, nasal, transdermal, topical (including buccal and sublingual), vaginal or parenteral (including subcutaneous, intramuscular, intraspinal, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Depending on the disease or condition to be treated, it may or may not be desirable for a compound of Formula (I) to cross the blood/brain barrier. Thus the compositions for use in the present invention may be formulated to be water or lipid soluble.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg inert diluent, preservative, disintegrant (eg. sodium starch glycolate, cross-linked polyvinyl pyrrolidone, cross-linked sodium carboxymethyl cellulose)) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

The compounds of Formula (I) may also be administered intranasally or via inhalation, for example by atomiser, aerosol or nebulizer means.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal devices, such as patches, may also be used to administer the compounds of the invention.

Compositions for rectal administration may be presented as a suppository with a suitable carrier base comprising, for example, cocoa butter, gelatin, glycerin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

It will be recognised that other therapeutically active agents such as anti-inflammatory (eg steroids such as glucocorticoids) or anti-cancer agents may be used in conjunction with a compound of Formula (I). Compounds of Formula (I) when administered in conjunction with other therapeutically active agents may exhibit an additive or synergistic effect. These may be administered simultaneously, either as a combined form (ie as a single composition containing the active agents) or as discrete dosages. Alternatively, the other therapeutically active agents may be administered sequentially or separately with the compounds of the invention. Thus, the invention also relates to kits and combinations, comprising a compound of Formula (I) and one or more other therapeutically active ingredients for use in the treatment of diseases or conditions described herein. Without being limiting, examples of agents which could be used in combination with a compound of Formula (I) include: antirheumatic drugs (including but not limited to methotrexate, leflunomide, sulphasalazine, hydroxycholorquine, gold salts); immunosuppressive drugs (including but not limited to cyclosporin, mycophenyllate mofetil, azathioprine, cyclophosphamide); anti-cytokine therapies (including but not limited to antagonists of, antibodies to, binding proteins for, or soluble receptors for tumor necrosis factor, interleukin 1, interleukin 3, interleukin 5, interleukin 6, interleukin 8, interleukin 12, interleukin 18, interleukin 17, and other pro-inflammatory cytokines as may be found relevant to pathological states); antagonists or inhibitors of mitogen-activated protein (MAP) kinases (including but not limited to antagonists or inhibitors of extracellular signal-regulated kinases (ERK), the c-Jun N-terminal kinases/stress-activated protein kinases (JNK/SAPK), and the p38 MAP kinases, and other kinases or enzymes or proteins involved in MAP kinase-dependent cell activation); antagonists or inhibitors of the nuclear factor kappa-B (NF-B) signal transduction pathway (including but not limited to antagonists or inhibitors of I-B-kinase, interleukin receptor activated kinase, and other kinases or enzymes or proteins involved in NF-B-dependent cell activation); antibodies, protein therapeutics, or small molecule therapeutics interacting with adhesion molecules and co-stimulatory molecules (including but not limited to therapeutic agents directed against intercellular adhesion molecule-1, CD40, CD40-ligand, CD28, CD4, CD-3, selectins such as P-selectin or E-selectin); bronchodilators such as ε-adrenoceptor agonists or anti-cholinergics; antagonists of eicosanoid synthesis pathways such as non-steroidal anti-inflammatory drugs, cyclooxygenase-2 inhibitors, thromboxane inhibitors, or lipoxygenase inhibitors; antibodies or other agents directed against leukocyte surface antigens (including but not limited to antibodies or other agents directed against CD3, CD4, CD5, CD19, CD20, HLA molecules); agents used for the treatment of inflammatory bowel disease (including but not limited to sulphasalazine, mesalazine, salicylic acid derivatives); anti-cancer drugs (including but not limited to cytotoxic drugs, cytolytic drugs, monoclonal antibodies).

In another aspect, the invention provides a method of treating or preventing a disease or condition wherein MIF cytokine or biological activity is implicated comprising:
   administering to a mammal a compound of formula (I) and a second therapeutic agent.

In a preferred embodiment of this aspect of the invention, the second therapeutic agent is a glucocorticoid compound.

In another aspect, the present invention provides a method of prophylaxis or treatment of a disease or condition for which treatment with a glucocorticoid is indicated, said method comprising: administering to a mammal a glucocorticoid and a compound of formula (I).

In yet another aspect, the present invention provides a method of treating steroid-resistant diseases comprising administering to a mammal a glucocorticoid and a compound of formula (I).

In a further aspect, the present invention provides a method of enhancing the effect of a glucocorticoid in mammals comprising administering a compound of formula (I) simultaneously, separately or sequentially with said glucocorticoid.

In yet a further aspect, the present invention provides a composition comprising a glucocorticoid and a compound of formula (I).

In a further aspect of the invention there is provided a use of a glucocorticoid in the manufacture of a medicament for administration with a compound of formula (I) for the treatment or prophylaxis of a disease or condition for which treatment with a glucocorticoid is indicated.

In yet a further aspect of the invention there is provided a use of a compound of formula (I) in the manufacture of a medicament for administration with a glucocorticoid for the treatment or prophylaxis of a disease or condition for which treatment of a glucocorticoid is indicated.

In yet a further aspect of the invention there is provided a use of a glucocorticoid and a compound of formula (I) in the manufacture of a medicament for the treatment or prophylaxis of a disease or condition for which treatment with a glucocorticoid is indicated.

Preferably the amount of glucocorticoid used in the methods, uses and compositions of the invention is less than the amount which would be effective in the absence of the compound of formula (I). In the treatment of steroid-resistant diseases or conditions which are not responsive to glucocorticoids, any amount of glucocorticoid which is effective in combination with a compound of formula (I) is considered less than the amount which would be effective in the absence of a compound formula (I). Accordingly, the invention provides a steroid-sparing therapy.

In preferred embodiments of the invention, the glucocorticoid and the compound of formula (I) are used to treat or prevent a disease or condition in a mammal, preferably in a human subject.

The term "disease or condition for which treatment with a glucocorticoid is indicated" refers to diseases or conditions which are capable of being treated by administration of a glucocorticoid including but not limited to autoimmune diseases, tumours, or chronic or acute inflammatory diseases. Examples of such diseases or conditions include:
- rheumatic diseases (including but not limited to rheumatoid arthritis, osteoarthritis, psoriatic arthritis) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, polymyalgia rheumatica;
- connective tissue diseases (including but not limited to systemic lupus erythematosus, systemic sclerosis, polymyositis, dermatomyositis, Sjögren's syndrome);
- vasculitides (including but not limited to polyarteritis nodosa, Wegener's granulomatosis, Churg-Strauss syndrome);
- inflammatory conditions including consequences of trauma or ischaemia, sarcoidosis;
- vascular diseases including atherosclerotic vascular disease, atherosclerosis, and vascular occlusive disease (including but not limited to atherosclerosis, ischaemic heart disease, myocardial infarction, stroke, peripheral vascular disease), and vascular stent restenosis;
- ocular diseases including uveitis, corneal disease, iritis, iridocyclitis, cataracts;
- autoimmune diseases (including but not limited to diabetes mellitus, thyroiditis, myasthenia gravis, sclerosing cholangitis, primary biliary cirrhosis);
- pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome);
- cancers whether primary or metastatic (including but not limited to prostate cancer, colon cancer, lymphoma, lung cancer, melanoma, multiple myeloma, breast cancer, stomach cancer, leukaemia, cervical cancer and metastatic cancer);
- renal diseases including glomerulonephritis, interstitial nephritis;
- disorders of the hypothalamic-pituitary-adrenal axis;
- nervous system disorders including multiple sclerosis, Alzheimer's disease;
- diseases characterised by modified angiogenesis (eg diabetic retinopathy, rheumatoid arthritis, cancer), endometrial function (menstruation, implantation, endometriosis);
- complications of infective disorders including endotoxic (septic) shock, exotoxic (septic) shock, infective (true septic) shock, malarial complications, other complications of infection, pelvic inflammatory disease;
- transplant rejection, graft-versus-host disease;
- allergic diseases including allergies, atopic diseases, allergic rhinitis;
- bone diseases (eg osteoporosis, Paget's disease);
- skin diseases including psoriasis, atopic dermatitis, UV(B)-induced dermal cell activation (eg sunburn, skin cancer);
- complications of diabetes mellitus, pain, testicular dysfunctions and wound healing,
- gastrointestinal diseases including inflammatory bowel disease (including but not limited to ulcerative colitis, Crohn's disease), peptic ulceration, gastritis, oesophagitis, liver disease (including but not limited to cirrhosis, hepatitis).

These diseases or conditions may also include steroid-resistant diseases or conditions where treatment with a glucocorticoid is indicated, but where the glucocorticoid is ineffective or is not as effective as expected.

The methods of the invention are preferably performed in a steroid-sparing manner. The term "steroid-sparing" refers to a combination therapy method that allows a reduction in the amount of glucocorticoid administered while still providing an effective therapy for the disease or condition being treated or prevented.

Steroid-resistant diseases or conditions are diseases or conditions for which treatment with a glucocorticoid is indicated, but where the glucocorticoid is ineffective or is not as effective as expected. This term encompasses diseases or conditions for which the effective dose of glucocorticoid results in unacceptable side effects and/or toxicity. Some steroid-resistant diseases or conditions may require a dosage of glucocorticoid so large that they are considered non-responsive and therefore are not able to be successfully treated with glucocorticoids. Some steroid-resistant diseases or conditions may require a large dosage of glucocorticoid to achieve only a small effect on the symptoms of the disease or condition. Furthermore, some patients, diseases or conditions present with symptoms that do not respond to treatment with a glucocorticoid, or may become less sensitive to glucocorticoid treatment over time.

Glucocorticoids are a group of steroid hormones, which are used to treat or prevent a wide range of diseases or conditions. Suitable glucocorticoids may be synthetic or naturally occurring and include but are not limited to prednisolone, prednisone, cortisone acetate, beclamethasone, fluticasone, hydrocortisone, dexamethasone, methyl prednisolone, triamcinolone, budesonide and betamethasone.

In preferred embodiments of the invention, the glucocorticoid used is selected from prednisone, prednisolone, hydrocortisone, fluticasone, beclamethasone, betamethasone, methyl prednisolone, budesonide, triamcinolone, dexamethasone and cortisone. Most preferably, the glucocorticoid is selected from prednisone, prednisolone, methyl prednisolone, fluticasone and beclamethasone. Beclamethasone and fluticasone are particularly preferred for treating asthma.

Prednisone, prednisolone and methyl prednisolone are particularly preferred in the treatment of systemic or local inflammatory diseases.

The amounts of glucocorticoid and compound of formula (I) are selected such that in combination they provide complete or partial treatment or prophylaxis of a disease or condition for which a glucocorticoid is indicated. The amount of compound formula (I) is preferably an amount that will at least partially inhibit the cytokine or biological activity of MIF. The amount of glucocorticoid is preferably less than the amount required in the absence of the compound of formula (I). The amounts of glucocorticoid and compound of formula (I) used in a treatment or therapy are selected such that in combination they at least partially attain the desired therapeutic effect, or delay onset of, or inhibit the progression of, or halt or partially or fully reverse the onset or progression of the disease or condition being treated. The amounts of glucocorticoid and compound of formula (I) used in the prophylaxis of a disease or condition are selected such that in combination they at least partially prevent or delay the onset of the disease or condition. Dosing may occur at intervals of minutes, hours, days, weeks, months or years or continuously over any one of these periods.

Suitable doses of a compound of formula (I) may lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

Suitable dosage amounts of glucocorticoids will depend, in part, on the mode of administration and whether the dosage is being administered in a single, daily or divided dose, or as a continuous infusion. When administered orally, intravenously, intramuscularly, intralesionally or intracavity (eg. intra-articular, intrathecal, intrathoracic), dosages are typically between 1 mg to 1000 mg, preferably 1 mg to 100 mg, more preferably 1 mg to 50 mg or 1 mg to 10 mg per dose. When administered topically or by inhalation as a single, daily or divided dose, dosages are typically 1 ng to 1 µg, 1 ng to 1 mg or 1 pg to 1 µg.

Suitable dosage amounts and dosing regimens can be determined by the attending physician or veterinarian and may depend on the desired level of inhibiting activity, the particular condition being treated, the severity of the condition as well as the general age, health and weight of the subject.

The glucocorticoid and compound of formula (I) may be administered simultaneously or sequentially. The active ingredients may be administered alone but are preferably administered as a pharmaceutically acceptable composition or separate pharmaceutically acceptable compositions.

The formulation of such compositions is well known to those skilled in the art and are described above in relation to compounds of formula (I). The composition or compositions may contain pharmaceutically acceptable additives such as carriers, diluents or excipients. These include, where appropriate, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents.

Preferred unit dosage compositions are those containing a daily dose or unit, daily sub-dose, as herein above described, or an appropriate fraction thereof, of the glucocorticoids and/or compound of formula (I) which inihibit the cytokine or biological activity of MIF.

The compounds of formula (I), either as the only active agent or together with another active agent, eg: a glucocorticoid, may also be presented for use in veterinary compositions. These may be prepared by any suitable means known in the art. Examples of such compositions include those adapted for:

oral administration, external application (eg drenches including aqueous and non-aqueous solutions or suspensions), tablets, boluses, powders, granules, pellets for admixture with feedstuffs, pastes for application to the tongue;

parenteral administration, eg subcutaneous, intramuscular or intravenous injection as a sterile solution or suspension; and topical application eg creams, ointments, gels, lotions, etc.

By virtue of their ability to bind to or antagonize MNF, compounds of Formula (I) or salts or derivatives thereof may be used as laboratory or diagnostic or in vivo imaging reagents. Typically, for such use the compounds would be labelled in some way, for example, radio isotope, fluorescence or calorimetric labelling, or be chelator conjugated. In particular, compounds of Formula (I) could be used as part of an assay system for MIF or as controls in screens for identifying other inhibitors. Those skilled in the art are familiar with such screens and could readily establish such screens using compounds of Formula (I). Those skilled in the art will also be familiar with the use of chelate conjugated molecules for in vivo diagnostic imaging.

Inhibitors of MIF may also be used in implantable devices such as stents. Accordingly, in a further aspect the present invention provides an implantable device, preferably a stent, comprising:

(i) a reservoir containing at least one compound of formula (I); and (ii) means to release or elute the inhibitor from the reservoir There is further provided a method for inhibiting the cytokine or biological activity of MIF in a subject comprising the step of implanting an implantable device according to the invention in the subject.

Preferably, the method is for inhibiting the cytokine or biological activity of MIF in a local region of the subject and the device is implanted within or proximate to the local region of the subject.

In a yet further aspect, the present invention provides a method of treating, preventing or diagnosing a disease or condition wherein MIF cytokine activity is implicated comprising the step of implanting an implantable device according to the invention in a subject in need thereof.

Preferably, the disease or condition is confined to a local region of the subject and the device is implanted within or proximate to the local region.

The present invention further provides an angioplastic stent for inhibiting the onset of restenosis, which comprises an angioplastic stent operably coated with a prophylactically effective dose of a composition comprising at least one compound of formula (I).

Angioplastic stents, also known by other terms such as "intravascular stents" or simply "stents", are well known in the art. They are routinely used to prevent vascular closure due to physical anomalies such as unwanted inward growth of vascular tissue due to surgical trauma. They often have a tubular, expanding lattice-type structure appropriate for their function, and can optionally be biodegradable.

In this invention, the stent can be operably coated with at least one compound of formula (I) using any suitable means known in the art. Here, "operably coating" a stent means coating it in a way that permits the timely release of the compound(s) of formula (I) into the surrounding tissue to be treated once the coated stent is administered. Such coating methods, for example, can use the polymer polypyrrole.

The present invention further provides a method for inhibiting the onset of restenosis in a subject undergoing angioplasty, which comprises topically administering a stent according to the present invention to the subject at around the time of the angioplasty.

As used herein, administration "at around the time of angioplasty" can be performed during the procedure, or immediately before or after the procedure. The administering can be performed according to known methods such as catheter delivery.

There is further provided a method of reducing the severity of stent restenosis in the vicinity of a stent comprising the use of a stent according to the present invention.

The construction of stents that release or elute a pharmaceutical active is known to those skilled in the art. The standard approach is to use current highly refined metallic stent designs with polymer materials that release the active in a controlled manner. Several polymer materials have been used for the coating of stents to permit the elution of drugs. These include bioerodible polymers such as poly-L lactic acid, biostable polymers such as polyurethane derivatives and silicone-based polymers, as well as hydrogels. It will be recognised by those skilled in the art that the function of a drug-eluting stent requires the drug to be bound to the stent or its polymer or other coating in such a way as to allow steady release of drug over a period of time, and that the drug is able to be locally absorbed into cells in the vessel and stent lumen. The optimum stent coating material and delivery parameters vary according to the tissue retention of the drug, such that rapid release of a tissue-retained drug can have long lasting effects, whereas a drug retained in tissues for a shorter time would need to be released over a longer period. A person skilled in the art would be able to select appropriate materials and conformations of stent for a particular purpose and particular small molecule inhibitor.

Unless the context indicates otherwise, reference to any prior art in this specification is not, and should not be taken as, an acknowledgment or any form of suggestion that that prior art forms part of the common general knowledge in Australia.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are included for the purpose of illustration only and are not intended to limit the generality of the invention hereinbefore described.

EXAMPLES

Example 1

Preparation of 2-(2-hydroxyethoxy)-2-(4-hydroxy-3-methylphenyl)-1,3-dioxolane (Compound 1)

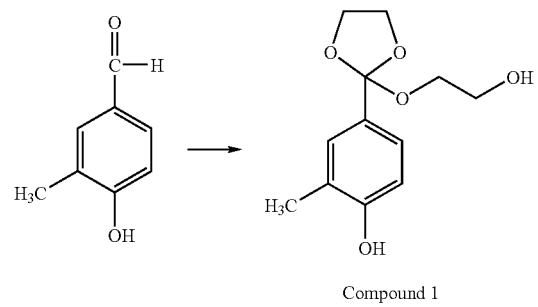

Compound 1

A mixture of 3-methyl-p-hydroxybenzaldehyde (0.5 g, 3.6 mmol), ethylene glycol (0.34 g, 5.5 mmol) and p-toluenesulfonic acid (0.07 g, 0.36 mmol) in toluene was heated under reflux. After 24 h, the reaction mixture was cooled to room temperature, TLC showed no starting material. The toluene was removed in vacuo and saturated solution of sodium hydrogen carbonate (20 ml) was added to the residue, which was then extracted with ethyl acetate (3×20 ml). The organic layer was washed with water (20 ml), dried over anhydrous sodium sulfate and the solvent was removed in vacuo. The residue was then recrystallised from an ethyl acetate and hexane mixture to give the product as a brown solid in 24% yield.

$^1$H NMR (CDCl$_3$): 2.21 (s, 3H), 3.62 (t, 2H, J=4.5 Hz), 3.70 (t, 2H, J=4.2 Hz), 3.81 (t, 2H, J=4.7 Hz), 4.42 (t, 2H, J=4.7 Hz), 6.74 (d, 1H, J=8.4 Hz), 7.21 (d, 1H, J=8.4 Hz) and 7.78 (s, 1H). MS: m/e 263 (M++Na), 179 (M+−OCH$_2$CH$_2$OH), 147, 135, 118 and 107.

$^{13}$C NMR (CDCl$_3$): 15.7, 61.1, 63.5, 69.1, 72.4, 114.0, 120.5, 124.5, 128.4, 135.6, 159.8 and 167.1.

Example 2

Preparation of 2-(2-hydroxyethoxy)-2-(4-hydroxyphenyl)-1,3-dioxolane (Compound 2)

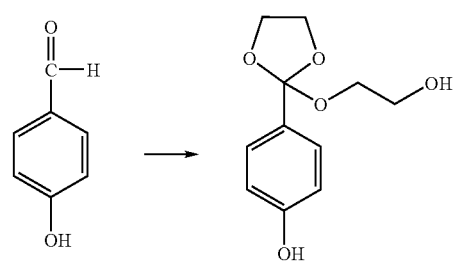

Compound 2

To a solution of p-hydroxybenzaldehyde (1 g, 8.18 mmol) in anhydrous toluene (100 mL) was added ethylene glycol (0.68 mL, 12.28 mmol), pyridinium toluene sulphonate (0.2 g, 0.88 mmol) and p-toluene sulphonic acid monohydrate (0.16 g, 0.88 mmol). The solution was refluxed overnight before concentrating the solvent to furnish an amber gum. Saturated sodium bicarbonate (50 mL) was then added to the reaction mixture, and extracted with ethyl acetate (3×50 mL). The organic extracts were dried over magnesium sulphate, filtered, and concentrated to furnish a dark brown gum. The gum was chromatographed on silica (ether/methanol, 9.5:0.5) to furnish the title compound as a dark brown solid (173 mg, 9%).

$^1$H NMR (CDCl$_3$): 7.88 (d, 2H, 2×ArCH, J 8.7 Hz), 7.49 (bs, 1H, phenolic hydroxyl), 6.82 (d, 2H, 2×ArCH, J 8.7 Hz), 4.46, 3.84 (2×appt, 2×2H, 2×ethoxy CH$_2$, Jvic 4.5 Hz), 3.74 (m, 2H, dioxolan CH$_2$), 3.66 (appt, 2H, dioxolan CH$_2$, Jvic 4.8 Hz);

LRMS (ESI): m/z 227 [M+H+]; C$_{11}$H$_{14}$O$_5$: 226.23.

Example 3

Preparation of 2-(2-hydroxyethoxy)-2-(3-bromo-4-hydroxy-5-methylphenyl)-1,3-dioxolane (Compound 3)

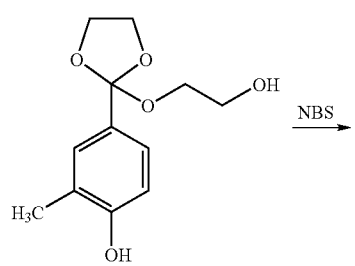

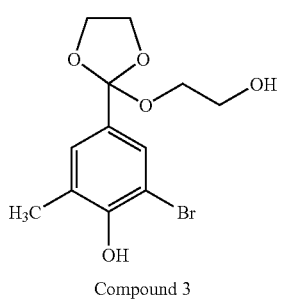

Compound 3

A mixture of compound 1 (109 mg; 0.4 mmol), N-bromosuccinamide (80 mg; 0.4 mmol) and AIBN (7.3 mg; 0.045 mmol) in dry carbon tetrachloride was refluxed for 5 hrs, TLC did not show any of the starting material. The reaction mixture was cooled to room temperature and then concentrated to dryness. The residue was dissolved in ethyl acetate (2×10 ml). The clear solution was washed with distilled water (5×10 ml), dried over anhydrous Na$_2$SO$_4$ and evaporated to dryness. This gave a 47% yield of compound 3.

$^1$H NMR (CDCl$_3$): 2.32 (s, 3H), 3.65 (t, 2H, J=4.4 Hz), 3.74 (t, 2H, J=4.3 Hz), 3.83 (t, 2H, J=4.7 Hz), 4.46 (t, 2H, J=4.8 Hz), 7.80 (s, 1H) and 8.02 (s, 1H).

Example 4

Preparation of 2-(4-Bromophenyl)-1,3-thiazolane (Compound 4)

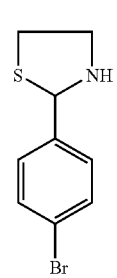

Compound 4

Melting Point Ref: UK patent GB2010827A.

To a solution of 4-bromobenzaldehyde (2.5 g, 13.5 mmol) in EtOH (15 ml) was added a solution of cysteamine HCl (0.5 g, 4.4 mmol) in water (5 ml) dropwise with stirring. The solution was then stirred at RT for 18 h before the bulk of the EtOH was removed by rotary evaporator. The residue was diluted with water (15 ml) and extracted with ether (3×20 ml) to remove excess aldehyde. The acidic aqueous layer was then basified with the slow addition of solid sodium carbonate (0.3 g) to give a heavy white precipitate, which was filtered and washed carefully with water (3×10 ml). The solid was dried in a vacuum desiccator to give 2-(4-bromophenyl)-1,3-thiazolane (4) as a white crystalline solid (0.73 g, 68%), mp 107° (lit. mp, 105-107°). $^1$H nmr (d$_6$-dmso, 300 MHz) 2.4, br s, NH; 3.05-3.2, m, H4,4,5; 3.5-3.6, m, H5; 5.55, s, H2; 7.38, d (8.4 Hz), ArH; 7.47, d (8.4), ArH. ESI (+ve) MS m/z 287/285 (M+MeCN+H, 30%), 246/244 (M+H, 100).

Example 5

Preparation of 2-(4-Methoxyphenyl)-1,3-thiazolane (Compound 5)

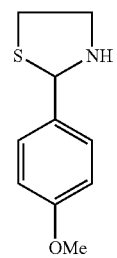

Compound 5

Melting Point Ref: U.S. Pat. No. 4,616,025

To a solution of p-methoxybenzaldehyde (1.81 g, 13.3 mmol) in ethanol (15 ml) was added dropwise a solution of cysteamine HCl (0.5 g, 4.4 mmol) in water (5 ml) and the solution stirred at RT for 18 h. The bulk of the ethanol was removed by rotary evaporator and the residue was diluted with water (15 ml) and extracted with diethyl ether (3×20 ml) to remove excess aldehyde. The aqueous layer was basified by addition of solid sodium carbonate (0.3 g) causing the product to precipitate out of solution. The precipitate was filtered, washed carefully with water (3×20 ml) and dried in a vacuum desiccator to give 2-(4-methoxyphenyl)-1,3-thiazolane (5) as a white solid (0.55 g, 69%), mp 94-95° (lit mp, 93-94°). $^1$H nmr (CDCl$_3$, 300 MHz) 2.51, s, NH; 3.05-3.20, m, H4,4,5; 3.64, m, H5; 3.80, s, OMe; 5.23, s, H2; 6.87, d (8.7 Hz), H3',5'; 7.44, d (8.7), H2',H6'. ESI (+ve) MS m/z 196 (M+H, 100%).

Example 6

Preparation of 4-(1,3-Thiazolidin-2-yl)benzonitrile (Compound 6)

Compound 6

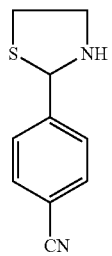

To a solution of 4-cyanobenzaldehyde (0.86 g, 6.6 mmol) in ethanol (15 ml) was added a solution of cysteamine HCl (0.5 g, 4.4 mmol) in water (5 ml) and the solution stirred at RT for 18 h. The bulk of the ethanol was removed by rotary evaporator and the residue was treated with water (15 ml) and extracted with diethyl ether (3×20 ml) to remove excess aldehyde. The aqueous layer was basified with solid sodium carbonate (0.3 g) resulting in the formation of an oil. The mixture was extracted with ether (2×25 ml), washed with brine (1×50 ml), dried (MgSO$_4$) and evaporated to give a clear oil that solidified on standing (0.62 g). Column chromatography (silica gel, 100% chloroform) afforded pure 4-(1,3-thiazolidin-2-yl)benzonitrile (6) (0.56 g, 67%) as clear oil that solidified on standing, mp 57-58°. $^1$H nmr (CDCl$_3$, 300 MHz) 3.05-3.15, m, H4,4; 3.2-3.35, m, H5; 3.4-3.5, m, H5; 5.64, s, H2; 7.63, app. s, H2',3',5',6'. ESI (+ve) MS m/z 191 (M+H, 100%).

Example 7

Preparation of 2-(4-Hydroxy-3-methoxyphenyl)-1,3-thiazolane (Compound 7)

Compound 7

Melting Point Ref: Chem. Pharm. Bull. 1988, 36, 1110-1116.

To a solution of vanillin (2.0 g, 13.2 mmol) in ethanol (15 ml) was added dropwise a solution of cysteamine HCl (0.5 g, 4.4 mmol) in water (5 ml) and the solution stirred at RT for 16.5 h. The bulk of the ethanol was removed by rotary evaporator and the residue was diluted with water (15 ml) and extracted with diethyl ether (3×20 ml) to remove excess aldehyde. The aqueous layer was basified by addition of solid sodium carbonate (0.3 g) causing the product to precipitate out of solution. The precipitate was filtered, washed carefully with water (3×20 ml) and dried in a vacuum desiccator to give 2-(4-hydroxy-3-methoxyphenyl)-1,3-thiazolane (7) as a white solid (0.62 g, 67%), mp 158-161° (lit mp, 182-183°). $^1$H nmr (d$_6$-dmso, 300 MHz) 2.8-3.0, m, H4,4,5; 3.12, br s, NH; 3.4-3.6, m, H5; 3.76, s, OMe; 5.34, s, H2; 6.70, d (8.0 Hz), H5'; 6.84, dd (1.8, 8.1 Hz), H6'; 7.04, d (1.8 Hz), H2'; 8.91, s, OH. ESI (+ve) MS m/z 212 (M+H, 100%).

Example 8

Preparation of 2-(3,4-Dimethoxyphenyl)-1,3-thiazolane (compound 8)

Compound 8

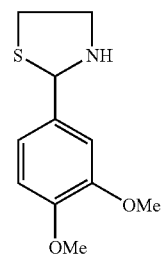

To a solution of 3,4-dimethoxybenzaldehyde (2.19 g, 13.2 mmol) in ethanol (15 ml) was added dropwise a solution of cysteamine HCl (0.5 g, 4.4 mmol) in water (5 ml) and the solution stirred at RT for 40 h. The bulk of the ethanol was removed by rotary evaporator and the residue was diluted with water (15 ml) and extracted with diethyl ether (3×20 ml) to remove excess aldehyde. The aqueous layer was basified with solid sodium carbonate (0.3 g) resulting in the formation of an oil. The mixture was extracted with ether (2×25 ml), washed with brine (1×50 ml), dried (MgSO$_4$) and evaporated to give a clear oil that solidified on standing (0.77 g). The material was triturated with hexane (3×5 ml) to give 2-(3,4-dimethoxyphenyl)-1,3-thiazolane (8) as a friable white solid (0.65 g, 66%), mp 54-56°.

$^1$H nmr (d$_6$-dmso, 300 MHz) 2.8-3.2, m, H4,4,5; 3.5, m, H5; 3.73, s, OMe; 3.74, s, Ome; 5.37, d (10.2 Hz), H2; 6.87, d (8.1 Hz), H5; 6.96, dd (1.7, 8.1 Hz), H6; 7.06, d (1.5 Hz), H2. ESI (+ve) MS m/z 226 (M+H, 100%).

Example 9

Preparation of Methyl 4-[2-(4-fluorophenyl)-1,3-dioxolan-2-yl]butanoate (compound 9)

Compound 9

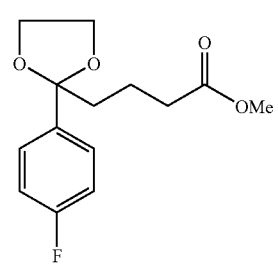

Methyl 5-(4-fluorophenyl)-5-oxopentanoate

To a solution of 5-(4-fluorophenyl)-5-oxopentanoic acid (3.0 g, 14.3 mmol) in dry MeOH (50 ml) was added concentrated sulfuric acid (50 mg) and the mixture refluxed under nitrogen for 16 h. The bulk of the MeOH was removed by rotary evaporator and the residue treated with sodium bicarbonate solution (5%, 100 ml) and extracted with ethyl acetate (3×50 ml). The organic extract was washed with water (1×100 ml), brine (1×100 ml), dried (Na$_2$SO$_4$) and evaporated to give methyl 5-(4-fluorophenyl)-5-oxopentanoate (2.69 g, 84%) as a white crystalline solid.

Methyl 4-[2-(4-fluorophenyl)-1,3-dioxolan-2-yl]butanoate (9)

To a solution of 5-(4-fluorophenyl)-5-oxopentanoate (2.26 g, 10 mmol) in toluene (60 ml) was added ethylene glycol (1.95 ml, 35 mmol) and p-toluenesulfonic acid monohydrate (60 mg, 0.32 mmol) and the mixture refluxed in a Dean-Stark apparatus under nitrogen for 17 h. The toluene was removed by rotary evaporator and the residue treated with sodium bicarbonate solution (5%, 50 ml) and extracted with ether (2×50 ml). The ether extract was washed with brine (1×50 ml), dried (Na$_2$SO$_4$) and evaporated to give methyl 4-[2-(4-fluorophenyl)-1,3-dioxolan-2-yl]butanoate (9) as a pale yellow oil (2.47 g, 91%). $^1$H nmr (CDCl$_3$, 300 MHz) 1.6-1.7, m, H3; 1.9, m, H4; 2.30, t (7.5 Hz), H2; 3.64, s, OMe; 3.7-3.8, m, CH$_2$O; 3.95-4.05, m, CH$_2$O; 7.01, m, H3',5'; 7.41, m, H2',6'. ESI (+ve) MS m/z 269 (M+H, 45%).

Example 10

Preparation of 4-[2-(4-Fluorophenyl)-1,3-dioxolan-2-yl]butan-1-ol (Compound 10)

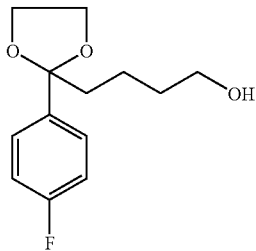

Compound 10

To a suspension of lithium aluminium hydride (0.167 g, 4.4 mmol) in dry tetrahydrofuran (10 ml) was added dropwise a solution of methyl 4-[2-(4-fluorophenyl)-1,3-dioxolan-2-yl]butanoate (9) (0.50 g, 1.86 mmol) in dry tetrahydrofuran (10 ml) with stirring under nitrogen. Once the addition was complete stirring was continued at RT for 2 h following by refluxing under nitrogen for 1 h. Water was cautiously added to destroy excess hydride then the reaction mixture tipped into sodium carbonate solution (1.7%, 150 ml) and extracted with ethyl acetate (2×50 ml). The ethyl acetate extract was washed with brine (1×50 ml), dried (Na$_2$SO$_4$) and evaporated to give a yellow oil (0.394 g). Purification by column chromatography (silica gel, 80:3 chloroform/n-propanol) afforded 4-[2-(4-fluorophenyl)-1,3-dioxolan-2-yl]butan-1-ol (10) (0.252 g, 56%) as a clear colourless oil. $^1$H nmr (CDCl$_3$, 300 MHz) 1.35-1.50, m, H3; 1.55, quin (6.9 Hz), H2; 1.90, m, H4; 3.60, m, H1; 3.76, m, CH$_2$O; 4.01, m, CH$_2$O; 7.01, m, H3',5'; 7.41, m, H2',6'. ESI (+ve) MS m/z 179 (M-C$_2$H$_5$O$_2$, 90%).

Example 11

Preparation of 2-(4'-Bromophenyl)-2-butyl-1,3-dioxolane (Compound 11)

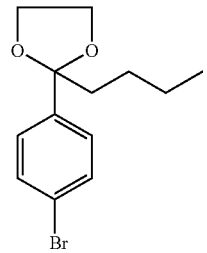

Compound 11

To a solution of 4'-bromovalerophenone (2.41 g, 10 mmol) in benzene (60 ml) was added ethylene glycol (2.0 ml, 36 mmol), p-toluenesulfonic acid monohydrate (100 mg, 0.53 mmol) and the mixture refluxed under nitrogen in a Dean-Stark apparatus for 16 h. The reaction mixture was washed with sodium bicarbonate solution (5%, 50 ml), brine (1×50 ml), dried (Na$_2$SO$_4$) and evaporated to give 2-(4-bromophenyl)-2-butyl-1,3-dioxolane (11) as a clear oil (2.61 g, 92%). $^1$H nmr (CDCl$_3$, 300 MHz) 0.88, t (6.9 Hz), H4''; 1.2-1.4, m, H2'',3''; 1.88, m, H1''; 3.7-3.8, m, CH$_2$O; 4.0-4.1, m, CH$_2$O; 7.34, d (8.4 Hz), H2',6'; 7.49, d (8.4 Hz), H3',5'. ESI (+ve) MS m/z 285/287 (M+H, 8%).

Example 12

Preparation of 4-(4-Methoxyphenyl)-1-(3-methylbutyl)-1H-pyrazole (Compound 12)

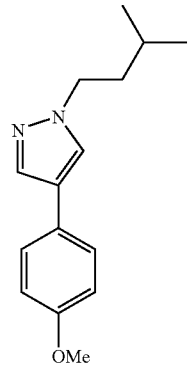

Compound 12

To p-bromoanisole (0.25 g, 1.33 mmol) was added a solution of 1-(3-methylbutyl)-4-(4,4,5,5-tetramethyl-1,3,2-dioxaborolan-2-yl)-1H-pyrazole (0.41 g, 1.55 mmol) in tetrahydrofuran (10 ml), potassium carbonate (0.29 g, 2.1 mmol) and [1,1-bis(diphenylphosphino)ferrocene]dichloropalladium (II) (12 mg, 0.023 mmol) and the mixture refluxed under nitrogen for 17 h. Water (50 ml) was added to the reaction mixture and stirring continued at RT for 15 min followed by extraction with ether (2×50 ml), drying (MgSO$_4$) and evaporation of the ether extract to give a brown oil (0.414 g). Purification by column chromatography (silica gel, 100% chloroform) afforded 4-(4-methoxyphenyl)-1-(3-methylbutyl)-1H-pyrazole (12) as a waxy pale yellow solid (37 mg, 11%). $^1$H nmr (CDCl$_3$, 300 MHz) 0.97, d (6.6 Hz), 2×Me; 1.64, sept (6.6 Hz), H3''; 1.80, dt (7.2 Hz), H2''; 3.82, s, OMe;

4.15, t (7.5 Hz), H1"; 6.90, d (8.7 Hz), H3',5'; 7.39, d (8.7 Hz), H2',6'; 7.54, s, H3 or H5; 7.69, s, H5 or H3. ESI (+ve) MS m/z 245 (M+H, 100%).

Example 13

Preparation of 1-(3-Methylbutyl)-4-(4-methylphenyl)-1H-pyrazole (Compound 13)

Compound 13

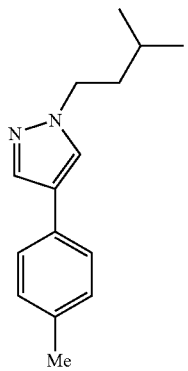

To a solution of p-bromotoluene (0.66 g, 3.86 mmol) in tetrahydrofuran (20 ml) was added a solution of 1-(3-methylbutyl)-4-(4,4,5,5-tetramethyl-1,3,2-dioxaborolan-2-yl)-1H-pyrazole (0.41 g, 1.55 mmol) in tetrahydrofuran (10 ml), potassium carbonate (0.42 g, 3.0 mmol), [1,1-bis(diphenylphosphino)ferrocene]dichloropalladium (II) (40 mg, 0.077 mmol) and water (40 µl) and the mixture refluxed under nitrogen for 43 h. Water (50 ml) was added to the reaction mixture and stirring continued at RT for 10 min followed by extraction with ether (2×50 ml). The ether extract was then dried (MgSO$_4$) and evaporated to give a brown oil (0.56 g) that solidified on standing. Purification by column chromatography (silica gel, 100% chloroform) afforded 1-(3-methylbutyl)-4-(4-methylphenyl)-1H-pyrazole (13) as a waxy pale yellow solid (0.216 g, 53%). $^1$H nmr (CDCl$_3$, 300 MHz) 0.97, d (6.3 Hz), 2×Me; 1.62, m, H3"; 1.80, dt (7.3 Hz), H2"; 2.35, s, 4'-Me; 4.16, t (7.5 Hz), H1"; 7.16, d (8.1 Hz), H3',5'; 7.37, d (8.1 Hz), H2',6'; 7.59, s, H3 or H5; 7.74, s, H5 or H3. ESI (+ve) MS m/z 229 (M+H, 100%).

Example 14

Preparation of 2,6-Dimethoxy-3-[4-(trifluoromethoxy)phenyl]pyridine (Compound 14)

Compound 14

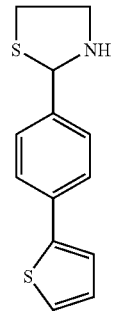

To a solution of 1-bromo-4-(trifluoromethoxy)benzene (0.92 g, 3.86 mmol) in tetrahydrofuran (20 ml) was added a solution of 2,6-dimethoxy-3-(4,4,5,5-tetramethyl-1,3,2-dioxaborolan-2-yl)pyridine (0.40 g, 1.50 mmol) in tetrahydrofuran (10 ml), potassium carbonate (0.42 g, 3.0 mmol), [1,1-bis(diphenylphosphino)ferrocene]dichloropalladium (II) (40 mg, 0.077 mmol) and water (40 µl) and the mixture refluxed under nitrogen for 43 h. Water (50 ml) was added to the reaction mixture and stirring continued at RT for 10 min followed by extraction with ether (2×50 ml). The ether extract was then dried (MgSO$_4$) and evaporated to give a dark mobile oil (0.504 g). Purification by column chromatography (silica gel, 3:1 hexane/dichloromethane) afforded 2,6-dimethoxy-3-[4-(trifluoromethoxy)phenyl]pyridine (14) as a clear, colourless oil (0.372 g, 83%). $^1$H nmr (CDCl$_3$, 300 MHz) 3.97, s, 2×OMe; 6.40, d (8.1 Hz), H5; 7.24, d (8.4 Hz), H3',5'; 7.55, m, H2,2',6'. ESI (+ve) MS m/z 300 (M+H, 100%).

Example 15

Preparation of 2-[4-(2-Thienyl)phenyl]-1,3-thiazolane (Compound 15)

Compound 15

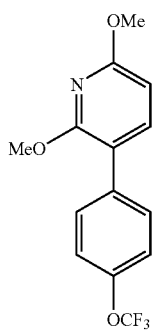

To a solution of 4-(2-thienyl)benzaldehyde (500.0 mg, 2.66 mmol) in EtOH (5.0 mL) was added a solution of cysteamine HCl (101.0 mg, 0.89 mmol) in water (2.0 mL) dropwise with stirring. The solution was then stirred at room temperature for 18 hours before the bulk of the EtOH was removed by rotary evaporator. The resulting residue was diluted with water (15.0 mL) and extracted with ether (3×30.0 mL) to remove excess aldehyde. The acidic aqueous layer was then basified with the slow addition of solid sodium carbonate (300.0 mg) to afford a white precipitate, which was filtered and washed carefully with water (3×20.0 mL). The solid was dried under reduced pressure to afford 2-[4-(2-thienyl)phenyl]-1,3-thiazolane (15) as a yellow powder (30 mg, 4.6%). $^1$H nmr (CDCl$_3$, 300 MHz) 3.14, m, H4,4,5; 3.64, m, H5; 5.95, s, H2; 7.08, m, thienyl-H; 7.31, m, 2×thienyl-H; 7.50, d (8.1 Hz), 2×phenyl-H; 7.59, d (8.4 Hz), 2×phenyl-H. ESI (+ve) MS m/z 248 (M+H, 100%).

Example 16

Preparation of 2-Ethyl-2-(4-methoxyphenyl)-1,3-dioxolane (Compound 16)

Compound 16

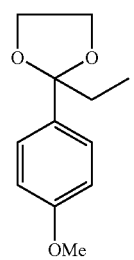

4'-Methoxypropiophenone

To a solution of 4'-hydroxypropiophenone (1.0 g, 6.67 mmol) in acetonitrile (50.0 mL) was added potassium carbonate (7.17 g, 66.7 mmol) and the mixture heated to reflux for 90 min. After this time the reaction mixture was allowed to cool to room temperature and dimethyl sulphate (1.05 mL, 11.1 mmol) was added and the reaction mixture was heated to reflux for a further 19 h. After cooling the acetonitrile was evaporated under reduced pressure and the residue taken up in water and extracted with dichloromethane. The dichloromethane extract was dried (MgSO$_4$) and evaporated under reduced pressure to give 4'-methoxypropiophenone as a yellow oil, (970 mg, 89%) $^1$H nmr (d$_6$-DMSO, 300 MHz) 1.06, t (7.2 Hz), CH$_3$; 2.95, q (7.2 Hz), CH$_2$; 3.83, s, OMe; 7.02, d (6.9 Hz), H3',5'; 7.93, d (6.9 Hz), H2',6'. ESI (+ve) MS m/z 165 (M+H, 100%).

2-Ethyl-2-(4-methoxyphenyl)-1,3-dioxolane (16)

To a solution of 4'-methoxypropiophenone (250.0 mg, 1.52 mmol) in toluene (20.0 mL) was added ethylene glycol (255.0 µL, 4.57 mmol) and p-toluenesulfonic acid monohydrate (13.0 mg, 0.04 mmol) and the reaction mixture refluxed overnight using a Dean-Stark apparatus. The reaction mixture was cooled to room temperature, then washed with saturated aqueous sodium bicarbonate solution followed by water. The toluene solution was then dried (MgSO$_4$) and evaporated under reduced pressure to afford 2-ethyl-2-(4-methoxyphenyl)-1,3-dioxolane (16) as a yellow oil (184 mg, 58%). $^1$H nmr (CDCl$_3$, 300 MHz) 0.76, t (6.6 Hz), CH$_3$; 1.78, q (6.9 Hz), CH$_2$; 3.65, m, CH$_2$O, 3.73, s, 4'-OMe; 3.95, m, CH$_2$O; 6.88, d (7.2 Hz), H3',5'; 7.02, d, (7.5 Hz), H2',6'. ESI (+ve) MS m/z 209 (M+H, 100%).

Example 17

Preparation of 2-Hexyl-2-(4-methylphenyl)-1,3-dithiolane (Compound 17)

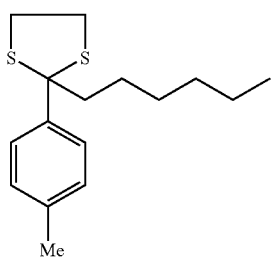

Compound 17

α-Hexyl-4-methyl-benzenemethanol (Ref: Liang, X.; Bols, M. *J. Chem. Soc., Perkin Trans. 1* 2002, 503-508.)

1-Iodohexane was added dropwise to a stirred suspension of magnesium turnings (987 mg, 40.6 mmol, 2.0 equiv.) in anhydrous diethyl ether (40 mL), cooled in an ice-water bath and under an atmosphere of dry nitrogen. The addition was followed by a vigorous exotherm after which a cloudy suspension resulted. Stirring was continued at ambient temperature for 2 hours before recooling to 0° C. 4-Tolualdehyde (1.21 mL, 10.2 mmol, 0.5 eq.) was added dropwise and the reaction mixture was stirred at ambient temperature for 2 hours prior to careful quenching with saturated aqueous ammonium chloride solution (20 mL). The biphasic mixture was stirred for 10 minutes, the organic phase was isolated and the aqueous phase was twice extracted with diethyl ether. The organic phases were combined, dried over anhydrous magnesium sulfate and concentrated in vacuo to afford a colourless oil which was purified by flash chromatography on silica gel, eluting with hexane-ethyl acetate (4:1) to give the desired benzylic alcohol (2.10 g, 100%). $^1$H nmr (200 MHz, CDCl$_3$) 0.83-1.79 (m, 13H, (CH$_2$)$_5$CH$_3$), 2.34 (s, 3H, ArCH$_3$), 4.61 (t, J=3.8 Hz, 2H, CHOH), 7.14 (d, J=4.0 Hz, 2H, 2×ArH), 7.23 (d, J=4.2 Hz, 2H, 2×ArH).

1-(4-Methylphenyl)-1-heptanone

To a stirred solution of α-hexyl-4-methyl-benzenemethanol (2.10 g, 10.2 mmol.) in anhydrous dichloromethane (45 mL) under an atmosphere of dry nitrogen was added pyridinium chlorochromate (3.08 g, 14.3 mmol., 1.4 eq.). Stirring was continued at room temperature for 3 hours after which time analysis by thin layer chromatography revealed complete conversion of the starting alcohol. Following evaporation of the reaction solvent the desired ketone (1.929 g, 93%) was isolated by flash chromatography on silica gel, eluting with hexane-ethyl acetate (4:1). $^1$H nmr (200 MHz, CDCl$_3$) 0.86-1.76 (m, 3H, (CH$_2$)$_5$CH$_3$), 2.41 (s, 3H, ArCH$_3$), 2.93 (t, J=3.6 Hz, 2H, COCH$_2$), 7.25 (d, J=4.2 Hz, 2H, 2×ArH), 7.86 (d, J=4.2 Hz, 2H, 2×ArH).

2-Hexyl-2-(4-methylphenyl)-1,3-dithiolane (17)

(Ref: Banik et al. Tetrahedron Lett. 2001, 42, 4425-4427.)

To a stirred solution of 1-(4-methylphenyl)-1-heptanone (500 mg, 2.45 mmol) and 1,2-ethanedithiol (250 µL, 2.94 mmol., 1.2 eq.) in anhydrous tetrahydrofuran (5.0 mL) under an atmosphere of dry nitrogen was added iodine (62 mg, 0.245 mmol., 0.10 eq.). The reaction mixture was stirred at ambient temperature for several days after which time analysis by thin layer chromatography revealed a mixture of starting material and a new less polar compound which stained positively towards phosphomolybdic acid. Evaporation of the solvent gave a strong smelling crude oil which was purified by flash chromatography on silica gel, eluting with hexane-dichloromethane (2:1) to afford the desired dithiolane (17; 300 mg, 44% isolated) as a colourless oil. $^1$H nmr (200 MHz, CDCl$_3$) 0.80-0.86 (m, 3H, CH$_2$CH$_3$), 1.21-1.29 [m, 10H, (CH$_2$)$_5$], 2.32 (s, 3H, ArCH$_3$), 3.16-3.41 (m, 4H, SCH$_2$), 7.01 (d, J=4.0 Hz, 2H, 2×ArH), 7.56 (d, J=4.1 Hz, 2H, 2×ArH).

Example 18

Preparation of 2-Methyl-2-(4-methylphenyl)-1,3-dithiolane (compound 18)

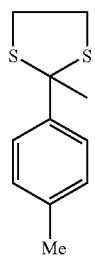

Compound 18

(Ref: Banik et al. *Tetrahedron Lett.* 2001, 42, 4425-4427.)

To a stirred solution of the 4-methylacetophenone (1.34 mL, 10.0 mmol) and 1,2-ethanedithiol (838 μL, 10.0 mmol., 1.0 eq.) in anhydrous tetrahydrofuran (20.0 mL) under an atmosphere of dry nitrogen was added iodine (253 mg, 1.0 mmol., 0.10 equiv.). The reaction mixture was stirred at ambient temperature for five days after which time analysis by thin layer chromatography revealed a mixture of starting material and a new less-polar compound which stained positively towards phosphomolybdic acid. Evaporation of the solvent gave a strong smelling crude oil which was purified by flash chromatography on silica gel, eluting with hexane-ethyl acetate (4:1) to afford the desired dithiolane (558 mg, 27% isolated) as a pale yellow oil (a low melting solid). $^1$H nmr (200 MHz, CDCl$_3$) 2.14 (s, 3H, CH$_3$), 2.33 (s, 3H, ArCH$_3$), 3.32-3.53 (m, 4H, SCH$_2$CH$_2$S), 7.12 (d, J=8.5 Hz, 2H, 2×ArH), 7.63 (dd, J=8.5, 1.9 Hz, 2H, 2×ArH).

Example 19

Preparation of 2-Hexyl-2-(4-methylphenyl)-1,3-dioxolane (compound 19)

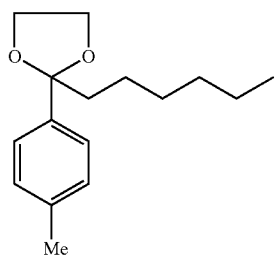

Compound 19

(Ref: A. Srikishna and R. Viswajanani, Tetrahedron, 1995, 51, 3339.)

A mixture of 1-(4-methylphenyl)-1-heptanone (200 mg, 0.980 mmol), p-toluenesulfonic acid (17 mg, 0.098 mmol) and ethylene glycol (0.16 mL, 2.9 mmol) in dry toluene (10 mL) was heated at reflux with a Dean-Stark apparatus under nitrogen for 24 h. The mixture was allowed to cool to room temperature and the solvent was evaporated in vacuo. The residue was taken up in ether (20 mL) and the solution was washed with saturated sodium carbonate solution (2×10 mL) and brine (1×10 mL), then dried (Na$_2$SO$_4$) and concentrated under reduced pressure. Flash column chromatography of the residue, eluting with dichloromethane/hexane (1:2) afforded 2-hexyl-2-(4-methylphenyl)-1,3-dioxolane (19) as a tan-coloured oil (162 mg, 67%). $^1$H nmr (200 Mz, CDCl$_3$) 0.80-0.92 (m, 3H, CH$_2$CH$_3$), 1.18-1.40 [m, 8H, (CH$_2$)$_4$], 1.84-1.89 (m, 2H, CCH$_2$), 2.34 (s, 3H, ArCH$_3$), 3.73-3.81 (m, 2H, OCH$_2$), 3.94-4.02 (m, 2H, OCH$_2$), 7.13 (d, J=8.2 Hz, 2H, 2×ArH), 7.32 (d, J=8.2 Hz, 2H, 2×ArH).

Example 20

Preparation of 2-(4-Chlorophenyl)-2-methyl-1,3-dioxane (Compound 20)

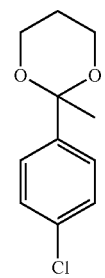

Compound 20

(Ref. B. Karimi, G. R. Ebrahimian and H. Sheradj, *Org. Lett.*, 1999, 1, 1737.)

To a stirred mixture of 4-chloroacetophenone (1.3 mL, 10 mmol), triethylformate (2.0 mL, 12 mmol), 1,3-propanediol (2.2 mL, 30 mmol) and dry methanol (1.2 mL) in dry CH$_2$Cl$_2$ (50 mL) was added NBS (53 mg, 0.30 mmol). The mixture was protected from light and stirred at room temperature under an inert atmosphere of nitrogen for 70 h. After the mixture was washed with saturated aqueous sodium bicarbonate solution (20 mL), the aqueous phase was extracted with dichloromethane (3×30 mL). The combined organic solution was washed with water (2×20 mL), brine (1×20 mL), then dried (Na$_2$SO$_4$) and concentrated under reduced pressure. Flash column chromatography of the residue, eluting with 37% aqueous ammonia:ether:hexane (0.02:1:6) afforded 2-(4-chlorophenyl)-2-methyl-1,3-dioxane (20) as a colourless oil (1.1 g, 52%). $^1$H nmr (200 MHz, CDCl$_3$) 1.49 (s, 3H, CH$_3$), 1.98-2.25 (m, 2H, OCH$_2$CH$_2$CH$_2$O), 3.65-4.10 (m, 4H, OCH$_2$CH$_2$CH$_2$O), 7.30-7.50 (m, 4H, 4×ArH).

Example 21

Preparation of 2-(4-Chlorophenyl)-2-methyl-1,3-dioxolane (compound 21)

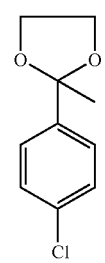

Compound 21

To a stirred mixture of 4-chloroacetophenone (1.3 mL, 10 mmol), triethylformate (2.0 mL, 12 mmol), ethylene glycol (1.7 mL, 30 mmol) and dry methanol (1.2 mL) in dry dichloromethane (50 mL) was added NBS (53 mg, 0.30 mmol). The mixture was protected from light and stirred at room temperature under an inert atmosphere of nitrogen for 70 h. After the mixture was washed with saturated sodium bicarbonate solution (20 mL), the aqueous phase was extracted with dichloromethane (3×30 mL). The combined organic solution was washed with water (2×20 mL), brine (1×20 mL), then dried (Na$_2$SO$_4$) and concentrated under reduced pressure. Flash column chromatography of the residue, eluting with 37% aqueous ammonia:ether:hexane (0.02:1:6) afforded 2-(4-chlorophenyl)-2-methyl-1,3-dioxolane (21) as a colourless oil (1.1 g, 51%). $^1$H nmr (300 MHz, CDCl$_3$) 1.63 (s, 3H, CH$_3$), 3.72-3.82 (m, 2H, OCH$_2$), 3.98-4.09 (m, 2H, OCH$_2$), 7.42 (d, J=8.6 Hz, 2H, 2×ArH), 7.30 (d, J=8.6 Hz, 2H, 2×ArH).

Example 22

Preparation of 2-Methyl-2-(4-methylphenyl)-1,3-dioxane (compound 22)

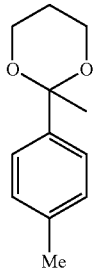

Compound 22

To a stirred mixture of 4-methylacetophenone (1.3 mL, 10 mmol), triethylformate (2.0 mL, 12 mmol), 1,3-propanediol (2.2 mL, 30 mmol) and dry methanol (1.2 mL) in dry dichloromethane (50 mL) was added NBS (53 mg, 0.30 mmol). The mixture was protected from light and stirred at room temperature under an inert atmosphere of nitrogen for 70 h. After the mixture was washed with saturated sodium bicarbonate solution (20 mL), the aqueous phase was extracted with dichloromethane (3×30 mL). The combined organic solution was washed with water (2×20 mL), brine (1×20 mL), then dried (Na$_2$SO$_4$) and concentrated under reduced pressure. Flash column chromatography of the residue, eluting with 37% aqueous ammonia:ether:hexane (0.02:1:6) afforded 2-methyl-2-(4-methylphenyl)-1,3-dioxane (22) as a colourless oil (480 mg, 24%). $^1$H nmr (200 MHz, CDCl$_3$) 1.50 (s, 3H, CH$_3$), 1.96-2.25 (m, 2H, OCH$_2$CH$_2$CH$_2$O), 2.37 (s, 3H, ArCH$_3$), 3.70-4.00 (m, 4H, OCH$_2$CH$_2$CH$_2$O), 7.23 (d, J=8.3 Hz, 2H, 2×ArH), 7.33 (d, J=8.3 Hz, 2H, 2×ArH).

Example 23

Preparation of 2-Methyl-2-(4-methylphenyl)-1,3-dioxolane (compound 23)

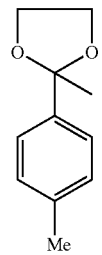

Compound 23

A mixture of 4-methylacetophenone (1.00 g, 7.45 mmol), p-toluenesulfonic acid (133 mg, 0.745 mmol) and ethylene glycol (1.20 mL, 22.4 mmol) in dry toluene (20 mL) was heated at reflux with a Dean-Stark apparatus under nitrogen for 24 h. The mixture was allowed to cool to room temperature and the solvent was evaporated in vacuo. The residue was taken up in ether (20 mL) and the solution was washed with saturated sodium bicarbonate solution (2×10 mL) and brine (1×10 mL), then dried (Na$_2$SO$_4$) and concentrated under reduced pressure. Flash column chromatography of the residue, eluting with 37% aqueous ammonia:ether:hexane (0.02: 1:6) afforded 2-methyl-2-(4-methylphenyl)-1,3-dioxolane (23) as a colourless oil (1.05 g, 59%). $^1$H nmr (200 MHz, CDCl$_3$) 1.65 (s, 3H, CH$_3$), 2.35 (s, 3H, ArCH$_3$), 3.74-3.86 (m, 2H, OCH$_2$), 3.94-4.06 (m, 2H, OCH$_2$), 7.15 (d, J=8.2 Hz, 2H, 2×ArH), 7.37 (d, J=8.2 Hz, 2H, 2×ArH).

Example 24

Preparation of 2-(4-Chlorophenyl)-2-methyl-1,3-dithiolane (compound 24)

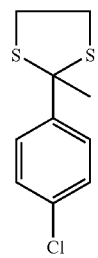

Compound 24

(Ref. S. Samajdar, M. K. Basu, F. F. Becker and B. K. Banik, *Tetrahedron Lett.*, 2001, 42, 4425.)

A mixture of 4-chloroacetophenone (1.3 mL, 10 mmol), iodine (250 mg, 1 mmol), 1,2-ethanedithiol (0.85 mL, 10 mmol) in dry tetrahydrofuran (20 mL) was heated at reflux under an atmosphere of nitrogen for 16 h. The mixture was allowed to cool to room temperature and concentrated in vacuo and the residue taken up in ether (20 mL). The organic solution was washed with water (2×10 mL) and brine (1×10 mL), then dried (Na$_2$SO$_4$) and evaporated under reduced pressure. Flash column chromatography of the residue, eluting with 37% aqueous ammonia:ether:hexane (0.02:1:6) afforded 2-(4-chlorophenyl)-2-methyl-1,3-dithiolane (24) as a colourless oil (1.11 g, 48%). $^1$H nmr (300 MHz, CDCl$_3$) 2.13 (s, 3H, CH$_3$), 3.31-3.53 (m, 4H, SCH$_2$CH$_2$S), 7.27 (d, J=8.7 Hz, 2H, 2×ArH), 7.69 (d, J=8.7 Hz, 2H, 2×ArH).

Example 25

Preparation of 2-(4-Nitrophenyl)-2-methyl-1,3-dioxolane (compound 25)

Compound 25

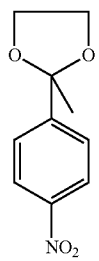

A mixture of 4-nitroacetophenone (1.65 g, 10.0 mmol), p-toluenesulfonic acid (172 mg, 1.00 mmol) and ethylene glycol (1.7 mL, 30 mmol) in dry toluene (20 mL) was heated at reflux with a Dean-Stark apparatus under nitrogen for 24 h. The mixture was allowed to cool to room temperature and the solvent was evaporated in vacuo. The residue was taken up in ether (20 mL) and the solution was washed with saturated sodium bicarbonate solution (2×10 mL) and brine (1×10 mL), then dried ($Na_2SO_4$) and concentrated under reduced pressure. Recrystallisation from ether and hexanes afforded 2-(4-nitrophenyl)-2-methyl-1,3-dioxolane (25) as a pale yellow crystals (1.52 g, 73%; yield based from the first crop of crystals). $^1$H nmr (300 MHz, $CDCl_3$) 1.66 (s, 3H, $CH_3$), 3.71-3.83 (m, 2H, $OCH_2$), 4.02-4.13 (m, 2H, $OCH_2$), 7.63-7.73 (d, J=8.8 Hz, 2H, 2×ArH), 8.16-8.26 (d, J=8.8 Hz, 2H, 2×ArH).

Example 26

Preparation of 2-(4-Nitrophenyl)-2-methyl-1,3-dioxane (compound 26)

Compound 26

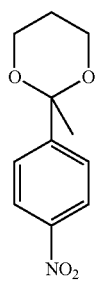

A mixture of 4-nitroacetophenone (1.65 g, 10.0 mmol), p-toluenesulfonic acid (172 mg, 1.00 mmol) and 1,3-propanediol (2.3 mL, 30 mmol) in dry toluene (20 mL) was heated at reflux with a Dean-Stark apparatus under nitrogen for 24 h. The mixture was allowed to cool to room temperature and the solvent was evaporated in vacuo. The residue was taken up in ether (20 mL) and the solution was washed with saturated sodium bicarbonate solution (2×10 mL) and brine (1×10 mL), then dried ($Na_2SO_4$) and concentrated under reduced pressure. Recrystallisation from ether and hexane afforded 2-(4-nitrophenyl)-2-methyl-1,3-dioxane (26) as a pale yellow crystals (1.60 g, 72%; yield based from the first crop of crystals). $^1$H nmr (300 MHz, $CDCl_3$) 1.52 (s, 3H, $CH_3$), 2.08-2.22 (m, 2H, $OCH_2CH_2CH_2O$), 3.65-3.80 (m, 2H, $OCH_2$), 3.88-4.00 (m, 2H, $OCH_2$), 7.63 (d, J=8.9 Hz, 2H, 2×ArH), 8.26 (d, J=8.9 Hz, 2H, 2×ArH).

Example 27

Preparation of 2-(4-Methoxyphenyl)-1,3-oxathiolane (compound 27)

Compound 27

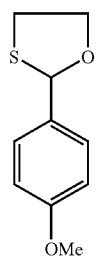

A mixture of anisaldehyde (273 mg, 2.00 mmol), freshly distilled 2-mercaptoethanol (625 mg, 8.00 mmol), sodium sulfate (852 mg, 6.00 mmol) and freshly fused zinc chloride (818 mg, 6.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried ($Na_2SO_4$), filtered and the solvent removed in vacuo to give a colourless oil (528 mg). To 260 mg of the oil were added toluene (20 ml) and p-toluenesulfonic acid monohydrate (5 mg, 26 μmol) and the mixture was refluxed for 3 h. After cooling the toluene was removed in vacuo and the residual oil subjected to flash chromatography (ether/hexane gradient) to give 2-(4-methoxyphenyl)-1,3-oxathiolane (27) (74 mg, 39%) as a colourless oil. $^1$H nmr ($d_6$-dmso, 300 MHz) δ 3.18 (m, 2H); 3.81 (m, 1H); 4.45 (m, 1H); 5.98, (s, 1H); 6.90 (d, J 8.7 Hz, 2H); 7.36 (d, J 8.7 Hz, 2H). ESI (+ve) MS m/z 197 (M+H, 100%).

Example 28

Preparation of 2-(3,4,5-Trimethoxyphenyl)-1,3-oxathiolane (compound 28)

Compound 28

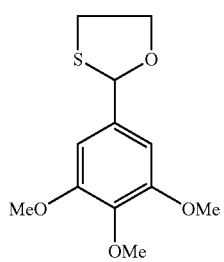

A mixture of 3,4,5-trimethoxybenzaldehde (393 mg, 2.00 mmol), freshly distilled 2-mercaptoethanol (469 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (513 mg). To the oil was added toluene (20 ml), p-toluenesulfonic acid monohydrate (5 mg, 26 μmol) and the mixture was refluxed for 2 h. After cooling, the toluene was removed in vacuo and the residual oil subjected to flash chromatography (ether/hexane gradient) to give 2-(3,4,5-trimethoxyphenyl)-1,3-oxathiolane (28) (174 mg, 34%) as a colourless oil. $^1$H nmr (d$_6$-dmso, 300 MHz) δ 3.17 (m, 2H); 3.64 (s, 3H); 3.75 (s, 6H); 3.84 (m, 1H); 4.48 (m, 1H); 5.98, (s, 1H); 6.72 (s, 2H). ESI (+ve) MS m/z 257 (M+H, 100%).

Example 29

Preparation of
2-Methoxy-4-(1,3-oxathiolan-2-yl)phenol
(compound 29)

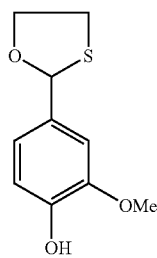

Compound 29

A mixture of vanillin (304 mg, 2.00 mmol), freshly distilled 2-mercaptoethanol (469 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (507 mg). To the oil was added toluene (20 ml) and p-toluenesulfonic acid monohydrate (6 mg, 31 μmol) and the mixture was refluxed for 1 h. After cooling the toluene was removed in vacuo and the residual oil subjected to flash chromatography (ether/hexane gradient) to give 2-methoxy-4-(1,3-oxathiolan-2-yl)phenol (29) (34 mg, 8%) as a colourless oil which solidified upon standing. $^1$H nmr (d$_6$-dmso, 300 MHz) δ 3.17 (m, 2H); 3.74 (s, 3H); 3.78 (m, 1H); 4.45 (m, 1H); 5.93, (s, 1H); 6.72 (d, J 7.8 Hz, 1H); 6.84 (dd, J 7.8, 1.8 Hz, 1H); 6.97 (d, J 1.8 Hz, 1H). ESI (+ve) MS m/z 213 (M+H, 65%).

Example 30

Preparation of 4-(1,3-Oxathiolan-2-yl)benzonitrile
(compound 30)

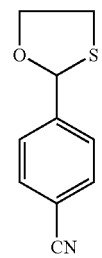

Compound 30

A mixture of 4-cyanobenzaldehyde (262 mg, 2.00 mmol), freshly distilled 2-mercaptoethanol (469 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (512 mg). To the oil was added toluene (25 ml) and p-toluenesulfonic acid monohydrate (6 mg, 31 μmol) and the mixture was refluxed for 1 h. After cooling, the toluene was removed in vacuo and the residual oil subjected to flash chromatography (ether/hexane gradient) to give 4-(1,3-oxathiolan-2-yl)benzonitrile (30) (106 mg, 28%) as a colourless oil. $^1$H nmr (d$_6$-dmso, 300 MHz) δ 3.20 (m, 2H); 3.92 (m, 1H); 4.49 (m, 1H); 6.16, (s, 1H); 7.59 (d, J 8.1 Hz, 2H); 7.82 (d, J 8.1 Hz, 2H).

Example 31

Preparation of
2-(4-Bromophenyl)-2-ethyl-1,3-oxathiolane
(compound 31)

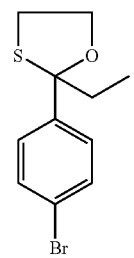

Compound 31

A mixture of p-bromopropiophenone (426 mg, 2.00 mmol), freshly distilled 2-mercaptoethanol (469 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (560 mg). The oil was subjected to flash chromatography (ether/hexane gradient) to give 2-(4-bromophenyl)-2-ethyl-1,3-oxathiolane (31) (214 mg, 39%) as a colourless oil. $^1$H nmr (d$_6$-dmso, 300 MHz) δ 0.77 (t, J 7.2 Hz, 3H); 2.05 (q, J 7.2 Hz, 2H); 3.07 (m, 2H); 3.86 (m, 1H); 4.30 (m, 1H); 7.31 (d, J 8.7 Hz, 2H); 7.51 (d, J 8.4 Hz, 2H).

Example 32

Preparation of 4-(5-Methyl-1,3-oxathiolan-2-yl)benzonitrile (compound 32)

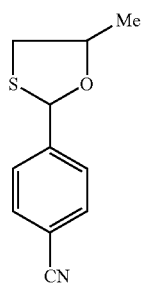

Compound 32

A mixture of 4-cyanobenzaldehyde (131 mg, 1.00 mmol), 1-mercapto-2-propanol (276 mg, 3.00 mmol), sodium sulfate (284 mg, 2.00 mmol) and freshly fused zinc chloride (273 mg, 2.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (284 mg). To the oil was added toluene (25 ml) and p-toluenesulfonic add monohydrate (6 mg, 31 μmol) and the mixture was refluxed for 70 min. After cooling the toluene was removed in vacuo and the residual oil subjected to flash chromatography (ether/hexane gradient) to give a diasteromeric mixture of 4-(5-methyl-1,3-oxathiolan-2-yl)benzonitrile (32) (76 mg, 37%) as a colourless oil. $^1$H nmr (d$_6$-dmso, 300 MHz) δ 1.32 & 1.43 (each d, J 6.0 Hz, total 3H); 2.83 & 3.29 (each m, total 2H); 4.21 & 4.60 (each m, total 1H); 6.17 & 6.30 (each s, total 1H); 7.58 (m, 2H); 7.82 (m, 2H).

Example 33

Preparation of 2-(4-Thien-2-ylphenyl)-1,3-oxathiolane (compound 33)

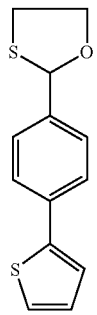

Compound 33

A mixture of 4-(2-thienyl)benzaldehyde (188 mg, 2.00 mmol), freshly distilled 2-mercaptoethanol (234 mg, 3.00 mmol), sodium sulfate (284 mg, 2.00 mmol) and freshly fused zinc chloride (273 mg, 2.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a yellow-green solid (323 mg). A solution of the solid and p-toluenesulfonic acid monohydrate (6 mg, 31 μmol) in toluene (25 ml) was refluxed for 70 min. After cooling, the toluene was removed in vacuo and the residual solid subjected to flash chromatography (ether/hexane gradient) to give 2-(4-thien-2-ylphenyl)-1,3-oxathiolane (33) (49 mg, 20%) as a white powder. $^1$H nmr (d$_6$-dmso, 300 MHz) δ 3.21 (m, 2H); 3.88 (m, 1H); 4.49 (m, 1H); 6.07, (s, 1H); 7.13 (dd, J 5.1, 4.8 Hz, 1H); 7.45 (d, J 8.4 Hz, 2H); 7.51 (dd, J 4.8, 1.1 Hz, 1H); 7.54 (dd, J 5.1, 1.1 Hz, 1H); 7.64 (d, J 8.4 Hz, 2H). ESI (+ve) MS m/z 249 (M+H, 70%).

Example 34

Preparation of 4-(5-Methyl-2-octyl-1,3-oxathiolan-2-yl)phenol (compound 34)

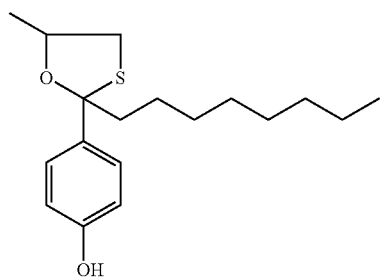

Compound 34

A mixture of 4'-hydroxynonanophenone (468 mg, 2.00 mmol), 1-mercapto-2-propanol (553 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (688 mg). A portion of the oil (410 mg) was subjected to flash chromatography (ether/hexane gradient) to give a mixture of the two diastereoisomers of 4-(5-methyl-2-octyl-1,3-oxathiolan-2-yl)phenol (34) (117 mg, 32%) as a colourless oil. $^1$H nmr (d$_6$-dmso, 300 MHz) δ 0.82 (t, J 6.6 Hz, 3H); 1.16 (br. s, 12H); 1.33 (m, 2H); 1.96 (m, 2H); 2.6 & 3.1 (each m, total 2H); 3.99 & 4.11 (each m, total 1H); 6.67 (m, 2H); 7.16 (m, 2H). ESI (+ve) MS m/z 309 (M+H, 25%).

Example 35

Preparation of 2-Fluoro-5-(5-methyl-1,3-oxathiolan-2-yl)benzenecarbonitrile (compound 35)

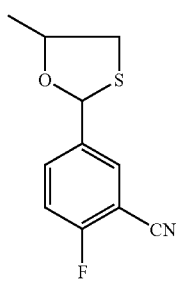

Compound 35

A mixture of 2-fluoro-5-formylbenzonitrile (298 mg, 2.00 mmol), 1-mercapto-2-propanol (553 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (10 ml) followed by saturated aqueous sodium chloride solution (10 ml). The solution was then dried (sodium sulfate), filtered and the solvent removed in vacuo to give a colourless oil (717 mg). To this oil was added toluene (25 ml) and p-toluenesulfonic acid monohydrate (8 mg, 41 µmol) and the mixture was refluxed for 1.5 h. After cooling the toluene was removed in vacuo and the residual oil subjected to flash chromatography (ether/hexane gradient) to give a mixture of the two diastereoisomers of 2-fluoro-5-(5-methyl-1,3-oxathiolan-2-yl)benzenecarbonitrile. (35) (295 mg, 66%) as a colourless oil. $^1$H nmr (d$_6$-dmso, 300 MHz) δ 1.31 & 1.42 (each d, J 6.0 Hz, total 3H); 2.85 & 3.30 (each m, total 2H); 4.18 & 4.61 (each m, total 1H); 6.11 & 6.25 (each s, total 1H); 7.51 (m, 1H); 7.83 (m, 1H); 7.93 (m, 1H).

Example 36

4-Methoxy-4'-(trifluoromethoxy)-1,1'-biphenyl (compound 36)

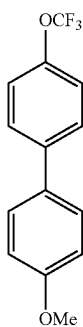

Compound 36

To a solution of 1-bromo-4-(trifluoromethoxy)benzene (0.90 g, 3.7 mmol) in tetrahydrofuran (20 ml) was added a solution of 2-(4-methoxyphenyl)-4,4,5,5-tetramethyl-1,3,2-dioxaborolane (0.36 g, 1.54 mmol) in tetrahydrofuran (10 ml), potassium carbonate (0.42 g, 3.0 mmol), [1,1-bis(diphenylphosphino)ferrocene]dichloropalladium (II) (40 mg, 0.077 mmol) and water (0.20 ml) and the mixture refluxed under nitrogen for 19 h. The reaction mixture was tipped into water (150 ml) and extracted with ether (2×50 ml), the ether extract then dried (MgSO$_4$) and evaporated to give a tan semi-solid (0.801 g). Purification by column chromatography (silica gel, 4:1 hexane/chloroform) afforded 4-methoxy-4'-(trifluoromethoxy)-1,1'-biphenyl (36) as a white solid (0.33 g, 80%). $^1$H nmr (CDCl$_3$, 300 MHz) 3.86, s, 4-OMe; 6.99, d (8.7 Hz), H3,5; 7.26, d (8.1 Hz), H3',5'; 7.49, d (8.7 Hz), H2,6 or H2',6'; 7.55, d (8.7 Hz), H2',6' or H2,6. APCI (+ve) MS m/z 268 (M$^+$, 80%).

Example 37

2,6-Dimethoxy-3-[4-(trifluoromethyl)phenyl]pyridine (compound 37)

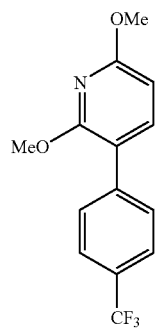

Compound 37

To a solution of 4-bromobenzotriflouride (0.85 g, 3.78 mmol) in tetrahydrofuran (20 ml) was added a solution of 2,6-dimethoxy-3-(4,4,5,5-tetramethyl-1,3,2-dioxaborolan-2-yl)pyridine (0.41 g, 1.55 mmol) in tetrahydrofuran (10 ml), potassium carbonate (0.42 g, 3.0 mmol), [1,1-bis(diphenylphosphino)ferrocene]dichloropalladium (II) (40 mg, 0.077 mmol) and water (0.2 ml) and the mixture refluxed under nitrogen for 19 h. The reaction mixture was tipped into water (150 ml) and extracted with ether (2×50 ml), the ether extract then dried (MgSO$_4$) and evaporated to give a light brown oil (0.537 g). Purification by column chromatography (silica gel, 2:1 hexane/chloroform) afforded 2,6-dimethoxy-3-[4-(trifluoromethyl)phenyl]pyridine (37) as a clear, colourless oil (0.359 g, 82%). $^1$H nmr (CDCl$_3$, 300 MHz) 4.00, s, 2×OMe; 6.44, d (8.1 Hz), H5; 7.60, d (8.1 Hz), H4; 7.66, m, H2',3',5',6'. ESI (+ve) MS m/z 284 (M+H, 100%).

Example 38 and 39

Diastereomers of 2-(4-bromophenyl)-2-butyl-4-propyl-1,3-oxathiane (compound 38) and (compound 39)

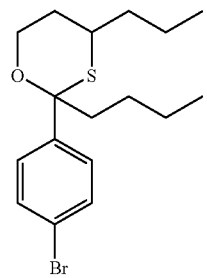

Compound 38/39

A mixture of 4-bromovalerophenone (482 mg, 2.00 mmol), 3-mercapto-1-hexanol (805 mg, 6.00 mmol), sodium sulfate (568 mg, 4.00 mmol) and freshly fused zinc chloride (545 mg, 4.00 mmol) in dry 1,4-dioxane (1 ml) was stirred under nitrogen at room temperature for 16 h. Water (10 ml) and ethyl acetate (20 ml) were added and the phases separated. The ethyl acetate layer was washed with more water (3×10 ml) followed by saturated aqueous sodium chloride solution (10 ml). The solution was then dried (sodium sulfate), filtered and the solvent removed in vacuo to give a colourless oil (1.112 g). To 467 mg of this oil were added toluene (25 ml) and p-toluenesulfonic acid monohydrate (7.5 mg, 39 μmol) and the mixture was refluxed for 5 h. After cooling, the toluene was removed in vacuo and the residual oil subjected to flash chromatography (ether/hexane gradient) to give a colourless oil (254 mg), consisting of the starting ketone and the two diastereoisomers of 2-(4-bromophenyl)-2-butyl-4-propyl-1,3-oxathiane (38/39). Further flash chromatography (dichloromethane/hexane gradient) gave in order of elution, the first diastereomer (38) as a colourless oil (36 mg), followed by the second diastereomer (39), also as a colourless oil (43 mg). The $^1$H nmr data for the separated diastereomers is given below.

(38) $^1$H nmr ($d_6$-dmso, 300 MHz) δ 0.76 (t, J 7.2 Hz, 3H); 0.85 (t, J 6.9 Hz, 3H); 0.9-1.5 (complex, 9H); 1.83 (dd, J 13.5, 2.7 Hz, 1H); 2.00 (ddd, J 15.0, 11.4, 4.2 Hz, 1H); 2.76 (ddd, J 15.0, 11.7, 4.2 Hz, 1H); 3.35 (m, 1H); 3.89 (dt, J 11.7, 1.8 Hz, 1H); 3.98 (m, 1H); 7.38 (d, J 8.7 Hz, 2H); 7.52 (d, J 8.7 Hz, 2H).

(39) $^1$H nmr ($d_6$-dmso, 300 MHz) δ 0.74 (t, J 7.2 Hz, 3H); 0.84 (t, J 6.9 Hz, 3H); 0.9-1.3 (complex, 4H); 1.3-1.9 (complex, 8H); 2.61 (m, 1H); 3.40 (apparent dt, J 12.3, 2.4 Hz); 3.83 (ddd, J 12.3, 3.6, 1.5 Hz); 7.49 (d, J 8.7 Hz, 2H); 7.60 (d, J 8.7 Hz, 2H).

Example 40

4-(1,3-Dioxolan-2-yl)benzenecarbonitrile (compound 40)

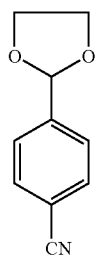

Compound 40

4-Cyanobenzaldehyde (500 mg, 3.81 mmol), ethylene glycol (828 mg, 13.34 mmol) and a catalytic amount of p-toluenesulfonic acid monohydrate were refluxed in toluene (25 mL) overnight in a Dean-Stark apparatus. The reaction mixture was then concentrated and the residue dissolved in chloroform (50 ml) and washed with saturated sodium bicarbonate solution (2×25 mL) and brine (1×25 mL). The organic phase was dried ($Na_2SO_4$) and evaporated to give 4-(1,3-dioxolan-2-yl)benzenecarbonitrile (40) as an oil which solidified to a white solid (633 mg, 95%). $^1$H NMR (CDCl$_3$, 300 MHz): δ 4.04, t (1.8 Hz), OCH$_2$; 4.07, t (2.0 Hz), OCH$_2$; 5.82, s, H2; 7.64, d (1.4 Hz), 2×ArH; 7.73, d (1.3 Hz), 2×ArH. ESI (+ve) MS: m/z 176 (M+H, 12%).

Example 41

2-(3,5-Dimethoxyphenyl)-2-hexyl-1,3-dioxolane (compound 41)

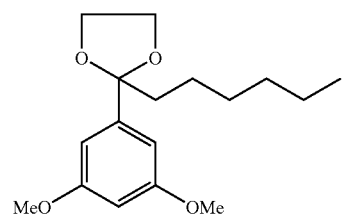

Compound 41

1-(3,5-Dimethoxyphenyl)heptan-1-one (200 mg, 0.80 mmol), ethylene glycol (173 mg, 2.80 mmol) and a catalytic amount of p-toluenesulfonic acid monohydrate were refluxed in toluene (25 mL) overnight in a Dean-Stark apparatus. The reaction mixture was then concentrated and the residue dissolved in chloroform (50 mL) and washed with saturated sodium bicarbonate solution (2×25 mL) then brine (1×25 mL). The organic phase was dried ($Na_2SO_4$) and evaporated to give 2-(3,5-dimethoxyphenyl)-2-hexyl-1,3-dioxolane (41) as a light yellow oil (213 mg, 90%). $^1$H NMR (CDCl$_3$, 300 MHz): δ 0.94, t (6.5 Hz), CH$_3$; 1.31, m, methylene envelope; 1.89, m, CH$_2$; 3.79-3.83, m, 2×OMe, OCH$_2$; 4.04, m, OCH$_2$; 6.46, m, H4'; 6.63, m, H2',6'. ESI (+ve) MS: m/z 295 (M+H, 62%).

Example 42

2-(4-Chlorophenyl)-2-ethyl-4-methyl-1,3-dioxolane (compound 42)

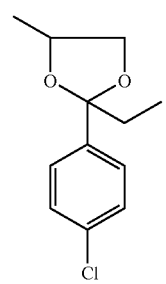

Compound 42 p-Chloropropriophenone (250 mg, 1.48 mmol), propylene glycol (395 mg, 5.19 mmol) and a catalytic amount of p-toluenesulfonic acid monohydrate were refluxed in toluene (25 mL) overnight in a Dean-Stark apparatus. The reaction mixture was then concentrated and the residue dissolved in chloroform (50 mL) and washed with saturated sodium bicarbonate solution (2×25 mL) then brine (1×25 mL). The organic phase was dried ($Na_2SO_4$) and evaporated to give a 2:1 diasteromeric mixture of 2-(4-chlorophenyl)-2-ethyl-4-methyl-1,3-dioxolane (42) as an oil (329 mg, 98%). $^1$H NMR (CDCl$_3$, 300 MHz): δ 0.88, t (7.4 Hz), CH$_2$CH$_3$ (minor); 0.92, t (7.4 Hz), CH$_2$CH$_3$ (major); 1.19, d (6.1 Hz), C4-Me (minor); 1.32, d (6.0 Hz), C4-Me (major); 1.87, m, CH$_2$CH$_3$ (both); 3.27, t (8.0 Hz), H5 (minor); 3.53, t (7.2 Hz), H5 (major); 3.92, t (7.3 Hz), H5 (major); 4.05, app q (6.3 Hz), H4 (major); 4.20, dd (5.8, 8.1 Hz), H5 (minor); 4.33, m, H4 (minor), 7.3-7.5, m, 4×ArH (both). ESI (+ve) MS: m/z 244 (M+NH$_4$, 7%).

Example 43

5-(5,5-Diethyl-1,3-dioxan-2-yl)-2-fluorobenzenecarbonitrile (compound 43)

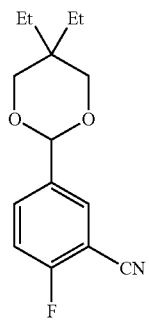

Compound 43

2-Fluoro-5-formylbenzonitrile (250 mg, 1.68 mmol), 2,2-diethyl-1,3-propanediol (776 mg, 5.87 mmol) and a catalytic amount of p-toluenesulfonic acid monohydrate were refluxed in toluene (25 mL) overnight in a Dean-Stark apparatus. The reaction mixture was then concentrated and the residue dissolved in chloroform (50 mL) and washed with saturated sodium bicarbonate solution (2×25 mL) then brine (1×25 mL). The organic phase was dried (Na$_2$SO$_4$) and evaporated to give an oil. The oil was then chromatographed on silica gel (4:1 hexane/ethyl acetate) to give 5-(5,5-diethyl-1,3-dioxan-2-yl)-2-fluorobenzenecarbonitrile (43) as a light yellow oil (401 mg, 91%). $^1$H NMR (MeOD, 300 MHz): δ 0.90, t (7.7 Hz), CH$_2$CH$_3$; 0.97, t (7.5 Hz), CH$_2$CH$_3$; 1.25, q (7.6 Hz), CH$_2$CH$_3$; 1.86, q (7.6 Hz), CH$_2$CH$_3$; 3.72, d (11.5 Hz), CH$_2$O; 4.02, d (11.4 Hz), CH$_2$O; 5.52, s, H2; 7.42, t (9.3 Hz), H3; 7.86, m, H4,6. ESI (+ve) MS: m/z 264 (M+H, 11%).

Example 44

2-(4-Chlorophenyl)-4,5-dihydro-1,3-oxazole (compound 44)

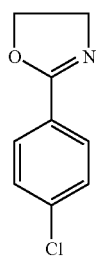

Compound 44 p-Chlorobenzoic add (0.5 g, 3.19 mmol) was suspended in thionyl chloride (25 mL) and refluxed overnight. The excess thionyl chloride was removed in vacuo to furnish the acid chloride as a light brown solid. The solid was then dissolved in dichloromethane (25 mL), cooled on an ice bath and etha-nolamine (0.40 mL, 6.4 mmol) added to the mixture, followed by the addition of triethylamine (2.3 mL, 16 mmol) and the mixture was then stirred overnight at room temperature. The mixture was then diluted with chloroform (50 mL) and washed with 1M hydrochloric acid (2×25 mL) and brine (1×25 mL) before concentrating the solvent to give the crude amide as an oil, which solidified to an off-white solid. Without further purification the crude amide was then dissolved in ethyl acetate (10 mL) to which was added dropwise, a solution of thionyl chloride (0.7 mL, 6.4 mmol) in ethyl acetate (3 mL) and the mixture stirred overnight at room temperature before concentrating to furnish the solid chloro-amide. After dissolving in dichloromethane (10 mL) and addition of DBU (1 mL, 6.4 mmol) the mixture was refluxed overnight. Concentration of the solvent and flash chromatography of the resulting gum furnished 2-(4-chlorophenyl)-4,5-dihydro-1,3-oxazole (44) as a white crystalline solid (327 mg, 56% overall yield).

$^1$H NMR (d$_4$-MeOH, 300 MHz): δ 4.09, t (9.6 Hz), H4; 4.57, t (9.5 Hz), H5; 7.54, d (8.6 Hz), 2×ArH; 7.95, d (8.6 Hz), 2×ArH. ESI (+ve) MS: m/z 182/184 (M+H, 100%/32%).

Example 45

2-(4-Methylphenyl)-4,5-dihydro-1,3-oxazole (compound 45)

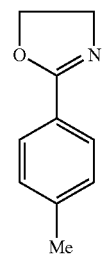

Compound 45 p-Toluic acid (0.5 g, 3.67 mmol) was suspended in thionyl chloride (25 mL) and refluxed overnight. The excess thionyl chloride was removed in vacuo to furnish the acid chloride as a light brown solid. The solid was then dissolved in dichloromethane (25 mL), cooled on an ice bath and ethanolamine (0.45 mL, 7.3 mmol) added to the mixture, followed by the addition of triethylamine (2.6 mL, 18.4 mmol) and the mixture was then stirred overnight at room temperature. The mixture was then diluted with chloroform (50 mL) and washed with 1M hydrochloric acid (2×25 mL) and brine (1×25 mL) before concentrating the solvent to give the crude amide as an oil, which solidified to an off-white solid. Without further purification the crude amide was then dissolved in ethyl acetate (10 mL) to which was added dropwise, a solution of thionyl chloride (0.8 mL, 7.3 mmol) in ethyl acetate (3 mL) and the mixture stirred overnight at room temperature before concentrating to give the chloro-amide as a brown solid. After dissolving in dichloromethane (10 mL) and addition of DBU (1.1 mL, 7.3 mmol) the mixture was refluxed overnight. Concentration of the solvent and flash chromatography of the resulting gum furnished 2-(4-methylphenyl)-4,5-dihydro-1,3-oxazole (45) as a white crystalline solid (236 mg, 40% overall yield).

$^1$H NMR (d$_4$-MeOH, 300 MHz): δ 2.45, s, Me; 4.07, t (9.6 Hz), H4; 4.54, t (9.5 Hz), H5; 7.33, d (7.9 Hz), 2×ArH; 7.86, d (7.9 Hz), 2×ArH. ESI (+ve) MS: m/z 162 (M+H, 100%).

BIOLOGICAL EXAMPLES

Biological Example 1

MIF-Induced Human Fibroblast Proliferation

Methods

The activity of a compound of formula (I) was studied in a bioassay utilising MIF-induced proliferation of human dermal fibroblasts. The proliferation of human fibroblasts has been demonstrated to be a phenomenon inducible by MIF [16]. S112 human dermal fibroblasts were propagated in RPMI/10% foetal calf serum (FCS). Prior to experimentation, cells were seeded at $10^5$ cells/ml in RPMI/0.1% BSA for 18 hours. Cells were treated with recombinant human macrophage migration inhibitory factor (MIF) 50 ng/ml and/or a compound of the invention at a concentration of 1 nM. The compound was combined with MIF at time point −30 minutes, prior to adding to cell culture at time point zero. At time point zero, culture medium was replaced with RPMI/10% FCS and treatments administered. At time point 30 hours, cells were pulsed with 1 µCi $^3$H-thymidine. At time point 48 hours, cells were harvested using a semi-automated cell harvester. The radioactivity incorporated into DNA was determined by liquid scintillation counting, with results expressed as $^3$H-thymidine incorporation.

Significant inhibition of MIF-induced proliferation was determined by the demonstration of a significant P value ($P<0.05$) using the Mann-Whitney U-test.

Results 2-(2-hydroxyethoxy)-2-(4-hydroxy-3-methylphenyl)-1,3-dioxolane (Compound 1) (cpd 1), when used in the method above, significantly inhibited the induction of S112 human fibroblast proliferation ($P<0.05$), as shown in Table 1 and FIG. 1. Treatment of cells with MIF (+MIF) induced proliferation, but this was prevented by pre-incubating MIF with Compound 1 (1 nM) (+MIF+cpd 1) (*$P<0.05$). These data are consistent with these compounds exerting inhibitory effects on the biological activity of MIF.

TABLE 1

|  | Untreated cells | MIF-treated cells | MIF-treated cells + cpd1 at 1 nM |
|---|---|---|---|
| Mean (cpm) | 3245 | 4415 | 2994* |
| Standard error | 393.1 | 403.5 | 410.7 |
| Number of experiments | 9 | 9 | 9 |

*$P < 0.05$

Biological Example 2

MIF-Dependent IL-1 Induced Fibroblast Cyclooxygenase-2 Expression

Methods

The activity of the compounds of formula (I) were further studied in a bioassay utilising MIF-dependent activation of human dermal fibroblasts. Sampey et al have shown that induction of the expression of cyclooxygenase-2 (COX-2) by the cytokine interleukin 1 (IL-1) is dependent upon the presence of MIF, i.e. can be prevented using specific anti-MIF monoclonal antibody [17]. IL-1-induced COX-2 expression is therefore a MIF-dependent event.

S112 human dermal fibroblasts were propagated in RPMI/10% foetal calf serum (FCS). Prior to experimentation, cells were seeded at $2\times10^5$ cells/ml in RPMI/0.1% BSA for 18 hours. Cells were treated with compound at 1-100 µM and 30 minutes later with recombinant human IL-1 (0.1 ng/ml). After 6 hours, cells were collected and intracellular COX-2 protein determined by permeabilisation flow cytometry, as described by Sampey et al [18]. Cells permeabilised with 0.2% saponin were sequentially labelled with a mouse anti-human COX-2 monoclonal antibody and with sheep-anti-mouse F(ab)2 fragment labelled with fluoroscein isothiocyanate. Cellular fluorescence was determined using a flow cytometer. At least 5000 events were counted for each reading, each of which was performed in duplicate, and the results expressed in mean fluorescence intensity (MFI) after subtraction of negative control-labelled cell fluorescence.

Figure 2:
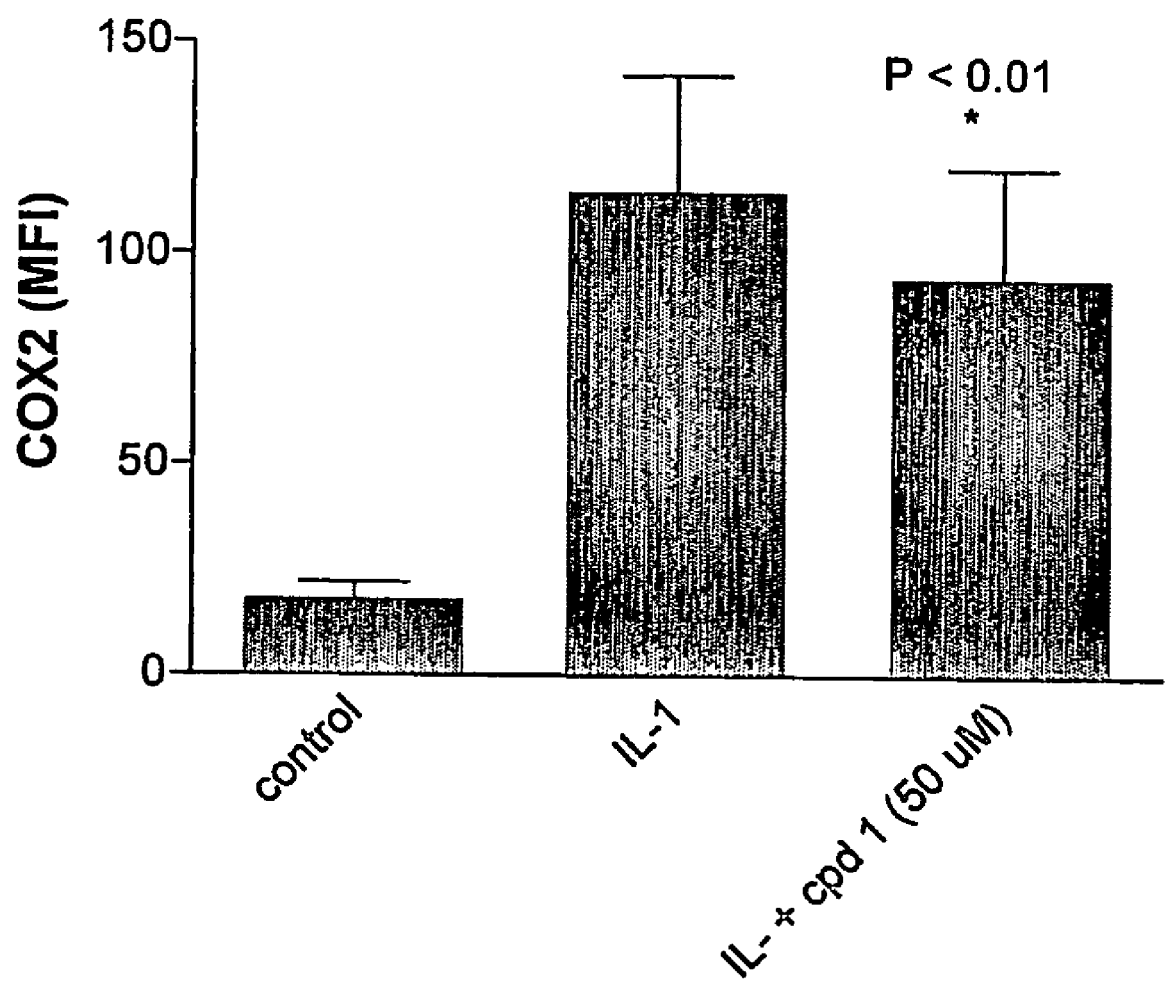
FIG. 2: graphically depicts inhibition of IL-1 induced COX-2 expression by 2-(2-hydroxyethoxy)-2-(4-hydroxy-3-methylphenyl)-1,3-dioxolane (Compound 1).

In Table 2 and FIG. 2, the effect of each concentration of 2-(2-hydroxyethoxy)-2-(4-hydroxy-3-methylphenyl)-1,3-dioxolane (Compound 1) was determined by subtracting the IL-1+ compound-treated cell MFI from the IL-1-treated cell MFI, and expressed as % inhibition. Significant inhibition of IL-induced COX-2 expression was determined by the demonstration of a significant P value ($P<0.05$) using Student's test.

Results

As shown in FIG. 2, cells treated with Compound 1 exhibited a significant reduction in COX-2 expression as measured by flow cytometry ($P<0.01$). Statistically significant inhibition of the induction of COX-2 expression by IL-1 in human S112 fibroblast cells was demonstrated when cells were treated with Compound 1 (cpd 1) 50 µM (*$P<0.01$).

Figure 3:
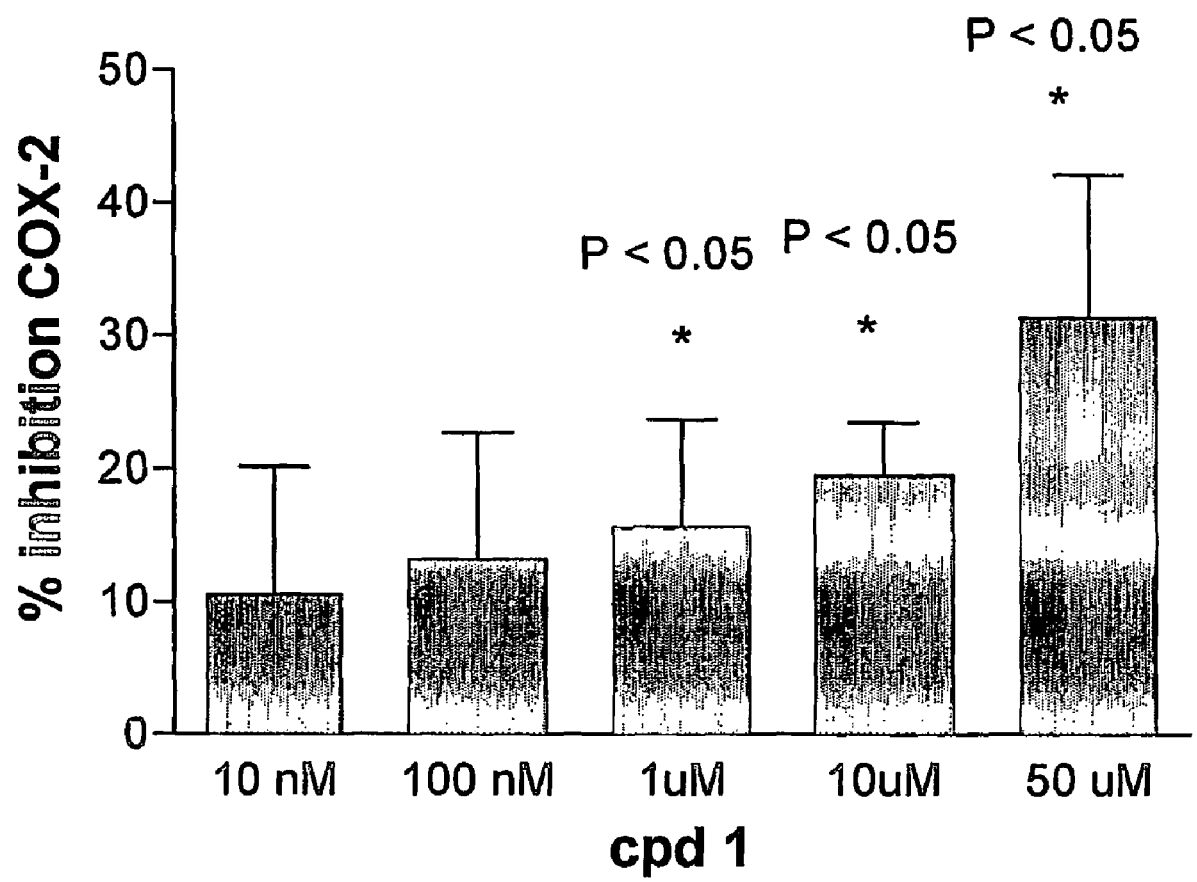
FIG. 3: graphically depicts inhibition of IL-1 induced COX-2 expression by 2-(2-hydroxyethoxy)-2-(4-hydroxy-3-methylphenyl)-1,3-dioxolane (Compound 1).

As shown in Table 2 and FIG. 3, cells treated with 2-(2-hydroxyethoxy)-2-(4-hydroxy-3-methylphenyl)-1,3-dioxolane (Compound 1) exhibited a dose-dependent reduction in COX-2 expression as measured by flow cytometry. These data are consistent with these compounds exerting inhibitory effects on the biological activity of MIF.

TABLE 2

| Concentration of Compound 1 (µM) | Mean % inhibition COX2 expression | Standard error | Number of experiments |
|---|---|---|---|
| 0.01 | 10.5 | 9.6 | 4 |
| 0.1 | 13.2 | 9.5 | 4 |
| 1 | 15.6* | 8.1 | 4 |
| 10 | 19.5* | 3.9 | 6 |
| 50 | 31.4* | 10.8 | 8 |

*$P < 0.05$

Figure 4:
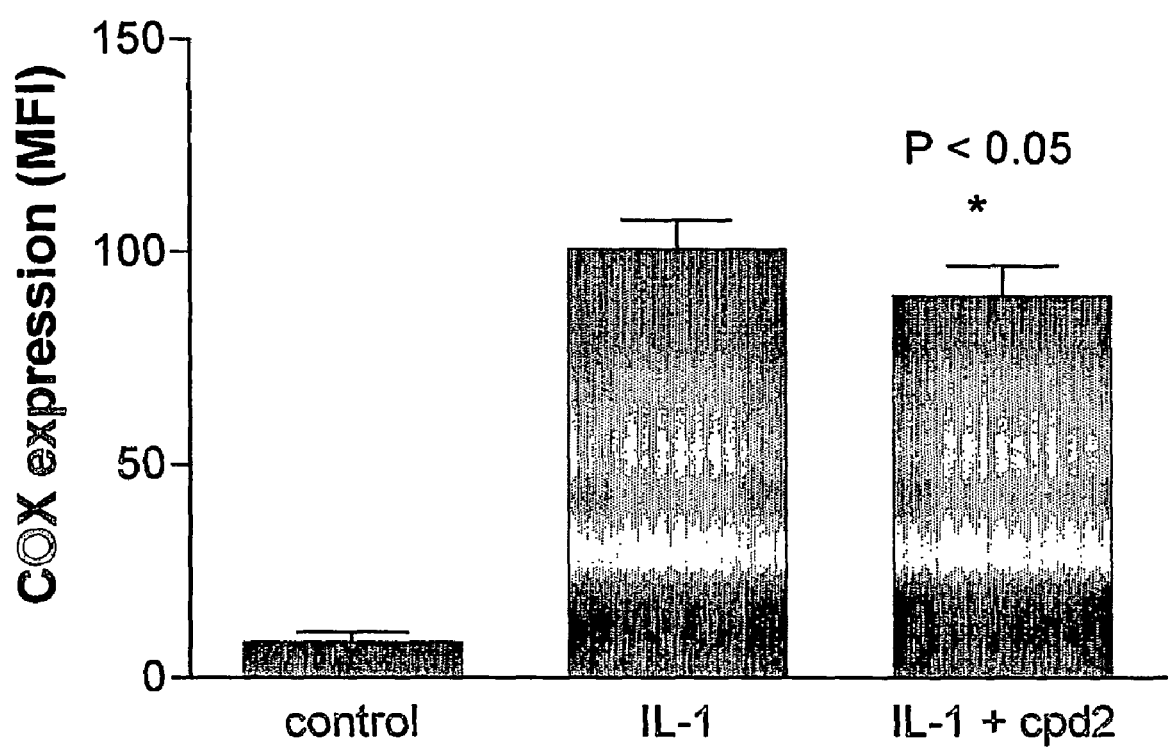
FIG. 4: graphically depicts inhibition of IL-1 induced COX-2 expression by 2-(2-hydroxyethoxy)-2-(4'-hydroxyphenyl)-1,3-dioxolane (Compound 2).

In FIG. 4, the effect of 2-(2-hydroxyethoxy)-2-(4-hydroxyphenyl)-1,3-dioxolane (Compound 2) is expressed as mean fluorescence intensity (MFI), after deducting the MFI of control-labelled cells. Significant inhibition of IL-induced COX-2 expression was determined by the demonstration of a significant P value ($P<0.05$) using Student's test. Significant inhibition of IL-induced COX-2 expression in human S112 fibroblast cells was demonstrated in cells treated with Compound 2 (IL-1+cpd2) compared to cells treated with IL-1 (*$P<0.05$).

Biological Example 3

MIF-Dependent Antigen-Specific T Cell Activation

Methods

The activity of compounds of formula (I) was further studied in a bioassay utilising MIF-dependent activation of murine T cell activation. The activation of T lymphocytes in response to exposure to a recall antigen is known to be dependent on the presence of MIF, i.e. can be prevented using specific anti-MIF monoclonal antibody[7]. Antigen-induced T cell activation is therefore a MIF-dependent phenomenon.

Splenocytes were obtained by Hank's buffered saline flushing of spleens obtained from C57Bl/6 mice previously immunized with methylated bovine serum albumin (mBSA, Sigma Chemical Co., Castle Hill, Australia). Mice were immunized on day 0 with 200 μg mBSA emulsified in 0.2 ml of Freund's complete adjuvant (FCA) injected subcutaneously into the flank skin. On day 7, the mice received 100 μg mBSA/0.1 ml FCA by intradermal injection at the base of the tail. Spleens were removed on day 14 after first immunisation and a single cell suspension was prepared in DMEM containing 5% FCS and 0.05% 2-mercaptoethanol. $1 \times 10^5$ cells/200l were cultured in triplicate in the presence of mBSA (10 μg/ml) with or without the addition of 2-(2-hydroxyethoxy)-2-(4-hydroxyphenyl)-1,3-dioxolane (Compound 2) at a concentration of 100 nM-10 μM, 30 minutes before the addition of mBSA. The T cell proliferation response was determined by measuring the amount of [$^3$H] thymidine incorporation during the final 18 hr. The cells were harvested and radioactivity incorporation into the DNA was measured with a Wallac 1409 liquid scintillation counter (Pharmacia, Turku, Finland). Significant inhibition of T cell activation was determined by the demonstration of a significant P value ($P<0.05$) using Student's test.

Results.

Figure 5:
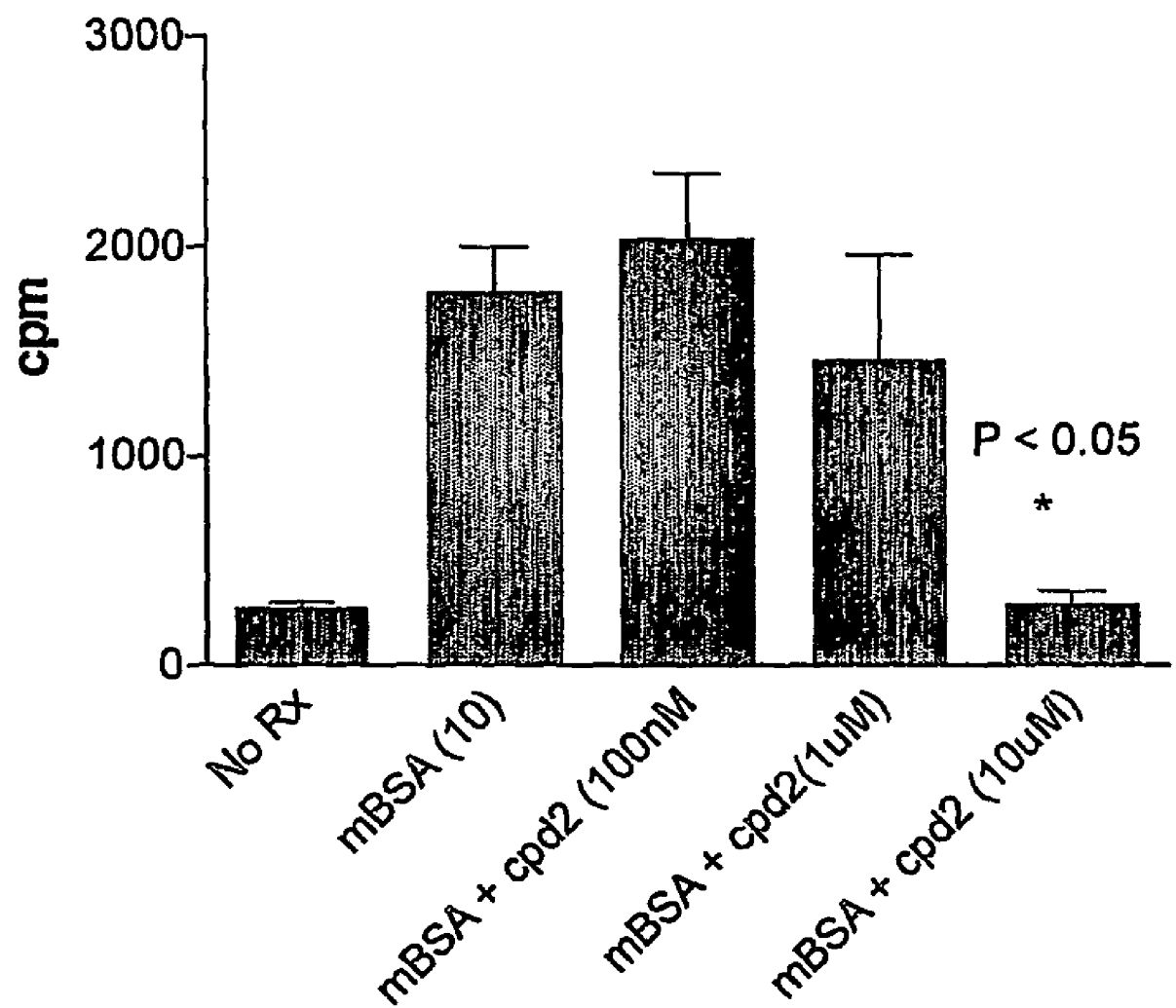
FIG. 5: graphically depicts inhibition of antigen-specific T-cell activation by 2-(2-hydroxyethoxy)-2-(4-hydroxyphenyl)-1,3-dioxolane (Compound 2).

Treatment of spleen cells with 2-(2-hydroxyethoxy)-2-(4-hydroxyphenyl)-1,3-dioxolane (Compound 2) (cpd2) resulted in a significant dose-dependent reduction in antigen-specific T cell activation, compared to cells exposed to mBSA without Compound 2 (*$P<0.05$) (FIG. 5). These data are consistent with these compounds exerting inhibitory effects on the biological activity of MIF.

Biological Example 4

Combination of MIF-Antagonist with Glucocorticoid: Effects on MIF-Dependent IL-1 Induced Fibroblast Cyclooxygenase-2 Expression A particular aspect of the biological function of MIF relates to its ability to antagonise the anti-inflammatory effects of glucocorticoids such as dexamethasone, as recently reviewed by Morand et al.[4]. This property of MIF suggests that MIF antagonists might exert "steroid-sparing" effects, that is, their use in combination with glucocorticoids might permit the achievement of a greater therapeutic effect with a given dose of glucocorticoids. Thus, in the presence of MIF antagonists, low doses of glucocorticoids could exert a therapeutic effect otherwise requiring a higher dose of glucocorticoids. As the adverse effects of glucocorticoids are in general dose-dependent, the ability to reduce the requirement for glucocorticoids is clinically desirable.

The potential for a MIF antagonist to be "steroid-sparing", therefore, could be demonstrated by the observation of enhanced effectiveness of a given dose of glucocorticoids in the presence of a MIF antagonist.

Methods

Figure 6:
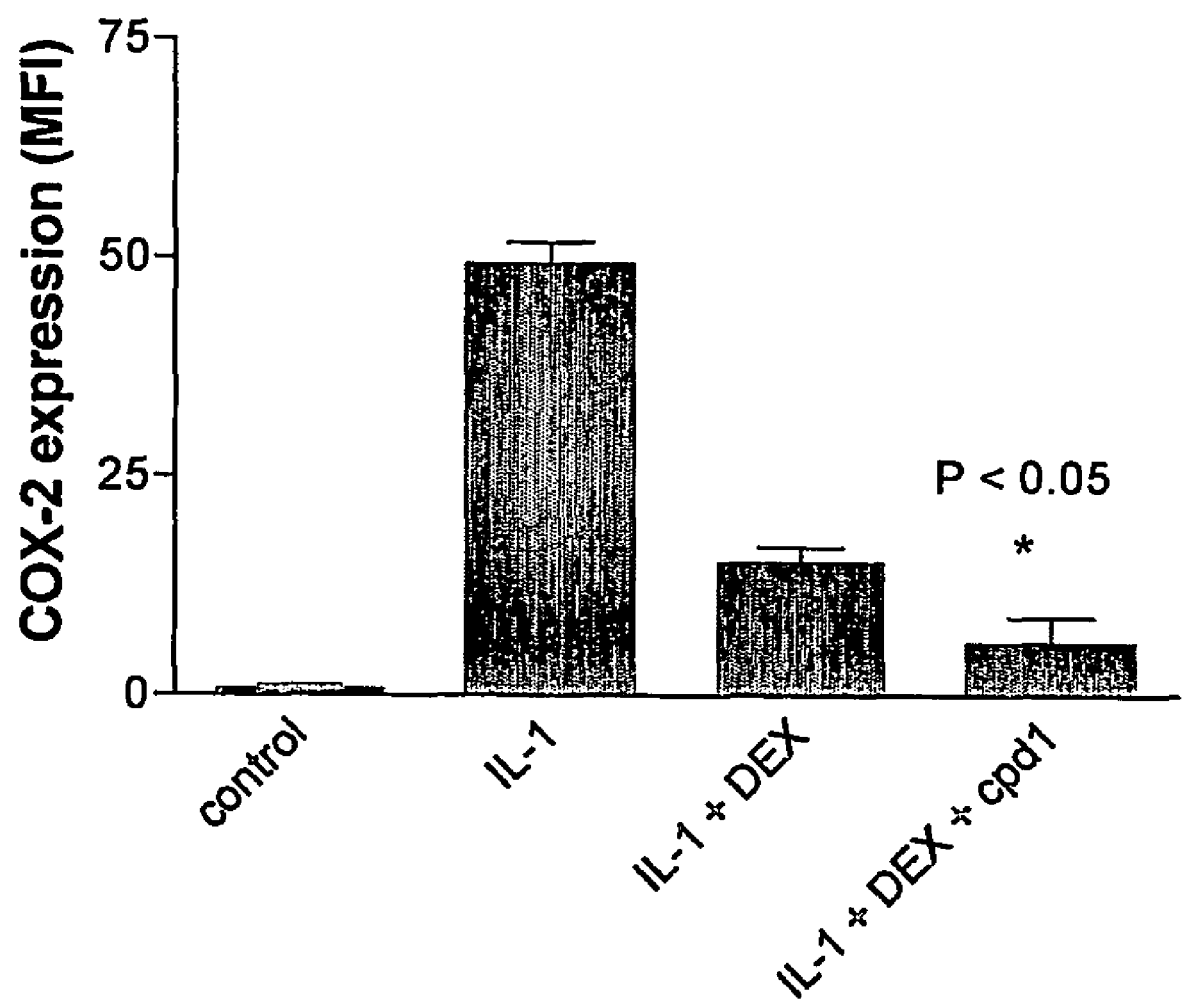
FIG. 6: graphically depicts the enhanced effect of the glucocorticoid dexamethasone in the presence of 2-(2-hydroxyethoxy)-2-(4-hydroxy-3-methylphenyl)-1,3-dioxolane (Compound 1).

The above in vitro assay (Biological Example 2) for analysing the effect of MIF antagonists on IL-1 induced COX-2 expression was performed using 2-(2-hydroxyethoxy)-2-(4'-hydroxy-3'-methylphenyl)-1,3-dioxolane (Compound 1) (50 μM), dexamethasone (1 nM) or a combination of dexamethasone (1 nM) and Compound 1 (50 μM). COX-2 expression was expressed as the mean fluorescence intensity (MFI) as measured by flow cytometry, after deduction of the MFI for control-labelled samples, as described by Sampey et al.[18]. The results are shown in Table 3 and FIG. 6.

Results

Significant enhancement of the inhibitory effects of the glucocorticoid dexamethasone was determined by the demonstration of a significant P value ($P<0.05$) using Student's test, compared to the effect of dexamethasone alone. Compared to the inhibition of IL-1-induced COX-2 expression achieved with 1 nM dexamethasone alone (IL-1+DEX), a significantly greater inhibition of IL-1-induced COX-2 expression was observed when cells were treated with 1 nM dexamethasone together with Compound 1 50 μM (IL-1+DEX+cpd1) ($P<0.05$). These data are consistent with these compounds exerting inhibitory effects on the biological activity of MIF.

TABLE 3

|  | Control | IL-1 | IL-1 + DEX | IL-1 + DEX + cpd1 |
| --- | --- | --- | --- | --- |
| Mean COX-2 expression (MFI) | 0.7400 | 49.37 | 15.13 | 6.013* |
| Standard error | 0.4413 | 2.412 | 1.770 | 2.906 |
| N | 4 | 4 | 4 | 4 |

*P < 0.05

Biological Example 5

Lack of Cytotoxicity

A valuable characteristic of a therapeutic material is a lack of toxicity. The compounds of formula (I) may have low toxicity towards cells. To examine this in vitro, the ability of 2-(2-hydroxyethoxy)-2-(4-hydroxy-3-methylphenyl)-1,3-dioxolane (Compound 1) to induce apoptosis ("programmed cell death") was investigated. A lack of cytotoxicity would be evidenced by the finding of equivalent proportions of apoptotic and viable cells in control- and compound-treated cells.

Methods

To examine the cytotoxicity of compounds of formula (I), S112 human dermal fibroblasts were exposed to a therapeutic concentration (50 μM) of 2-(2-hydroxyethoxy)-2-(4-hydroxy-3-methylphenyl)-1,3-dioxolane (Compound 1) or vehicle (control) and analysed for apoptosis by flow cytometric analysis of annexin V and propidium iodide staining, as described by Leech et al.[19]. Toxicity was assessed by analysis of apoptosis using flow cytometric detection of cell surface Annexin V binding and propidium iodide staining. At least 5000 events were analysed for each experiment. Cells positive for both Annexin V and propidium iodide were designated as apoptotic and cells negative for both Annexin V and propidium iodide were designated as viable. Results are expressed as the percentage (%) of cells with each of these labels.

Results.

Figure 7:
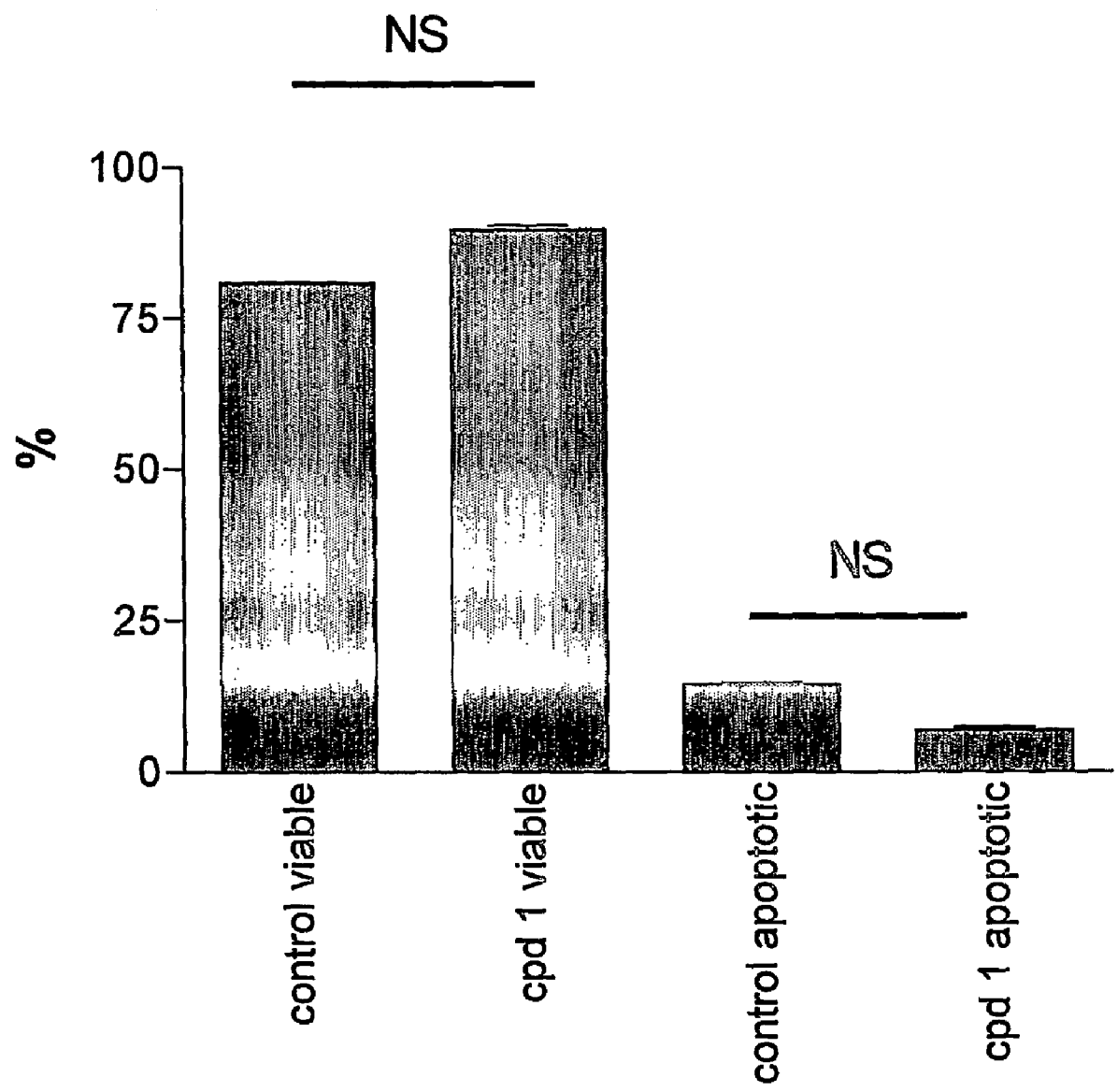
FIG. 7: graphically depicts the absence of cytotoxic effects of 2-(2-hydroxyethoxy)-2-(4-hydroxy-3-methylphenyl)-1,3-dioxolane (Compound 1).

The results of cytotoxicity analysis are shown in FIG. 7. No significant increase (ns) in apoptotic cell numbers, and no significant decrease (ns) in viable cell numbers, was observed in cells treated with 2-(2-hydroxyethoxy)-2-(4-hydroxy-3-methylphenyl)-1,3-dioxolane (Compound 1) compared to control-treated cells.

Biological Example 6

MIF-Dependent Nitrite Production in Peritoneal Macrophages

MIF is able to induce or facilitate the expression and release of a wide variety of pro-inflammatory and/or destructive molecules, including the release of macrophage nitric oxide (NO) [20]. A compound with the ability to inhibit the cytokine or biological function of MIF might be expected to inhibit the activation of NO production by macrophages.

Methods

C57BL6/J male mice were injected intraperitoneally with 2 ml of thioglycolate. Three days later peritoneal macrophages were collected by lavaging the peritoneum with 3 ml of cold Hank's buffered saline solution. Cells from several mice were pooled, washed and re-suspended in DMEM supplemented with 5% FCS. Cells were plated in 96 well plastic tissue culture plates at $1 \times 10^5$ cells/well. Cells were treated in triplicate wells with compound or vehicle for 1 hour in a 5% $CO_2$ incubator at 37° C. Cells were then treated with LPS (10 ng/ml) and recombinant human interferon-γ (10 units/ml) and incubated for 24 hours. After 24 hours, 50 µl of supernatant from each well was carefully removed and transferred to ELISA plates. The production of NO was measured by analysing the concentration of nitrite in culture supernatants, as measured by the Greiss assay [21]. The results were calculated as the percentage inhibition of nitrite concentration in compound-treated cell culture supernatants, compared to that of vehicle-treated cells.

Results

Figure 8:
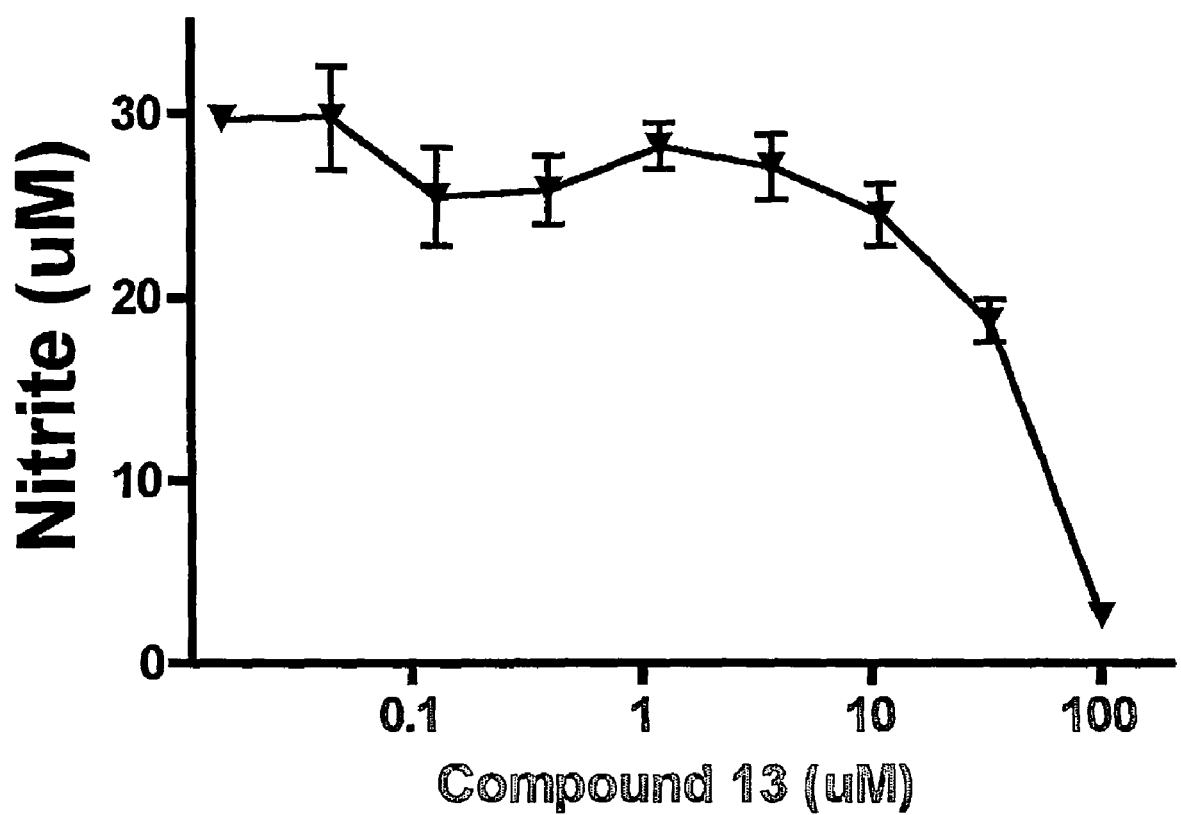
FIG. 8: graphically depicts the inhibition of macrophage nitrite release by 1-(3-Methylbutyl)-4-(4-methylphenyl)-1H-pyrazole (Compound 13).

Treatment of cells with 1-(3-Methylbutyl)-4-(4-methylphenyl)-1H-pyrazole (Compound 13) 0.5-100 µM resulted in a dose-responsive inhibition of LPS-IFN—induced nitrite production (FIG. 8).

Table 4 displays the results for other compounds tested in this assay. Marked reductions in nitrite concentration were observed in the supernatants of cells treated with the compounds. These data are consistent with these compounds exerting inhibitory effects on the biological activity of MIF.

Significant inhibition of nitrite production was determined by the demonstration of a significant P value (P<0.05) using the Mann-Whitney U-test.

TABLE 4

| Compound | % Inhibition of nitrite (± SD) | Compound concentration (µM) |
|---|---|---|
| 4  | 22 ± 1* | 100 |
| 5  | 22 ± 2  | 100 |
| 7  | 15 ± 1  | 100 |
| 9  | 16 ± 1  | 1   |
| 11 | 19 ± 1* | 33  |
| 12 | 78 ± 9* | 100 |
| 13 | 91 ± 8* | 100 |
| 14 | 27 ± 3* | 100 |
| 15 | 12 ± 1* | 100 |
| 17 | 69 ± 2* | 100 |
| 18 | 40 ± 1* | 100 |
| 24 | 21 ± 2* | 33  |
| 25 | 7 ± 1   | 33  |
| 27 | 24 ± 1* | 100 |
| 29 | 9 ± 1*  | 100 |
| 30 | 31 ± 2* | 100 |
| 31 | 35 ± 3* | 100 |

TABLE 4-continued

| Compound | % Inhibition of nitrite (± SD) | Compound concentration (µM) |
|---|---|---|
| 32 | 14 ± 4  | 100 |
| 33 | 47 ± 4* | 100 |
| 34 | 24 ± 1* | 100 |
| 35 | 18 ± 2* | 100 |
| 36 | 57 ± 1* | 100 |
| 37 | 24 ± 1* | 100 |
| 38 | 35*     | 100 |
| 40 | 7 ± 2   | 100 |
| 41 | 26 ± 1* | 100 |
| 43 | 34 ± 1* | 100 |
| 45 | 7 ± 1   | 100 |

*P < 0.05

Biological Example 7

MIF-Induced Proliferation in Mouse Fibroblasts

Methods

The activity of compounds was studied in a bioassay utilising MIF-induced proliferation of mouse NIH 3T3 fibroblasts. The proliferation of NIH3T3 fibroblasts has been demonstrated to be a phenomenon inducible by MIF [22], and MIF-induced proliferation has been linked to the pathology of diseases such as rheumatoid arthritis [16]. NIH 3T3 cells were propagated in DMEM/10% foetal calf serum (FCS). Prior to experimentation, cells were seeded at $10^4$ cells/well in 96-well plates in DMEM/10% FCS for 18 hours. The media was then replaced with DMEM/0.1% FCS and the cells incubated for a further 18 hr. At time point −1 hr, culture medium was replaced with DMEM/0.1% FCS and cells were treated with a compound of the invention at a final concentration of 10 µM or vehicle. At time point zero, cells were treated with MIF at a final concentration of 50 ng/ml. At time point 6 hr the cells were pulsed with 1 Ci/well of $^3$H-thymidine. At time point 24 hours, cells were harvested using a semi-automated cell harvester. The radioactivity incorporated into DNA was determined by liquid scintillation counting, with results expressed as $^3$H-thymidine incorporation (cpm). Statistical significance was analysed using the Mann-Whitney test.

Results

Figure 9:
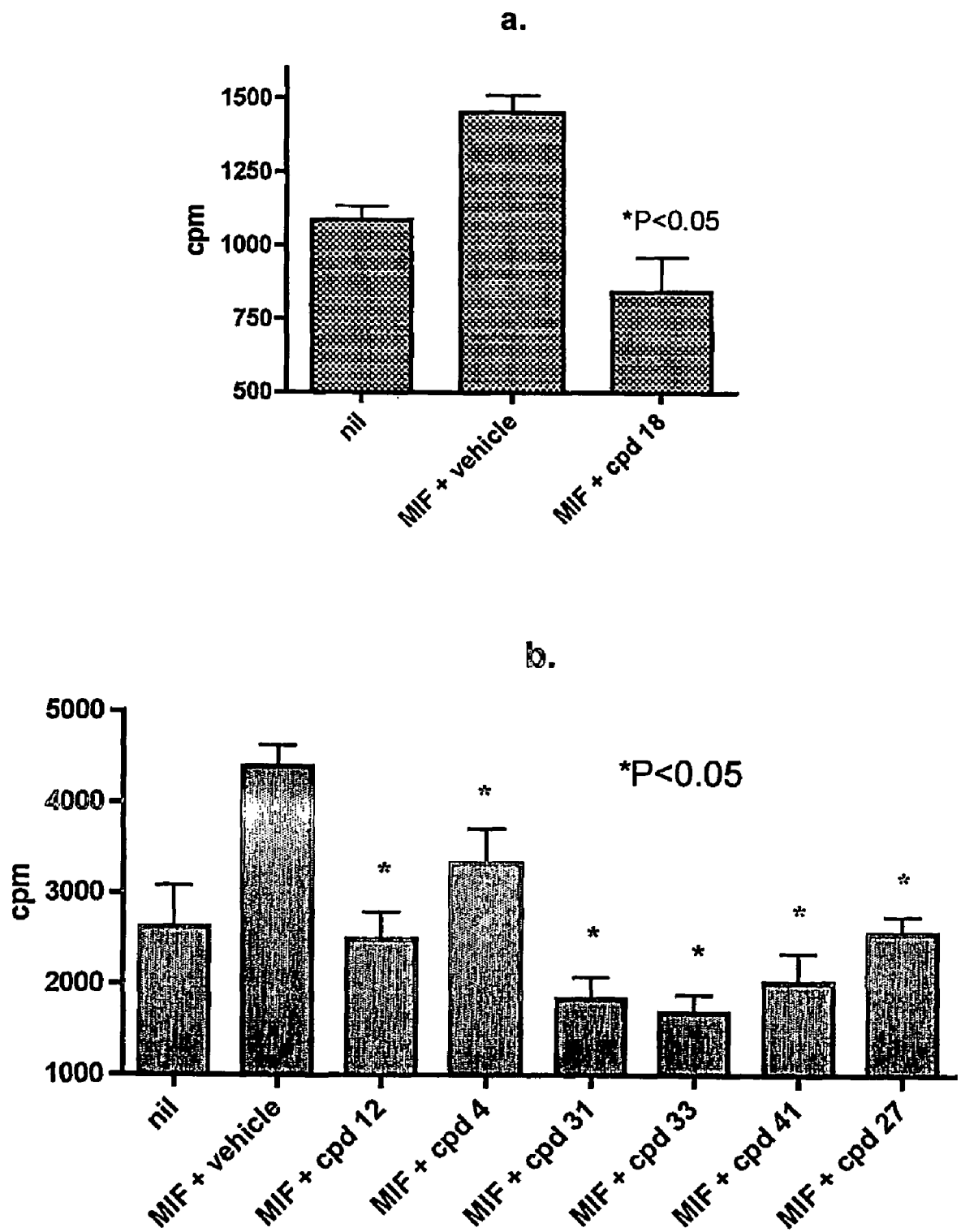
FIG. 9: graphically depicts the inhibition of MIF-induced NIH-3T3 fibroblast proliferation by 2-Methyl-2-(4-methylphenyl)-1,3-dithiolane (Compound 18) and other compounds of the invention.

Compounds of the invention were inhibitory of MIF-induced proliferation. Treatment of cells with MIF induced a significant increase in proliferation (P=0.006). Treatment with 2-Methyl-2-(4-methylphenyl)-1,3-dithiolane (Compound 18) 10 µM resulted in significant inhibition of MIF-induced proliferation (*P<0.05) (FIG. 9a). In a further experiment, treatment of cells with MIF again induced a significant increase in proliferation (P=0.004).

Other compounds of the invention resulted in significant inhibition of MIF-induced proliferation (*P<0.05) (FIG. 9b).

Table 5 displays the results for other compounds tested using this methodology. Reductions in MIF-induced proliferation were observed in cells treated with all compounds listed; where indicated these results were statistically significant. These data are consistent with these compounds exerting direct inhibitory effects on the biological activity of MIF.

TABLE 5

| Compound (10×10⁻⁶M) | Mean cpm | Std. Error | P value (compared to nil) |
|---|---|---|---|
| nil | 1087 | 48.04 | |
| MIF + vehicle | 1452 | 60.15 | 0.006 |
| Compound (10x$^{10-6}$M) | Mean cpm | Std. Error | P value (compared to MIF + vehicle) |
| 7 | 1281 | 108.1 | |
| 8 | 1238 | 95.07 | |
| 9 | 1071 | 89.58 | 0.0253 |
| 10 | 1187 | 60.35 | 0.0257 |
| 11 | 1245 | 185.1 | |
| 13 | 1015 | 60.51 | 0.0253 |
| 14 | 1420 | 93 | |
| 15 | 955.6 | 88.32 | 0.0253 |
| 16 | 1335 | 159.6 | |
| 17 | 933.2 | 216.5 | 0.0253 |
| 19 | 1209 | 51.21 | 0.0257 |
| 20 | 1214 | 87.57 | 0.0485 |
| 21 | 1220 | 107.2 | |
| 22 | 1310 | 167.1 | |
| 23 | 1344 | 126.8 | |
| 24 | 1318 | 139.3 | |
| 25 | 1117 | 101.4 | 0.0253 |
| 26 | 1141 | 125.2 | 0.0356 |
| 28 | 1219 | 46.09 | 0.0364 |
| 29 | 1157 | 192.4 | |
| 32 | 1196 | 98.5 | 0.0485 |
| 36 | 1033 | 35.98 | 0.0364 |
| 37 | 1045 | 11.19 | 0.0364 |
| 39 | 956.1 | 102.6 | 0.0253 |
| 40 | 1143 | 30.89 | 0.0364 |
| 42 | 1168 | 99.8 | |
| 43 | 1106 | 106.4 | 0.0116 |
| 44 | 1294 | 32.62 | 0.0485 |

Biological Example 8

Mouse Endotoxic Shock Model

The activity of compounds was studied in the murine endotoxic shock model. In this model, features of shock, characterised by increased serum levels of cytokines such as IL-1, tumor necrosis factor (TNF), and interleukin 6 (IL-6), are induced by the injection of bacterial lipoloysaccharide (LPS). The in vivo production of IL-1, IL-6, and TNF in response to endotoxin has been previously shown to be dependent on MIF [23]. Treatment of mice with a compound with inhibitory effects on the biological or cytokine activity of MIF could be expected to produce inhibition of serum IL-1, TNF, and/or IL-6 levels.

Methods

Groups of four mice were used in each experiment. Endotoxaemia was induced by intra-peritoneal injection of lipopolysaccharide (LPS) (5 mg/kg) in 300 µl saline. Mice injected with saline alone were used as a control group. Treatments were administered by intra-peritoneal injection at intervals 24 hours and 1 hour before intra-peritoneal LPS injection. Mice were treated with saline, compounds dissolved in DMSO/saline vehicle at a dose of 5-15 mg/kg body weight, or vehicle (containing matching concentrations of DMSO).

After 1.5 hours mice were humanely killed by CO2 inhalation then neck dislocation. Serum was obtained from blood obtained by cardiac puncture prior to death and measured for the concentration of cytokines including IL-1, TNF, and/or IL-6, by ELISA. Statistical significance was analysed using the Mann-Whitney test.

Results

Figure 10:
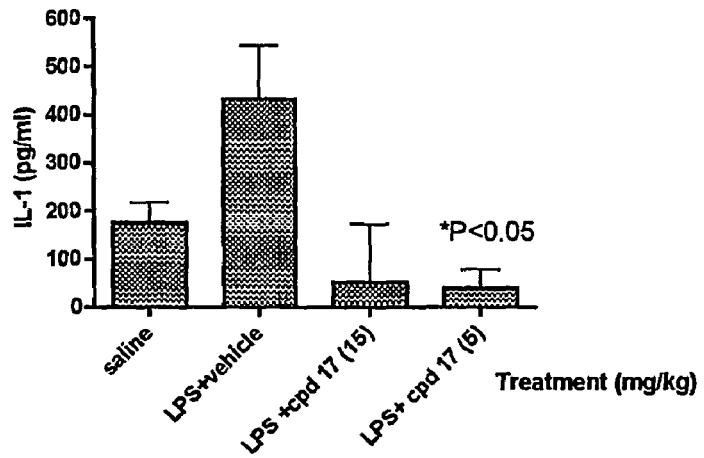
FIG. 10: graphically depicts the inhibition of lipopolysaccharide-induced serum IL-1, TNF, and IL-6 in mice treated with 2-Hexyl-2-(4-methylphenyl)-1,3-dithiolane (Compound 17).
Figure 10:
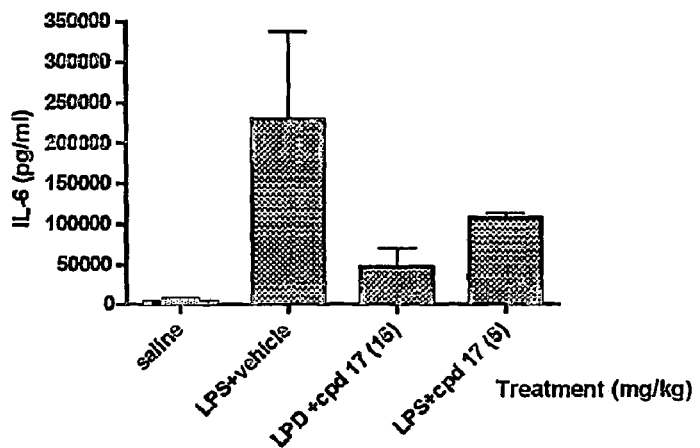
Figure 10:
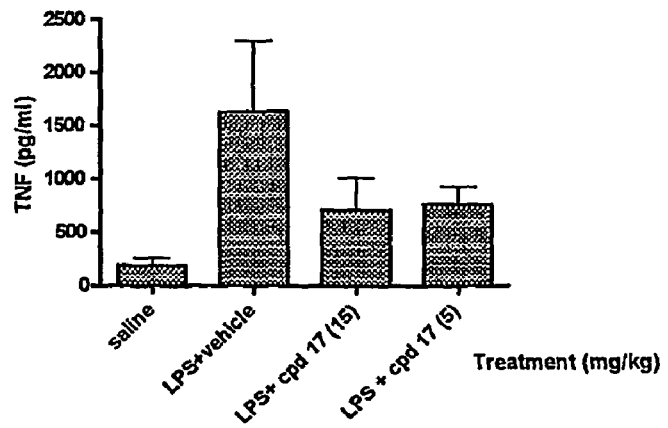

Treatment with 2-Hexyl-2-(4-methylphenyl)-1,3-dithiolane (Compound 17) was assessed. The mean±standard error of serum IL-1, IL-6, and TNF concentrations at a timepoint 1.5 h after administration of LPS are presented in FIG. 10. Compared to saline, LPS injection induced a significant cytokinaemia for each of IL-1, IL-6, and TNF ($P<0.05$). Treatment with 2-Hexyl-2-(4-methylphenyl)-1,3-dithiolane (Compound 17) (shown as cpd 17) at 5 and 15 mg/kg (as shown in brackets) was associated with marked inhibition of LPS-induced serum IL-1 (FIG. 10a), IL-6 (FIG. 10b), and TNF (FIG. 10c). In the case of IL-1, the inhibition was statistically significant (*$P<0.05$). These data are consistent with this compound exerting inhibitory effects on the biological activity of MIF.

The effect of additional compounds is presented in Table 6, in which the mean±standard error of serum IL-1, IL-6, and TNF concentrations are presented. 4-(4-Methoxyphenyl)-1-(3-methylbutyl)-1H-pyrazole (Compound 12), 1-(3-Methylbutyl)-4-(4-methylphenyl)-1H-pyrazole (Compound 13), and 2-(4-Thien-2-ylphenyl)-1,3-oxathiolane (Compound 33) were tested. An inhibitory effect of treatment with Compounds 12, 13, and 33 on serum IL-1 was observed at a dose of 5 mg/kg. An inhibitory effect of treatment with Compounds 12, 13, and 33 on serum IL-6 and TNF was observed at a dose of 15 mg/kg. These data are consistent with these compounds exerting inhibitory effects on the biological activity of MIF.

TABLE 6

| Cytokine | Saline | LPS plus vehicle | Compound 12 5 mg/kg | Compound 13 5 mg/kg | Compound 33 5 mg/kg |
|---|---|---|---|---|---|
| IL-1 (pg/ml) | 175 ± 43 | 428 ± 168 | 286 ± 102 | 305 ± 51 | 360 ± 72 |

| Cytokine | Saline | LPS plus vehicle | Compound 12 15 mg/kg | Compound 13 15 mg/kg | Compound 33 15 mg/kg |
|---|---|---|---|---|---|
| IL-6 (ng/ml) | 4 ± 4 | 118 ± 30 | 80 ± 16 | 92 ± 7 | 95 ± 14 |
| TNF (pg/ml) | 189 ± 69 | 2022 ± 1245 | 1636 ± 468 | 1067 ± 191 | 1152 ± 317 |

REFERENCES (1) David, J. Proc. Natl. Acad. Sci., USA, (1966), 56, 72-77.
(2) Weiser, W. Y., et al., Proc. Natl. Acad. Sci., USA, (1989), 86, 7522-7526.

(3) Leech M, Metz C N, Smith M, Weedon H, Holdsworth S R, Bucala R, et al. Macrophage migration inhibitory factor (MIF) in rheumatoid arthritis: Evidence for pro-inflammatory function and regulation by glucocorticoids. Arthritis & Rheumatism 1999; 42:1601-1608.

(4) Morand E F, Bucala R, Leech M. Macrophage migration inhibitory factor (MIF): An emerging therapeutic target in rheumatoid arthritis. Arthritis & Rheumatism 2003; 48:291-299.

(5) Calandra T, Bernhagen J, Metz C N, Spiegel L A, Bacher M, Donnelly T, et al. MIF as a glucocorticoid-induced modulator of cytokine production. Nature 1995; 377:68-71.

(6) Donnelly S C, Haslett C, Reid P T, Grant I S, Wallace W A H, Metz C N, I. Regulatory role for macrophage migration inhibitory factor in acute respiratory distress syndrome. Nature Medicine 1997; 3:320-323.

(7) Bacher M, Metz C N, Calandra T, Mayer K, Chesney J, Lohoff M, et al. An essential regulatory role for macrophage migration inhibitory factor in T-cell activation. Proceedings of the National Academy of Sciences USA 1996; 3:7849-7854.

(8) Santos L L, Hall P, Metz C N, Bucala R, Morand E F. Role of macrophage migration inhibitory factor (MIF) in murine antigen-induced arthritis: Interaction with glucocorticoids. Clin. Exp. Immunol. 2001; 123:309-314.

(9) Leech M, Santos L L, Metz C, Holdsworth S R, Bucala R, Morand E F. Control of macrophage migration inhibitory factor (MIF) by endogenous glucocorticoids in rat adjuvant arthritis. Arthritis & Rheumatism 2000; 43:827-833.

(10) Bucala R. MIF rediscovered: cytokine, pituitary hormone, and glucocorticoid-induced regulator of the immune response. FASEB. J. 1996; 10:1607-1613.

(11) Sabroe I, Pease J E, Williams T J. Asthma and MIF: innately Th1 and Th2. Clin Exp Allergy 2000; 30(9):1194-6.

(12) Eur. J. Med. Chem—Chim. Ther., 17(3), 235-43, (1982).

(13) Synthetic Communications, 30(6), 1083-1094, (2000).

(14) J. Am. Pharm. Assoc., 38, 9-11, (1949).

(15) J. Org. Chem., 63 (12), 4116-4119, (1998).

(16) Lacey D, Sampey A, Mitchell R, Bucala R, Santos L, Leech M. Morand E F. Control of fibroblast-like synoviocyte proliferation by macrophage migration inhibitory factor (MIF). Arthritis Rheum 48:103-9, 2003.

(17) Sampey A, Hall P, Morand E F. Regulation of Synoviocyte PLA2 and COX2 By Macrophage Migration Inhibitory Factor. Arthritis Rheum 44:1273-1280, 2001.

(18) Sampey A, Morand E F. Annexin I inhibition of human synoviocyte phospholipase A2 but not cyclooxygenase-2 activity. Mediators of Inflammation 9:125-132, 2000.

(19) Leech M, Lacey D, Xue J R, Santos L, Hutchinson P, Wolvetang E, David J R, Bucala R, Morand E F. Macrophage migration inhibitory factor (MIF) regulates p53 in inflammatory arthritis. Arthritis Rheum 2003.

(20) Juttner S, Bernhagen J, Metz C N, Rollinghoff M, Bucala R, Gessner A. Migration inhibitory factor induces killing of Leishmania major by macrophages: dependence on reactive nitrogen intermediates and endogenous TNF. *J. Immunol.* 1998; 161:2383-2390.

(21) Santos L L, Morand E F, Holdsworth S R. Suppression of adjuvant arthritis and synovial macrophage inducible nitric oxide by N-iminoethyl-1-ornithine, a nitric oxide synthase inhibitor. *Inflammation* 1997; 21:299-311.

(22) Mitchell R A, Metz C N, Peng T, Bucala R. Sustained mitogen-activated protein kinase (MAPK) and cytoplasmic phospholipase A2 activation by macrophage migration inhibitory factor (MIF). Regulatory role in cell proliferation and glucocorticoid action. *Journal of Biological Chemistry* 1999; 274:18100-18106.

(23) Bozza M, Satoskar A B, Lin G, Lu B, Humbles A A, Gerard C, et al. Targeted disruption of Migration Inhibitory Factor gene reveals its critical role in sepsis. *Journal of Experimental Medicine* 1999; 189:341-346.

The invention claimed is:

1. A compound wherein the compound is 1-(3-methylbutyl)-4-(4-methylphenyl)-1H-pyrazole or a pharmaceutically acceptable salt thereof.

* * * * *